United States Patent
Wang et al.

(10) Patent No.: US 10,751,344 B2
(45) Date of Patent: *Aug. 25, 2020

(54) CARBON MONOXIDE-RELEASING MOLECULES FOR THERAPEUTIC APPLICATIONS AND METHODS FOR THE PREPARATION AND USE THEREOF

(71) Applicant: Georgia State University Research Foundation, Inc., Atlanta, GA (US)

(72) Inventors: Binghe Wang, Marietta, GA (US); Danzhu Wang, Atlanta, GA (US); Xingyue Ji, Atlanta, GA (US); Alexander Draganov, Atlanta, GA (US); Chaofeng Dai, Atlanta, GA (US); Krishna Damera, Smyrna, GA (US); Didier Merlin, Decatur, GA (US); Emilie Viennois, Atlanta, GA (US); Yueqin Zheng, Atlanta, GA (US)

(73) Assignee: GEORGIA STATE UNIVERSITY RESEARCH FOUNDATION, INC., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/423,094

(22) Filed: May 27, 2019

(65) Prior Publication Data
US 2019/0350937 A1 Nov. 21, 2019

Related U.S. Application Data

(63) Continuation of application No. 15/317,705, filed as application No. PCT/US2015/034948 on Jun. 9, 2015, now Pat. No. 10,300,069.

(Continued)

(51) Int. Cl.
*A61K 31/122* (2006.01)
*A61K 31/5375* (2006.01)
(Continued)

(52) U.S. Cl.
CPC ........ *A61K 31/5375* (2013.01); *A61K 31/015* (2013.01); *A61K 31/122* (2013.01);
(Continued)

(58) Field of Classification Search
CPC .................................................. A61K 31/122
See application file for complete search history.

(56) References Cited

U.S. PATENT DOCUMENTS

| | | | |
|---|---|---|---|
| 5,670,664 | A | 9/1997 | Kao et al. |
| 10,300,069 | B2 | 5/2019 | Wang et al. |
| 2017/0128456 | A1 | 5/2017 | Wang et al. |

FOREIGN PATENT DOCUMENTS

| | | |
|---|---|---|
| CN | 106794362 | 5/2017 |
| EP | 3151919 | 4/2017 |

(Continued)

OTHER PUBLICATIONS

Ukrainskii Khimicheskii, vol. 47, Issue 6, 1981, pp. 646-649.
(Continued)

*Primary Examiner* — Benjamin J Packard
(74) *Attorney, Agent, or Firm* — Kilpatrick Townsend & Stockton, LLP

(57) ABSTRACT

Carbon monoxide-releasing organic molecules are described herein. The molecules can be synthesized prior to administration (e.g., ex vivo) or formed in vivo. In those embodiments where the molecules are formed in vivo, reactants are administered under physiological conditions and undergo a cycloaddition reaction to form a product which releases carbon monoxide. In applying such reactions for therapeutic applications in vivo, the cycloaddition and CO release typically occur only under near-physiological or physiological conditions. For example, in some embodiments, the cycloaddition reaction and/or release of carbon monoxide occur at a temperature of about 37° C. and pH of about 7.4.

(Continued)

Pharmaceutical compositions and methods for release carbon monoxide are also described.

20 Claims, 17 Drawing Sheets

Related U.S. Application Data

(60) Provisional application No. 62/009,451, filed on Jun. 9, 2014.

(51) Int. Cl.
    *A61K 31/015*     (2006.01)
    *A61K 31/216*     (2006.01)
    *C07B 37/12*     (2006.01)
    *C01B 32/40*     (2017.01)
    *A61K 47/54*     (2017.01)
    *A61K 47/61*     (2017.01)
    *A61K 31/166*     (2006.01)
    *A61K 31/235*     (2006.01)

(52) U.S. Cl.
    CPC .......... *A61K 31/166* (2013.01); *A61K 31/216* (2013.01); *A61K 31/235* (2013.01); *A61K 47/549* (2017.08); *A61K 47/61* (2017.08); *C01B 32/40* (2017.08); *C07B 37/12* (2013.01)

(56) References Cited

FOREIGN PATENT DOCUMENTS

| | | |
|---|---|---|
| JP | 2017528416 | 9/2017 |
| WO | 03066067 | 8/2013 |
| WO | 2015191616 | 12/2015 |

OTHER PUBLICATIONS

Ji et al., "Click and Release: A Chemical Strategy toward Developing Gasotransmitter Prodrugs by Using an Intramolecular Diels-Alder Reaction", Angewandte Chemie International Edition, vol. 55, No. 51, Nov. 23, 2016, pp. 15846-15851.

Ji, et al. "Toward Carbon Monoxide Based Therapeutics: Critical Drug Delivery and Developability Issues." Journal of Pharmaceutical Sciences 105 (2016) 406-416.

Kitamura et al., "A New Hypervalent Iodine Precursor of a Highly Strained Cyclic Alkyne. Generation and Trapping Reactions of Bicyclo[2.2.1]hept-2-en-5-yne", Communications, J. Org. Chem., vol. 64, No. 3, Dec. 31, 1999, pp. 680-681.

Kobylyanskii et al., "Synthesis of Oxytri (Alkoxycarbonyl) Cyclopentadienones and their Dimers from Unsaturated Acetyldicarboxylic Acid Esters", Database CA, Chemical Abstracts Service, Ukrainskii Khimicheskii Zhurnal (Russian Edition), vol. 47, No. 6, ISSN: 0041-6045, 1981, 3 pages.

Kuzmanich, et al. "Ring strain release as a strategy to enable the singlet state photodecarbonylation of crystalline 1,4-cyclobutanediones." J Phys Org Chem. 2011;24:883-888.

L'Abbe, "Heterocyclic analogues of methylenecyclopropanes." Angew Chem Int Ed Engl. 1980;19:276-289.

Mikol, et al. "Photo-induced decarbonylation of b-styryl isocyanates." J Chem Soc Chem Commun. 1972;8:439.

Mondal, et al. "Photogeneration of heptacene in a polymer matrix." J Am Chem Soc. 2006;128:9612-9613.

Mondal, et al. "Photodecarbonylation of a-diketones: a mechanistic study of reactions leading to acenes." J Phys Chem B. 2008;112:11-15.

Motterlini, et al. "The therapeutic potential of carbon monoxide." Nat Rev Drug Discov. 2010;9:728-743.

Pan et al., "Organic CO Prodrugs: Structure-CO-Release Rate Relationship Studies", Chemistry—A European Journal, vol. 23, No. 41, Jul. 4, 2017, pp. 9838-9845.

Peng, et al. "Visible-light activatable organic CO-releasing molecules (photoCORMs) that simultaneously generate fluorophores." Org Biomol Chem. 2013;11:6671-6674.

Wang et al., "A Click-and-Release Approach to CO Prodrugs", Chemical Communications, vol. 50, No. 100, Oct. 31, 2014, pp. 15890-15893.

Wang, et al. "3,6-substituted-1,2,4,5-tetrazines: tuning reaction rates for staged labeling applications." Org Biomol Chem. 2014;12:3950-3955.

Antony, et al. "Fluorescein analogue xanthene-9-carboxylic acid: a transition-metal-free CO releasing molecule activated by green light." Org Lett. 2013;15:4552-4555.

Chen, et al. "Clicking 1,2,4,5-tetrazine and cyclooctynes with tunable reaction rates." Chem Commun. 2012;48:1736-1738.

Heinemann, et al. "Carbon monoxide-physiology, detection and controlled release." Chem Commun. 2014;50:3644-3660.

Horspool, et al. "Photo-decarbonylation of coumarandiones." J Chem Soc D. 1970;5:257-258.

Uno, et al. "Photo precursor for pentacene." Tetrahedron Lett. 2005;46:1981-1983.

Wegiel, et al. "The social network of carbon monoxide in medicine." Trends Mol Med. 2013;19:3-11.

Yamada, et al. "Synthesis and photochemical properties of a-diketoporphyrins as precursors for p-expanded porphyrins." J Mater Chem. 2010;20:3011-3024.

International Searching Authority; International Search Report and Written Opinion received in International Application No. PCT/US2015/034948, dated Nov. 10, 2015, 12 pages.

CARBON MONOXIDE-RELEASING MOLECULES FOR THERAPEUTIC APPLICATIONS AND METHODS FOR THE PREPARATION AND USE THEREOF

CROSS-REFERENCES TO RELATED APPLICATIONS

The present application is continuation of U.S. patent application Ser. No. 15/317,705, filed on Dec. 9, 2016, which is a U.S. National Stage Entry of International Pat. Appl. No. PCT/US2015/034948, filed Jun. 9, 2015, which claims priority to U.S. Provisional Pat. Appl. No. 62/009,451, filed on Jun. 9, 2014, which applications are incorporated herein by reference in their entirety for all purposes.

STATEMENT AS TO RIGHTS TO INVENTIONS MADE UNDER FEDERALLY SPONSORED RESEARCH AND DEVELOPMENT

The present invention was made with government support under Grant No. CA180519 awarded by the National Institutes of Health. The government has certain rights in the invention.

FIELD OF THE INVENTION

This invention is in the field of molecules that generate carbon monoxide, particularly in vivo or ex vivo.

BACKGROUND OF THE INVENTION

Carbon monoxide (CO) is well-known as a lethal, toxic gas. However, CO is also an important member of the gasotransmitter family of signaling molecules in mammalian systems whose importance is on par with that of NO and $H_2S$. NO was the first identified gaseous small molecule biological messenger in mammals. Nitroglycerin (glyceryl trinitrate) serves as an exogenous source of NO and is the most widely used drug for vasodilation and treatment of heart conditions.

CO also has beneficial therapeutic effects. The endogenous production of CO in a mammalian system occurs through the activity of heme oxygenases (HO-1 and HO-2). These enzymes regulate the catabolism of heme and play an important role in the modulation of a variety of responses, such as stress response and circadian rhythm. Studies have shown that CO has anti-inflammatory, anti-proliferative, and anti-apoptotic effects when the concentrations of CO in carrier gas (air) ranges from 10 to 250 ppm.

CO has been found to play a key beneficial role in various inflammatory and cardiovascular diseases. Among the various inflammatory related disorders, inflammatory bowel disease (IBD), psoriasis, mid-ear infection-induced inflammation, uveitis, and burn- and injury-related inflammation can be effectively treated by CO. For some of the inflammation related conditions, the detailed mechanism may not necessarily be entirely clear. For example, the pathogenesis of IBD is still unclear due to multiple factors involved in the inflammatory processes such as genetic mutations, bacterial infections, and physiological and immunological stress responses. Tumor necrosis factor alpha (TNF-α) plays a central role in the pathogenesis of IBD, as evidenced by the successful treatment of patients with anti-TNF-α antibodies in multiple clinical trials. The anti-inflammatory effects of CO have been reported using cell culture and animal models of sepsis. CO administration or HO-1 overexpression in RAW 264.7 cells inhibits TNF-α expression after treatment with lipopolysaccharide (LPS). In several inflammatory models, CO has been reported to inhibit Granulocyte-Macrophage Colony-Stimulating Factor (GM-CSF) expression, resulting in attenuation of inflammation. The effective and targeted treatments of IBD are largely limited due to significant systemic side effects. Until now, anti-inflammatory drugs and immunosuppressants are two options used in IBD treatment. There are some mitogen-activated protein kinase (MAPK) inhibitors being developed as treatment options. For other inflammation-related symptoms, the situation is similar. For example, psoriasis has limited effective treatment options, e.g., corticoid hormone and anti-TNFα.

Rheumatoid arthritis and osteoarthritis are two more examples of inflammatory disorders that can be treated with CO. Administration of CO from carbon monoxide releasing molecules (CORMs) in a model of collagen-induced arthritis suppressed the clinical and histopathological manifestations of the disease. The data is consistent with the reduction in the levels of inflammatory cytokines such as interleukins and TNF-α in joint tissue, and showed decreased cellular infiltration, joint inflammation and cartilage destruction.

Besides anti-inflammatory effects, evidence suggests that CO plays a beneficial role in treating cardiovascular disease. Pulmonary arterial hypertension (PAH), one type of pulmonary hypertension, is an incurable disease at this moment, and is described as high blood pressure in the arteries of the lungs. It is driven by an increased expansion of vascular smooth muscle in the pulmonary arterioles and leads to right heart hypertrophy and infarct. Breathing low concentrations of CO gas (e.g., 150 ppm) has been investigated as a treatment to improve pulmonary arterial hypertension and is currently in phase II clinical trials. Preliminary results have shown that after 16 weeks, the pulmonary vascular resistance has decreased 20% compared to the pre-therapy value. The mechanism of action of CO in the treatment of PAH has been reported as involving endothelial derived NO to induce apoptosis of the hyper-proliferative vascular smooth muscle cells.

A key issue in the use of CO as a therapeutic agent is the safe delivery of low doses to the desired site of action. A number of Carbon Monoxide Releasing Molecules (CORMs) have been investigated. Currently available CO delivery systems are metal-containing CORMs that can release CO, especially upon exposure to light and/or water. Manganese-based photo CORMs are representative of these molecules. However, for medicinal applications, especially for systemic administration, overcoming the toxicity of residual metal ions is a key issue.

Boric acid complexes have been investigated for non-photochemical approaches for the delivery of CO in vivo. In the case of CO delivery using UV irradiation, the rate of CO release is generally slow (half-life about 20-fold slower than that of metal-CORMs) and toxicity issues have limited the development of these compounds. Besides organometallic compounds, dialkylaldehydes, oxalates, boroncarboxylates and silacarboxylates are CORMs that are transition-metal free and can release CO under mild conditions. Boroncarboxylates are well known CO releasers and possess good water solubility. Disodium boranocarbonate, for example, has been used in animal models for disease treatment. Silacarboxylic acids ($R_3SiCOOH$) can deliver stoichiometric amounts of CO in the presence a nucleophile. However, toxicity issues and limited ability for chemical transformations make these molecules unsuitable candidates for therapeutic applications.

Some organic reactions release CO as a byproduct. However, the need to use UV light to activate these molecules is a limitation in their application as medicinal agents.

Therefore, there is a need for molecules that generate CO in vivo and in vitro with little or no toxicity and without the need for external stimuli. The present invention addresses this and other needs.

BRIEF SUMMARY OF THE INVENTION

In a first aspect, the invention provides a method for generating carbon monoxide in vivo or ex vivo. The method includes combining a first unsaturated molecule and a second unsaturated molecule under physiological conditions and allowing the unsaturated molecules to react to form an organic molecule that releases an effective amount of carbon monoxide; or allowing a precursor molecule having a first site of unsaturation and a second site of unsaturation to react under physiological conditions to form an organic molecule that releases an effective amount of carbon monoxide.

In some embodiments, the first unsaturated molecule is a diene and the second unsaturated molecule is a dienophile. In some embodiments, the diene has a structure according to Formula I:

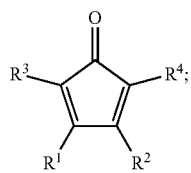

(I)

or a pharmaceutically acceptable salt thereof, wherein:
each $R^1$, $R^2$, $R^3$, and $R^4$ is independently selected from the group consisting of hydrogen, halogen, alkyl, cycloalkyl, heterocycloalkyl, alkenyl, alkynyl, aryl, heteroaryl, alkoxy, aryloxy, hydroxyl, —N(R$^a$)$_2$, —SR$^a$, —S(O)R$^a$, —S(O)$_2$R$^a$, —OS(O)OR$^a$, —OS(O)$_2$OR$^a$, —OP(OR$^a$)$_2$, —OP(O)HOR$^a$, —OP(O)(OR$^a$)$_2$, —OP(O)(R$^a$)$_2$, —P(O)(OR$^a$)$_2$, —ONO, —ONO$_2$, —NO$_2$, —(C=O)R$^5$, —(C=O)OR$^6$, —(C=O)NR$^7$R$^8$, a linking moiety R$^L$, a targeting moiety R$^T$, and a solubility-enhancing moiety R$^S$;

or, alternatively, $R^1$ and $R^2$ are independently selected from the group consisting of cycloalkyl, heterocycloalkyl, aryl, and heteroaryl, and are taken together to form a fused tricyclic moiety which is optionally substituted with one or more R$^9$ moieties, wherein each R$^9$ is independently selected from the group consisting of halogen, alkyl, cycloalkyl, heterocycloalkyl, alkenyl, alkynyl, aryl, heteroaryl, alkoxy, aryloxy, hydroxyl, —N(R$^a$)$_2$, —SR$^a$, —S(O)R$^a$, —S(O)$_2$R$^a$, —OS(O)OR$^a$, —OS(O)$_2$OR$^a$, —OP(OR$^a$)$_2$, —OP(O)HOR$^a$, —OP(O)(OR$^a$)$_2$, —OP(O)(R$^a$)$_2$, —P(O)(OR$^a$)$_2$, —ONO, —ONO$_2$, —NO$_2$, —(C=O)R$^5$, —(C=O)OR$^6$, —(C=O)NR$^7$R$^8$, a linking moiety R$^L$, a targeting moiety R$^T$, and a solubility-enhancing moiety R$^S$;

each $R^5$, $R^6$, $R^7$, and $R^8$ is independently selected from the group consisting of hydrogen, alkyl, heteroalkyl, alkenyl, heteroalkenyl, alkynyl, heteroalkynyl, cycloalkyl, heterocycloalkyl, aryl, and heteroaryl; and R$^a$ is selected from the group consisting of H, alkyl, aryl, cycloalkyl, and heteroaryl.

In some embodiments, the diene has a structure according to Formula IV:

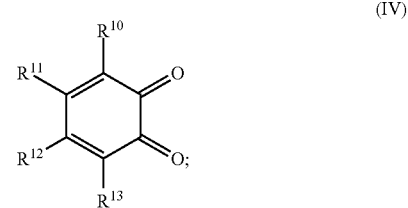

(IV)

or a pharmaceutically acceptable salt thereof, wherein:
each $R^{10}$, $R^{11}$, $R^{12}$ and $R^{13}$ is independently selected from the group consisting of hydrogen, halogen, alkyl, cycloalkyl, heterocycloalkyl, alkenyl, alkynyl, aryl, heteroaryl, alkoxy, aryloxy, hydroxyl, —N(R$^a$)$_2$, —SR$^a$, —S(O)R$^a$, —S(O)$_2$R$^a$, —OS(O)OR$^a$, —OS(O)$_2$OR$^a$, —OP(OR$^a$)$_2$, —OP(O)HOR$^a$, —OP(O)(OR$^a$)$_2$, —OP(O)(R$^a$)$_2$, —P(O)(OR$^a$)$_2$, —ONO, —ONO$_2$, —NO$_2$, —(C=O)R$^5$, —(C=O)OR$^6$, —(C=O)NR$^7$R$^8$, a linking moiety R$^L$, a targeting moiety R$^T$, and a solubility-enhancing moiety R$^S$;

R$^a$ is selected from the group consisting of hydrogen, alkyl, cycloalkyl, aryl or heteroaryl; and each $R^5$, $R^6$, $R^7$, and $R^8$ is independently selected from the group consisting of hydrogen, alkyl, heteroalkyl, alkenyl, heteroalkenyl, alkynyl, heteroalkynyl, cycloalkyl, heterocycloalkyl, aryl, and heteroaryl.

In some embodiments, the dienophile has a structure according to Formula V:

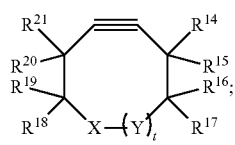

(V)

or a pharmaceutically acceptable salt thereof, wherein:
each $R^{14}$, $R^{15}$, $R^{16}$, $R^{17}$, $R^{18}$, $R^{19}$, $R^{20}$, and $R^{21}$ is independently selected from the group consisting of hydrogen, halogen, substituted or unsubstituted alkyl, cycloalkyl, heterocycloalkyl, alkenyl, alkynyl, aryl, heteroaryl, alkoxy, or aryloxy, hydroxyl, —N(R$^a$)$_2$, —SR$^a$, —S(O)R$^a$, —S(O)$_2$R$^a$, —OS(O)OR$^a$, —OS(O)$_2$OR$^a$, —OP(OR$^a$)$_2$, —OP(O)HOR$^a$, —OP(O)(OR$^a$)$_2$, —OP(O)(R$^a$)$_2$, —P(O)(OR$^a$)$_2$, —ONO, —ONO$_2$, —NO$_2$, —(C=O)R$^{5'}$, —(C=O)OR$^{6'}$, —(C=O)NR$^{7'}$R$^{8'}$, a linking moiety R$^L$, a targeting moiety R$^T$, and a solubility-enhancing moiety R$^S$;

each $R^{5'}$, $R^{6'}$, $R^{7'}$, and $R^{8'}$ is independently selected from the group consisting of hydrogen, alkyl, heteroalkyl, alkenyl, heteroalkenyl, alkynyl, heteroalkynyl, cycloalkyl, heterocycloalkyl, aryl, and heteroaryl;

$R^{14}$ or $R^{15}$ is optionally taken together with $R^{16}$ or $R^{17}$ to form fused cycloalkyl, fused heterocyclyl, fused aryl, or fused heteroaryl, each of which is optionally substituted with R$^{9'}$;

$R^{18}$ or $R^{19}$ is optionally taken together with $R^{20}$ or $R^{21}$ to form fused cycloalkyl, fused heterocyclyl, fused aryl, or fused heteroaryl, each of which is optionally substituted with R$^{9'}$;

each $R^{9'}$ is independently selected from the group consisting of halogen, alkyl, cycloalkyl, heterocycloalkyl, alkenyl, alkynyl, aryl, heteroaryl, alkoxy, aryloxy, hydroxyl, —N($R^a$)$_2$, —S$R^a$, —S(O)$R^a$, —S(O)$_2R^a$, —OS(O)O$R^a$, —OS(O)$_2$O$R^a$, —OP(O$R^a$)$_2$, —OP(O)H O$R^a$, —OP(O)(O$R^a$)$_2$, —OP(O)($R^a$)$_2$, —P(O)(O$R^a$)$_2$, —ONO, —ONO$_2$, —NO$_2$, —(C=O)$R^5$, —(C=O)O$R^6$, —(C=O)N$R^7R^8$, a linking moiety $R^L$, a targeting moiety $R^T$, and a solubility-enhancing moiety $R^S$;

Y is selected from the group consisting of C$R^{22a}R^{22b}$, S, O, and N$R^a$;

X is selected from the group consisting of C$R^{23a}R^{23b}$, S, O, and N$R^a$;

wherein each $R^{22a}$, $R^{22b}$, $R^{23a}$, and $R^{23b}$ is defined as for $R^{5'}$;

wherein $R^{22a}$ or $R^{22b}$ is optionally taken together with $R^{23a}$ or $R^{23b}$ to form a cyclic moiety optionally substituted with $R^{9'}$;

$R^a$ is selected from the group consisting of hydrogen, alkyl, cycloalkyl, aryl and heteroaryl; and subscript t is 0 or 1.

In some embodiments, the precursor molecule has a structure according to Formula IX:

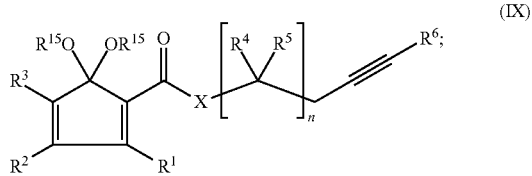

(IX)

or a pharmaceutically acceptable salt thereof, wherein:
each $R^1$, $R^2$, $R^3$, $R^4$, $R^5$, and $R^6$ is independently selected from the group consisting of hydrogen, halogen, substituted or unsubstituted alkyl, cycloalkyl, heterocycloalkyl, alkenyl, alkynyl, aryl, heteroaryl, alkoxy, aryloxy, hydroxyl, —N($R^a$)$_2$, —S$R^a$, —S(O)$R^a$, —S(O)$_2R^a$, —OS(O)O$R^a$, —OS(O)$_2$O$R^a$, —OP(O$R^a$)$_2$, —OP(O)H O$R^a$, —OP(O)(O$R^a$)$_2$, —OP(O)($R^a$)$_2$, —P(O)(O$R^a$)$_2$, —ONO, —ONO$_2$, —NO$_2$, —(C=O)$R^7$, —(C=O)O$R^8$, —(C=O)N$R^9R^{10}$, a protecting moiety $R^P$, a linking moiety $R^L$, a targeting moiety $R^T$, and a solubility-enhancing moiety $R^S$;

or, alternatively, $R^1$ and $R^2$ are independently selected from the group consisting of cycloalkyl, heterocycloalkyl, aryl, and heteroaryl, and are taken together to form a fused tricyclic moiety which is optionally substituted with one or more $R^{11}$ moieties, wherein each $R^{11}$ is independently selected from the group consisting of halogen, alkyl, cycloalkyl, heterocycloalkyl, alkenyl, alkynyl, aryl, heteroaryl, alkoxy, aryloxy, hydroxyl, —N($R^a$)$_2$, —S$R^a$, —S(O)$R^a$, —S(O)$_2R^a$, —OS(O)O$R^a$, —OS(O)$_2$O$R^a$, —OP(O$R^a$)$_2$, —OP(O)H O$R^a$, —OP(O)(O$R^a$)$_2$, —OP(O)($R^a$)$_2$, —P(O)(O$R^a$)$_2$, —ONO, —ONO$_2$, —NO$_2$, —(C=O)$R^5$, —(C=O)O$R^6$, —(C=O)N$R^7R^8$, a linking moiety $R^L$, a targeting moiety $R^T$, and a solubility-enhancing moiety $R^S$;

$R^a$ is selected from the group consisting of hydrogen, alkyl, cycloalkyl, aryl or heteroaryl;

each $R^7$, $R^8$, $R^9$, and $R^{10}$ is independently selected from the group consisting of hydrogen, alkyl, heteroalkyl, alkenyl, heteroalkenyl, alkynyl, heteroalkynyl, cycloalkyl, heterocycloalkyl, aryl, and heteroaryl;

X is C$R^{12}R^{13}$, S, O, or N$R^{14}$, wherein each $R^{12}$ and $R^{13}$ is defined as for $R^1$, and $R^{14}$ is defined as for $R^7$;

each $R^{15}$ is independently selected from the group consisting of hydrogen, alkyl, cycloalkyl, heterocycloalkyl, alkenyl, alkynyl, aryl, and heteroaryl, or, alternatively two O$R^{15}$ are taken together to form an oxo moiety; and subscript n is 1, 2 or 3.

In some embodiments, the precursor molecule has a structure according to Formula XII:

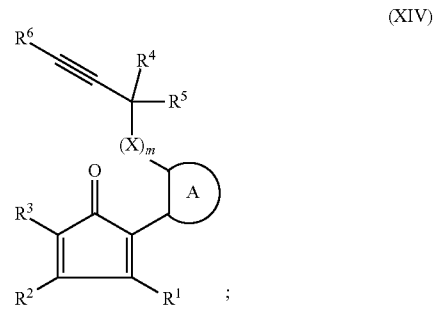

(XIV)

or a pharmaceutically acceptable salt thereof, wherein:
each $R^1$, $R^2$, $R^3$, $R^4$, $R^5$, and $R^6$ is independently selected from the group consisting of hydrogen, halogen, substituted or unsubstituted alkyl, cycloalkyl, heterocycloalkyl, alkenyl, alkynyl, aryl, heteroaryl, alkoxy, aryloxy, hydroxyl, —N($R^a$)$_2$, —S$R^a$, —S(O)$R^a$, —S(O)$_2R^a$, —OS(O)O$R^a$, —OS(O)$_2$O$R^a$, —OP(O$R^a$)$_2$, —OP(O)H O$R^a$, —OP(O)(O$R^a$)$_2$, —OP(O)($R^a$)$_2$, —P(O)(O$R^a$)$_2$, —ONO, —ONO$_2$, —NO$_2$, —(C=O)$R^7$, —(C=O)O$R^8$, —(C=O)N$R^9R^{10}$, a protecting moiety $R^P$, a linking moiety $R^L$, a targeting moiety $R^T$, and a solubility-enhancing moiety $R^S$;

or, alternatively, $R^1$ and $R^2$ are independently selected from the group consisting of cycloalkyl, heterocycloalkyl, aryl, and heteroaryl, and are taken together to form a fused tricyclic moiety which is optionally substituted with one or more $R^{11}$ moieties, wherein each $R^{11}$ is selected from the group consisting of hydrogen, halogen, alkyl, cycloalkyl, heterocycloalkyl, alkenyl, alkynyl, aryl, heteroaryl, alkoxy, aryloxy, hydroxyl, —N($R^a$)$_2$, —S$R^a$, —S(O)$R^a$, —S(O)$_2R^a$, —OS(O)O$R^a$, —OS(O)$_2$O$R^a$, —OP(O$R^a$)$_2$, —OP(O)HO$R^a$, —OP(O)(O$R^a$)$_2$, —OP(O)($R^a$)$_2$, —P(O)(O$R^a$)$_2$, —ONO, —ONO$_2$, —NO$_2$, —(C=O)$R^5$, —(C=O)O$R^6$, —(C=O)N$R^7R^8$, a linking moiety $R^L$;

$R^a$ is selected from the group consisting of hydrogen, alkyl, cycloalkyl, aryl or heteroaryl;

each $R^7$, $R^8$, $R^9$, and $R^{10}$ is independently selected from the group consisting of hydrogen, alkyl, heteroalkyl, alkenyl, heteroalkenyl, alkynyl, heteroalkynyl, cycloalkyl, heterocycloalkyl, aryl, and heteroaryl;

X is C$R^{12}R^{13}$, S, O, or N$R^{14}$, wherein each $R^{12}$ and $R^{13}$ is defined as for $R^1$, and $R^{14}$ is defined as for $R^7$;

"A" is selected from the group consisting of cycloalkyl, heterocycloalkyl, aryl, and heteroaryl; and subscript m is 1, 2 or 3, provided that only one of X is S or O when m is 2 or 3.

In a related aspect, the invention provides a pharmaceutical composition comprising one or more pharmaceutically acceptable excipients and: a first unsaturated molecule and a second unsaturated molecule that react to form a cycloaddition product that releases an effective amount of carbon monoxide under physiological conditions; or a precursor molecule having a first site of unsaturation and a second site of unsaturation that react to form a cycloaddition product that releases an effective amount of carbon monoxide under physiological conditions.

DETAILED DESCRIPTION OF THE INVENTION

I. Introduction

Figure 1A:
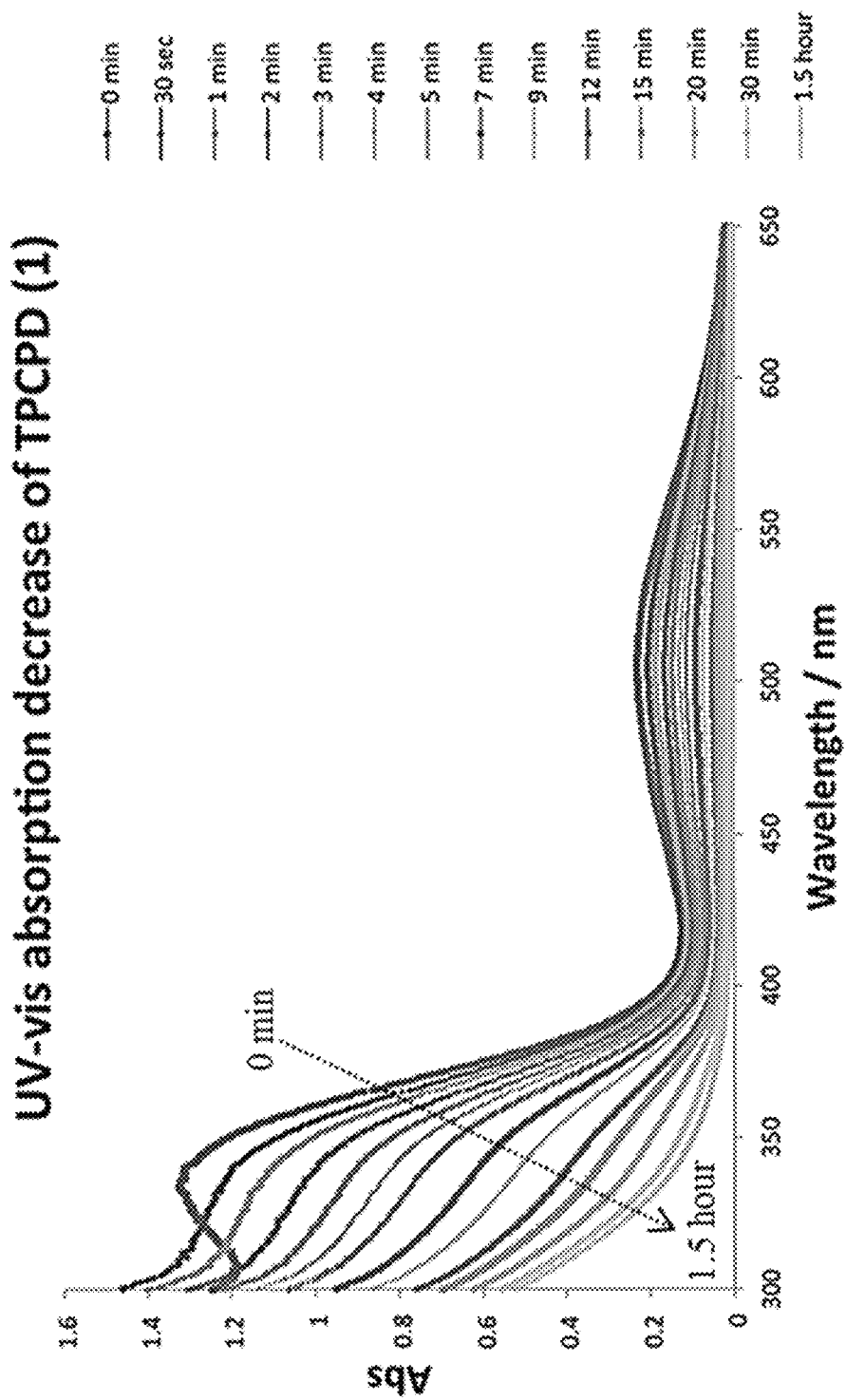
FIG. 1A shows a UV-Vis absorption spectrum of the reaction between TPCPD and BCN as a function of time.

Carbon monoxide-releasing organic molecules are described herein. The molecules can be synthesized prior to administration (e.g., ex vivo) or formed in vivo. In those embodiments where the molecules are formed in vivo, reactants are administered in vivo and undergo a cycloaddition reaction, such as intermolecular inverse-electron demand Diels Alder reaction (DARinv) and intramolecular DARinv, to form a product which releases carbon monoxide under physiological conditions. In some embodiments, a fluorophore along with carbon monoxide is also released, which facilitates the real-time monitoring of CO release, and also CO release kinetics. In applying such reactions for therapeutic applications in vivo, the CO release typically occurs only under near-physiological or physiological conditions. For example, in some embodiments, the cycloaddition reaction and/or release of carbon monoxide occurs at a temperature of about 37° C. and pH of about 7.4.

II. Definitions

As used herein, the term "generating" refers to the formation or release or production of carbon monoxide in a surrounding environment.

As used herein, the term "carbon monoxide" refers to $:\overset{..}{\text{C}}{\equiv}\overset{..}{\text{O}}:$, $:\text{C}{=}\overset{..}{\text{O}}:$ as well as other forms of carbon monoxide formed under physiological conditions.

As used herein, the term "in vivo" refers to an environment inside of a living organism such as a human or other animal. In vivo can refer to the environment inside a living cell in the organism, or inside a bacterium, fungus, or virus in the organism.

As used herein, the term "ex vivo" refers to an environment outside of a living organism. For example, vivo can refer to a cell culture or a reaction mixture in a test tube.

As used herein, the term "administering" refers to oral, topical, parenteral, intravenous, intraperitoneal, intramuscular, intralesional, intranasal, subcutaneous, or intrathecal administration, as well as administration via suppository or via the implantation of a slow-release device e.g., a mini-osmotic pump, to a subject.

As used herein, the term "unsaturated molecule" refers to a molecule having a carbon-carbon double bond, a carbon-carbon triple bond, or both.

As used herein, the term "site of unsaturation" refers to a carbon-carbon double bond or a carbon-carbon triple bond.

As used herein, the term "diene" generally refers to a conjugated diene that participates in a Diels-Alder reaction. Dienes are characterized by two carbon-carbon double bonds separated by a carbon-carbon single bond (i.e., a moiety C=C—C=C that is unsubstituted or substituted as described herein).

As used herein, the term "dienophile" generally refers to an alkene or alkyne that participates in a Diels-Alder reaction via cycloaddition with a diene.

As used herein, the term "precursor molecule" refers to a molecule comprising a diene moiety and a dienophile moiety, as described above, which undergoes intramolecular cyclization to release CO. Precursor molecules of interest include, but are not limited to, scheme 2 (precursor 9), scheme 3 (precursor 15) and scheme 11 (precursor 12).

As used herein, the term "intramolecular cyclization" refers to the reaction of the diene moiety of a precursor molecule with the dienophile moiety of the same precursor molecule leading to formation of a cyclic structure with release of carbon monoxide.

As used herein, the term "cycloaddition reaction", refers to a pericyclic chemical reaction, in which two or more unsaturated molecules or two unsaturated moieties within one molecule combine to form a cyclic adduct in which there is a net reduction of the bond multiplicity.

As used herein, the terms "inverse electron demand Diels-Alder reaction" and "DARinv" are used interchangeably and refer to an organic chemical reaction, in which two new chemical bonds and a six-membered ring are formed. It is related to the Diels-Alder (DA) reaction, but unlike the DA reaction, the DARinv is a cycloaddition between an electron-rich dienophile and an electron-poor diene. During a DARinv reaction, three pi-bonds are broken, and two sigma bonds and one new pi-bond are formed.

As used herein, the term "effective amount" refers to an amount of carbon monoxide necessary to bring about a desired result. When "effective amount" is used to describe an in vivo method, the desired result can refer to a therapeutic effect. When "effective amount" is used to describe an ex vivo method the desired results can refer to a detectable level of carbon monoxide.

As used herein, the term "physiological conditions", refers to one or more of body temperature and pH. Body temperature is typically from about 33° C. to about 40° C., preferably from about 35° C. to about 38° C., such as about 37° C. Physiological pH is typically from about 6.8 to 8, preferably 6.8 to about 7.5, such as about 7.0. However, the pH may be lower or higher at specific sites and/or due to a particular disease state. For example, lower pH is often associated with diseased tissue such as tumor tissue As used herein, the term "composition" refers to a product comprising the specified ingredients in the specified amounts, as well as any product, which results, directly or indirectly, from combination of the specified ingredients in the specified amounts. By "pharmaceutically acceptable" it is meant that the carrier, diluent or excipient must be compatible with the other ingredients of the formulation and not deleterious to the recipient thereof.

As used herein, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

As used herein, the term "halogen" refers to fluorine, chlorine, bromine and iodine.

As used herein, the term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be unsubstituted or substituted with 1-6 $R^4$ groups as described below. The ranges provided above are inclusive of all values between the minimum value and the maximum value.

As used herein, the term "alkoxy" refers to an alkyl group having an oxygen atom that connects the alkyl group to the point of attachment: alkyl-O—. As for alkyl groups, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. Alkoxy groups can be unsubstituted or substituted with 1-6 $R^A$ groups as described below.

"Alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be unsubstituted or substituted with 1-6 $R^A$ groups as described below.

"Alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be unsubstituted or substituted with 1-6 $R^A$ groups as described below.

As used herein, the term "cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbomane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbomene, and norbomadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be unsubstituted or substituted with 1-6 $R^A$ groups as described below.

As used herein, the term "aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be unsubstituted or substituted with 1-6 $R^4$ groups as described below.

As used herein, the term "aryloxy", refers to a substituted or unsubstituted aryl-O— group, wherein aryl is as defined above. For example, the term "phenoxy" refers to an aryloxy group wherein the aryl moiety is a phenyl ring.

As used herein the term "heterocycle," by itself or as part of another substituent, refers to heteroaryl and heterocycloalkyl groups. In general, the carborane compounds of the invention contain at least one heterocycle having at least one nitrogen atom. "Heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can also be oxidized, such as, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be unsubstituted or substituted with 1-6 $R^4$ groups as described below.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

"Heterocycloalkyl" refers to a saturated ring system having from 3 to 12 ring members and from 1 to 4 heteroatoms of N, O and S. Additional heteroatoms can also be useful, including, but not limited to, B, Al, Si and P. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be unsubstituted or substituted with 1-6 $R^4$ groups as described below.

The heterocycloalkyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxzoalidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

The groups defined above can optionally be substituted by any suitable number and type of substituents. In some embodiments, the groups described above are substituted with from 1-6 $R^A$ groups, wherein $R^A$ is selected from the group consisting of cyano, halogen, haloalkyl, haloalkoxy, —OR', =O, —OC(O)R', —(O)R', —O$_2$R', —ONR'R", —OC(O)NR'R", =NR', =N—OR', —NR'R", —NR"C(O)R', —NR'—(O)NR"R'", —NR"C(O)OR', —NH—(NH$_2$)=NH, —NR'C(NH$_2$)=NH, —NH—(NH$_2$)=NR', —SR', —S(O)R', —S(O)$_2$R', —S(O)$_2$NR'R", —NR'S(O)$_2$R", —N$_3$ and —NO$_2$. R', R" and R'" each independently refer to hydrogen and unsubstituted alkyl, such as unsubstituted C$_{1-6}$ alkyl. Alternatively, R' and R", or R" and R'", when attached to the same nitrogen, are combined with the nitrogen to which they are attached to form a heterocycloalkyl or heteroaryl ring, as defined above.

As used herein, the term "alkylaryl", refers to an alkyl group substituted with an aryl group (e.g., an aromatic or hetero aromatic group).

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

As used herein, the term "biocompatible" refers to a reaction or reaction products that provide an intended (or otherwise appropriate) host response in a specific application, such as a therapeutic application. For example, a biocompatible cycloaddition reaction does not have toxic or injurious effects on biological systems.

As used herein, the term "functionalized molecule" refers to a molecule having one or more targeting moieties, solubilizing moieties, or linking moieties as described herein.

As used herein, the term "targeting moiety" refers to any moiety that targets a particular cell type. Targeting moieties include, but are not limited to, the group consisting of a ligand, carbohydrate, antibody, protein, enzyme, nucleic acid, drug or combinations thereof. In some embodiments, the targeting molecule is a folate. In some embodiments, the targeting molecule is a peptide such as an RGD peptide or a peptidomimetic compound.

Cell-targeting moieties can target a cell by interacting with, or binding to, cell-surface receptors or other molecules on the cell surface. Cell-targeting moieties can target a cell by interacting with, or binding to, disease-specific biomarkers. Such biomarkers belong to any condition or disease, and include, but are not limited to, biological molecules such as proteins, peptides, lipids, RNAs, DNA and variations and modifications thereof. Biomarkers may be circulating or localized. In some embodiments, the targeting molecule targets a disease-associated biomarker. In some embodiments, the biomarker is a cancer-associated biomarker. In some embodiments, the biomarker is prostate-specific membrane antigen (PSMA).

As used herein, the term "linking moiety" refers to any moiety which links a diene moiety, a dienophile moiety, or other moiety to a compound (i.e., an unsaturated molecule or a prescursor molecule as described herein) used in the methods and composition of the invention. In some embodiments, the "linking moiety" comprises a glycol linker, such as an ethylene glycol linker. In some embodiments, the "linking moiety" comprises a polyglycol linker, such as a poly(ethylene glycol) linker.

As used herein, the terms "solubility-enhancing moiety" and "solubilizing moiety" refer to a moiety used to increase solubility of a diene, a dienophile or a precursor molecule in a solvent. In some embodiments, the solubility-enhancing moiety comprises a sugar such as a monosaccharide, a disaccharide, an oligosaccharide, or a polysaccharide.

As used herein, the term "peptidomimetic" refers to a compound containing non-peptidic structural elements that is capable of mimicking or antagonizing the biological action(s) of a natural parent peptide.

As used herein, the term "antibody" refers to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). The term "antibody" also includes antigen binding forms of antibodies, including fragments with antigen-binding capability (e.g., Fab', F(ab')$_2$, Fab, Fv and rIgG. See also, Pierce Catalog and Handbook, 1994-1995 (Pierce Chemical Co., Rockford, Ill.). See also, e.g., Kuby, J., *Immunology*, 3$^{rd}$ Ed., W.H. Freeman & Co., New York (1998). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992) *J Immunol* 148:1547, Pack and Pluckthun (1992) *Biochemistry* 31:1579, Hollinger et al., 1993, supra, Gruber et al. (1994) *J Immunol:* 5368, Zhu et al. (1997) *Protein Sci* 6:781, Hu et al. (1996) *Cancer Res.* 56:3055, Adams et al. (1993) *Cancer Res.* 53:4026, and McCartney, et al. (1995) *Protein Eng.* 8:301.

As used herein, the term "enzyme" refers to a protein that catalyzes a chemical reaction. Enzymes can be endogenous or exogenous proteins. Enzymes include, but are not limited to, hydrolases, esterases, phosphatases, glycosidases, oxidases, reductases, lipases, transferases, polymerases and ligases. In some embodiments, the enzyme is a hydrolase. In some embodiments, the enzyme is an esterase. In some embodiments, the enzyme is a glycosidase. In some embodiments, the enzyme is a phosphatase.

Compounds of the present invention include all tautomers and stereoisomers thereof, either in admixture or in pure or substantially pure form. The compounds of the present invention can have asymmetric centers at the carbon atoms, and therefore the compounds of the present invention can exist in diastereomeric or enantiomeric forms or mixtures thereof. All conformational isomers (e.g., cis and trans isomers) and all optical isomers (e.g., enantiomers and diastereomers), racemic, diastereomeric and other mixtures of such isomers, as well as solvates, hydrates, isomorphs, polymorphs and tautomers are within the scope of the present invention. Compounds according to the present invention can be prepared using diastereomers, enantiomers or racemic mixtures as starting materials. Furthermore, diastereomer and enantiomer products can be separated by chromatography, fractional crystallization or other methods known to those of skill in the art.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Compounds of the invention also include isotopically-labeled compounds, wherein one or more atoms are replaced by one or more atoms having specific atomic mass or mass numbers. Examples of isotopes that can be incorporated into compounds of the invention include, but are not limited to, isotopes of hydrogen, carbon, nitrogen, oxygen, fluorine, sulfur, and chlorine (such as $^{2}H$, $^{3}H$, $^{13}C$, $^{14}C$, $^{15}N$, $^{18}O$, $^{17}O$, $^{18}F$, $^{35}S$ and $^{36}Cl$).

As used herein, the term "salt" refers to acid or base salts of the compounds of the invention. Illustrative examples of pharmaceutically acceptable salts include mineral acid salts (salts of hydrochloric acid, hydrobromic acid, phosphoric acid, and the like), organic acid salts (salts of acetic acid, propionic acid, glutamic acid, citric acid and the like) salts, and quaternary ammonium salts (salts of methyl iodide, ethyl iodide, and the like). It is understood that the pharmaceutically acceptable salts are non-toxic. Additional information on suitable pharmaceutically acceptable salts can be found in *Remington: The Science & Practice of Pharmacy*, 20th ed., Lippincott Williams & Wilkins, Philadelphia, Pa., 2000, which is incorporated herein by reference.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As used herein, the term "composition" is intended to encompass a product comprising the specified ingredients in the specified amounts, as well as any product, which results, directly or indirectly, from combination of the specified ingredients in the specified amounts. By "pharmaceutically acceptable" it is meant that the carrier, diluent or excipient must be compatible with the other ingredients of the formulation and not deleterious to the recipient thereof.

As used herein, the terms "treat", "treating" and "treatment" refer to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom. The treatment or amelioration of symptoms can be based on any objective or subjective parameter, including, e.g., the result of a physical examination.

III. Carbon Monoxide (CO)-Releasing Molecules

Carbon monoxide-releasing organic molecules are described herein. The molecules can be synthesized prior to administration (ex vivo) or formed after administration to a subject (in vivo). In those embodiments where the molecules are formed in vivo, reactants are administered under physiological conditions and undergo DARinv or intramolecular DARinv to form a product which releases carbon monoxide as and, in some cases, release a fluorophore in some cases. In applying such reactions for therapeutic applications in vivo, the cycloaddition and CO release should occur under near-physiological or physiological conditions. For example, in some embodiments, the cycloaddition (e.g., Diels-Alder) reaction and/or release of carbon monoxide occur at a temperature of about 37° C. and pH of about 7.4.

The present invention provides methods for generating carbon monoxide as described above, wherein the method includes combining the first unsaturated molecule and the second unsaturated molecule and allowing the unsaturated molecules to react to form the organic molecule that releases an effective amount of carbon monoxide under physiological conditions. In some such embodiments, the first unsaturated molecule is a diene and the second unsaturated molecule is a dienophile.

A. Dienes

In some embodiments, the diene has a structure according to Formula I:

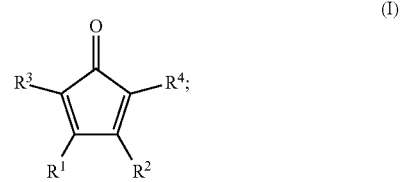

(I)

or a pharmaceutically acceptable salt thereof, wherein:
each $R^1$, $R^2$, $R^3$, and $R^4$ is independently selected from the group consisting of hydrogen, halogen, alkyl, cycloalkyl, heterocycloalkyl, alkenyl, alkynyl, aryl, heteroaryl, alkoxy, aryloxy, hydroxyl, —N(R$^a$)$_2$, —SR$^a$, —S(O)R$^a$, —S(O)$_2$R$^a$, —OS(O)OR$^a$, —OS(O)$_2$OR$^a$, —OP(OR$^a$)$_2$, —OP(O)HOR$^a$, —OP(O)(OR$^a$)$_2$, —OP(O)(R$^a$)$_2$, —P(O)(OR$^a$)$_2$, —ONO, —ONO$_2$, —NO$_2$, —(C=O)R$^5$, —(C=O)OR$^6$, —(C=O)NR$^7$R$^8$, a linking moiety R$^L$, a targeting moiety R$^T$, and a solubility-enhancing moiety R$^S$;

or, alternatively, R$^1$ and R$^2$ are independently selected from the group consisting of cycloalkyl, heterocycloalkyl, aryl, and heteroaryl, and are taken together to form a fused tricyclic moiety which is optionally substituted with one or more R$^9$ moieties, wherein each R$^9$ is independently selected from the group consisting of halogen, alkyl, cycloalkyl, heterocycloalkyl, alkenyl, alkynyl, aryl, heteroaryl, alkoxy, aryloxy, hydroxyl, —N(R$^a$)$_2$, —SR$^a$, —S(O)R$^a$, —S(O)$_2$R$^a$, —OS(O)OR$^a$, —OS(O)$_2$OR$^a$, —OP(OR$^a$)$_2$, —OP(O)HOR$^a$, —OP(O)(OR$^a$)$_2$, —OP(O)(R$^a$)$_2$, —P(O)(OR$^a$)$_2$, —ONO, —ONO$_2$, —NO$_2$, —(C=O)R$^5$, —(C=O)OR$^6$, —(C=O)NR$^7$R$^8$, a linking moiety R$^L$, a targeting moiety R$^T$, and a solubility-enhancing moiety R$^S$;

each R$^5$, R$^6$, R$^7$, and R$^8$ is independently selected from the group consisting of hydrogen, alkyl, heteroalkyl, alkenyl, heteroalkenyl, alkynyl, heteroalkynyl, cycloalkyl, heterocycloalkyl, aryl, and heteroaryl; and R$^a$ is selected from the group consisting of H, alkyl, aryl, cycloalkyl, and heteroaryl.

In some embodiments, the cycloaddition reaction involves a diene. In particular embodiments, the diene is a dienone or diene-dione.

In some embodiments, the diene has a structure according to Formula I:

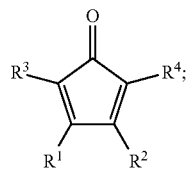

or a pharmaceutically acceptable salt thereof, wherein:

each R$^1$, R$^2$, R$^3$, and R$^4$ is independently selected from the group consisting of hydrogen, halogen, alkyl, cycloalkyl, heterocycloalkyl, alkenyl, alkynyl, aryl, heteroaryl, alkoxy, aryloxy, hydroxyl, —N(R$^a$)$_2$, —SR$^a$, —S(O)R$^a$, —S(O)$_2$R$^a$, —OS(O)OR$^a$, —OS(O)$_2$OR$^a$, —OP(OR$^a$)$_2$, —OP(O)HOR$^a$, —OP(O)(OR$^a$)$_2$, —OP(O)(R$^a$)$_2$, —P(O)(OR$^a$)$_2$, —ONO, —ONO$_2$, —NO$_2$, —(C=O)R$^5$, —(C=O)OR$^6$, —(C=O)NR$^7$R$^8$, a linking moiety R$^L$, a targeting moiety R$^T$, and a solubility-enhancing moiety R$^S$.

In some embodiments, each R$^1$, R$^2$, R$^3$, and R$^4$ is independently selected from the group consisting of hydrogen, halogen, alkyl, cycloalkyl, heterocycloalkyl, alkenyl, alkynyl, aryl, heteroaryl, alkoxy, and aryloxy.

In some embodiments, each R$^1$, R$^2$, R$^3$, and R$^4$ is independently selected from the group consisting of cycloalkyl, heterocycloalkyl, aryl, and heteroaryl.

In some embodiments, the diene is:

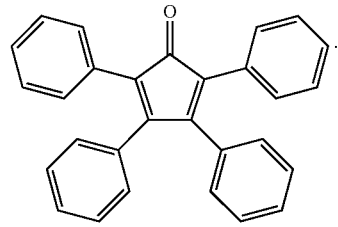 [SMILES: O=C1C(c2ccccc2)=C(c2ccccc2)C(c2ccccc2)=C1c1ccccc1]

In some embodiments, after the cycloaddition reaction, a fluorophore is also obtained along with carbon monoxide, which can allow for real-time monitoring of CO release. In some such embodiments, the diene has a fused polycyclic structure.

In some such embodiments, the diene is selected from the group consisting of Formula II and Formula III:

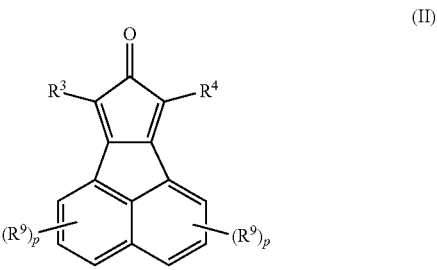

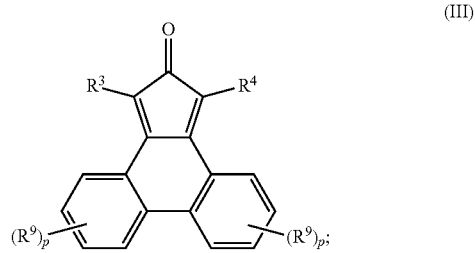

wherein each subscript p is independently selected from 0, 1, 2, or 3.

In some embodiments, each R$^3$ and R$^4$ is independently selected from the group consisting of hydrogen, halogen, alkyl, cycloalkyl, heterocycloalkyl, alkenyl, alkynyl, aryl, heteroaryl, alkoxy, and aryloxy.

In some embodiments, each R$^3$ and R$^4$ is independently selected from the group consisting of cycloalkyl, heterocycloalkyl, aryl, and heteroaryl.

In some embodiments, the diene is selected from the group consisting of:

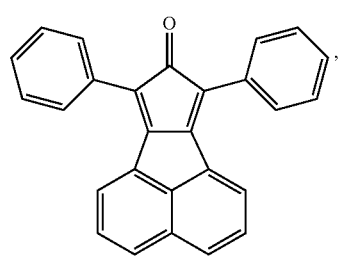

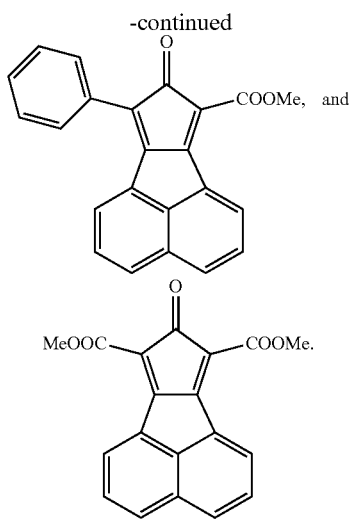

Diene-diones make up another class of dienes. These analogues possess two carbonyl groups, which can release CO more efficiently at the same concentration and time period compared to dienones.

In some embodiments, the diene has a diene-dione structure according to Formula IV:

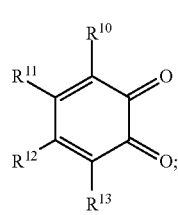

(IV)

or a pharmaceutically acceptable salt thereof, wherein:
each $R^{10}$, $R^{11}$, $R^{12}$ and $R^{13}$ is independently selected from the group consisting of hydrogen, halogen, alkyl, cycloalkyl, heterocycloalkyl, alkenyl, alkynyl, aryl, heteroaryl, alkoxy, aryloxy, hydroxyl, —N($R^a$)$_2$, —S$R^a$, —S(O)$R^a$, —S(O)$_2R^a$, —OS(O)O$R^a$, —OS(O)$_2$O$R^a$, —OP(O$R^a$)$_2$, —OP(O)HO$R^a$, —OP(O)(O$R^a$)$_2$, —OP(O)($R^a$)$_2$, —P(O)(O$R^a$)$_2$, —ONO, —ONO$_2$, —NO$_2$, —(C=O)$R^5$, —(C=O)O$R^6$, —(C=O)N$R^7R^8$, a linking moiety $R^L$, a targeting moiety $R^T$, and a solubility-enhancing moiety $R^S$;
$R^a$ is selected from the group consisting of hydrogen, alkyl, cycloalkyl, aryl or heteroaryl; and
each $R^5$, $R^6$, $R^7$, and $R^8$ is independently selected from the group consisting of hydrogen, alkyl, heteroalkyl, alkenyl, heteroalkenyl, alkynyl, heteroalkynyl, cycloalkyl, heterocycloalkyl, aryl, and heteroaryl.

In some embodiments, each $R^{10}$, $R^{11}$, $R^{12}$ and $R^{13}$ is independently selected from the group consisting of hydrogen, halogen, alkyl, cycloalkyl, heterocycloalkyl, alkenyl, alkynyl, aryl, heteroaryl, alkoxy, and aryloxy.

In some embodiments, wherein each $R^{10}$, $R^{11}$, $R^{12}$ and $R^{13}$ is independently selected from the group consisting of cycloalkyl, heterocycloalkyl, aryl, and heteroaryl.

Any functional groups can be introduced as substituents; however, no functional groups should be present which are reactive towards the dienophile (such as azido groups) as they can interfere with the DARinv.

In some embodiments, each $R^1$, $R^2$, $R^3$, and $R^4$ (or $R^{10}$, $R^{11}$, $R^{12}$ and $R^{13}$) is independently selected to increase the hydrophilicity of the diene and therefore the water-solubility. In some embodiments, each $R^1$, $R^2$, $R^3$, and $R^4$ is independently selected from hydroxyl-, amine-, and carboxylic acid groups, which can be tethered to diene molecules to improve the aqueous solubility of the diene.

In some embodiments, each $R^1$, $R^2$, $R^3$, and $R^4$ (or $R^{10}$, $R^{11}$, $R^{12}$ and $R^{13}$) is independently selected to couple or immobilize the diene to solid beads, polyethylene glycol and other soluble and insoluble polymers and macromolecules including proteins, nucleic acids, and carbohydrates to improve solubility of the molecules. This type of coupling can also reduce toxicity by preventing or reducing passage of the diene into cells.

In some embodiments, each $R^1$, $R^2$, $R^3$, and $R^4$ (or $R^{10}$, $R^{11}$, $R^{12}$ and $R^{13}$) is independently selected to couple to a targeting molecule such as folate, an RGD peptide, other ligands for cancer-associated biomarkers such as prostate specific membrane antigen (PSMA), and certain carbohydrates which can target cancer. Similar strategies can be used to target other diseases and pathological changes.

B. Dienophiles

In certain embodiments, the cycloaddition reaction involves a dienophile. Most Diels-Alder/CO-releasing reactions reported in the literature require high temperatures (e.g., 150° C.). In order to lower the reaction temperature, strained dienophiles can be used. Strained dienophiles refer to those with one or more double or triple bonds, which are bent due to ring strain. In some embodiments, a strained alkyne is used as the dienophile allowing the reaction to proceed at ambient or body temperature. The high molecular strain increases the HOMO energy of the dienophiles, which leads to a decrease in the LUMO diene-HOMOphile gap and consequently an increase in the reaction rate.

In some embodiments, the dienophile has a structure according to Formula V:

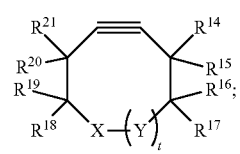

(V)

or a pharmaceutically acceptable salt thereof, wherein:
each $R^{14}$, $R^{15}$, $R^{16}$, $R^{17}$, $R^{18}$, $R^{19}$, $R^{20}$, and $R^{21}$ is independently selected from the group consisting of hydrogen, halogen, substituted or unsubstituted alkyl, cycloalkyl, heterocycloalkyl, alkenyl, alkynyl, aryl, heteroaryl, alkoxy, or aryloxy, hydroxyl, —N($R^a$)$_2$, —S$R^a$, —S(O)$R^a$, —S(O)$_2R^a$, —OS(O)O$R^a$, —OS(O)$_2$O$R^a$, —OP(O$R^a$)$_2$, —OP(O)HO$R^a$, —OP(O)(O$R^a$)$_2$, —OP(O)($R^a$)$_2$, —P(O)(O$R^a$)$_2$, —ONO, —ONO$_2$, —NO$_2$, —(C=O)$R^{5'}$, —(C=O)O$R^{6'}$, —(C=O)N$R^{7'}R^{8'}$, a linking moiety $R^L$, a targeting moiety $R^T$, and a solubility-enhancing moiety $R^S$;
each $R^{5'}$, $R^{6'}$, $R^{7'}$, and $R^{8'}$ is independently selected from the group consisting of hydrogen, alkyl, heteroalkyl, alkenyl, heteroalkenyl, alkynyl, heteroalkynyl, cycloalkyl, heterocycloalkyl, aryl, and heteroaryl;
$R^{14}$ or $R^{15}$ is optionally taken together with $R^{16}$ or $R^{17}$ to form fused cycloalkyl, fused heterocyclyl, fused aryl, or fused heteroaryl, each of which is optionally substituted with $R^{9'}$;

$R^{18}$ or $R^{19}$ is optionally taken together with $R^{20}$ or $R^{21}$ to form fused cycloalkyl, fused heterocyclyl, fused aryl, or fused heteroaryl, each of which is optionally substituted with $R^{9'}$;

each $R^{9'}$ is independently selected from the group consisting of halogen, alkyl, cycloalkyl, heterocycloalkyl, alkenyl, alkynyl, aryl, heteroaryl, alkoxy, aryloxy, hydroxyl, —N(R$^a$)$_2$, —SR$^a$, —S(O)R$^a$, —S(O)$_2$R$^a$, —OS(O)OR$^a$, —OS(O)$_2$OR$^a$, —OP(OR$^a$)$_2$, —OP(O)HOR$^a$, —OP(O)(OR$^a$)$_2$, —OP(O)(R$^a$)$_2$, —P(O)(OR$^a$)$_2$, —ONO, —ONO$_2$, —NO$_2$, —(C=O)R$^{5'}$, —(C=O)OR$^{6'}$, —(C=O)NR$^{7'}$R$^{8'}$, a linking moiety $R^L$, a targeting moiety $R^T$, and a solubility-enhancing moiety $R^S$;

Y is selected from the group consisting of CR$^{22a}$R$^{22b}$, S, O, and NR$^a$;

X is selected from the group consisting of CR$^{23a}$R$^{23b}$, S, O, and NR$^a$;

wherein each $R^{22a}$, $R^{22b}$, $R^{23a}$, and $R^{23b}$ is defined as for $R^{5'}$;

wherein $R^{22a}$ or $R^{22b}$ is optionally taken together with $R^{23a}$ or $R^{23b}$ to form a cyclic moiety optionally substituted with $R^{9'}$;

$R^a$ is selected from the group consisting of hydrogen, alkyl, cycloalkyl, aryl and heteroaryl; and subscript t is 0 or 1.

In some embodiments, the dienophile has a structure according to Formula Va:

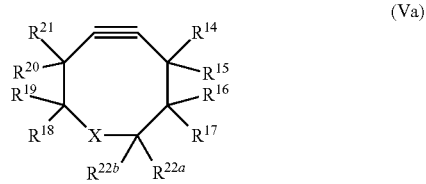

(Va)

or a pharmaceutically acceptable salt thereof, wherein:

each $R^{14}$, $R^{15}$, $R^{16}$, $R^{17}$, $R^{18}$, $R^{19}$, $R^{20}$, and $R^{21}$ is independently selected from the group consisting of hydrogen, halogen, substituted or unsubstituted alkyl, cycloalkyl, heterocycloalkyl, alkenyl, alkynyl, aryl, heteroaryl, alkoxy, or aryloxy, hydroxyl, —N(R$^a$)$_2$, —SR$^a$, —S(O)R$^a$, —S(O)$_2$R$^a$, —OS(O)OR$^a$, —OS(O)$_2$OR$^a$, —OP(OR$^a$)$_2$, —OP(O)HOR$^a$, —OP(O)(OR$^a$)$_2$, —OP(O)(R$^a$)$_2$, —P(O)(OR$^a$)$_2$, —ONO, —ONO$_2$, —NO$_2$, —(C=O)R$^{5'}$, —(C=O)OR$^{6'}$, —(C=O)NR$^{7'}$R$^{8'}$, a linking moiety $R^L$, a targeting moiety $R^T$, and a solubility-enhancing moiety $R^S$; and X is selected from the group consisting of CR$^{23a}$R$^{23b}$, S, O, and NR$^a$.

In some embodiments, each $R^{14}$, $R^{15}$, $R^{16}$, $R^{17}$, $R^{18}$, $R^{19}$, $R^{20}$, $R^{21}$, $R^{22a}$, and $R^{22b}$ is independently selected from the group consisting of hydrogen, halogen, substituted or unsubstituted alkyl, alkoxy, hydroxyl, —(C=O)R$^{5'}$, —(C=O)OR$^{6'}$, —(C=O)NR$^{7'}$R$^{8'}$, a linking moiety $R^L$, a targeting moiety $R^T$, and a solubility-enhancing moiety $R^S$.

In some embodiments, each $R^{14}$, $R^{15}$, $R^{16}$, $R^{17}$, $R^{18}$, $R^{19}$, $R^{20}$, $R^{21}$, $R^{22a}$, and $R^{22b}$ is independently selected from the group consisting of hydrogen, halogen, —(C=O)OR$^{6'}$, a linking moiety $R^L$, a targeting moiety $R^T$, and a solubility-enhancing moiety $R^S$.

In some embodiments, wherein the dienophile is selected from the group consisting of:

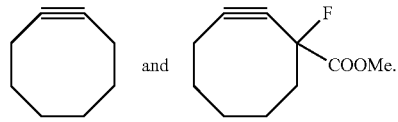

In some embodiments, wherein the dienophile has a structure according to Formula VI:

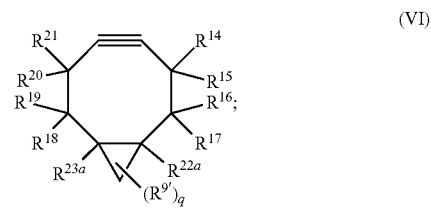

(VI)

or a pharmaceutically acceptable salt thereof, wherein
each $R^{14}$, $R^{15}$, $R^{16}$, $R^{17}$, $R^{18}$, $R^{19}$, $R^{20}$, and $R^{21}$ is independently selected from the group consisting of hydrogen, halogen, substituted or unsubstituted alkyl, cycloalkyl, heterocycloalkyl, alkenyl, alkynyl, aryl, heteroaryl, alkoxy, or aryloxy, hydroxyl, —N(R$^a$)$_2$, —SR$^a$, —S(O)R$^a$, —S(O)$_2$R$^a$, —OS(O)OR$^a$, —OS(O)$_2$OR$^a$, —OP(OR$^a$)$_2$, —OP(O)HOR$^a$, —OP(O)(OR$^a$)$_2$, —OP(O)(R$^a$)$_2$, —P(O)(OR$^a$)$_2$, —ONO, —ONO$_2$, —NO$_2$, —(C=O)R$^{5'}$, —(C=O)OR$^{6'}$, —(C=O)NR$^{7'}$R$^{8'}$, a linking moiety $R^L$, a targeting moiety $R^T$, and a solubility-enhancing moiety $R^S$; and wherein subscript q is 0, 1, or 2.

In some embodiments, each $R^{14}$, $R^{15}$, $R^{16}$, $R^{17}$, $R^{18}$, $R^{19}$, $R^{20}$, $R^{21}$, $R^{22a}$, and $R^{23a}$ is independently selected from the group consisting of hydrogen, halogen, substituted or unsubstituted alkyl, alkoxy, hydroxyl, —(C=O)R$^{5'}$, —(C=O)OR$^{6'}$, —(C=O)NR$^{7'}$R$^{8'}$, a linking moiety $R^L$, a targeting moiety $R^T$, and a solubility-enhancing moiety $R^S$.

In some embodiments, each $R^{14}$, $R^{15}$, $R^{16}$, $R^{17}$, $R^{18}$, $R^{19}$, $R^{20}$, $R^{21}$, $R^{22a}$, and $R^{23a}$ is independently selected from the group consisting of hydrogen, halogen, —(C=O)OR$^{6'}$, a linking moiety $R^L$, a targeting moiety $R^T$, and a solubility-enhancing moiety $R^S$.

In some embodiments, the dienophile is:

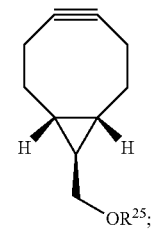

wherein $R^{25}$ is selected from the group consisting of hydrogen, substituted or unsubstituted alkyl, cycloalkyl, heterocycloalkyl, alkenyl, alkynyl, aryl, heteroaryl, a linking moiety $R^L$, a targeting moiety $R^T$, and a solubility-enhancing moiety $R^S$.

In some embodiments, the dienophile has a structure according to Formula VII:

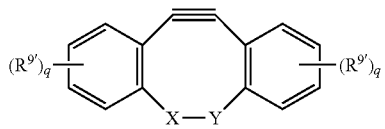

(VII)

or a pharmaceutically acceptable salt thereof, wherein
Y is selected from the group consisting of $CR^{22a}R^{22b}$, S, O, and $NR^a$;
X is selected from the group consisting of $CR^{23a}R^{23b}$, S, O, and $NR^a$; and
each subscript q is independently 0, 1, 2, 3, or 4.

In some embodiments, each $R^{22a}$, $R^{22b}$, $R^{23a}$, and $R^{23b}$ is independently selected from the group consisting of of hydrogen, halogen, substituted or unsubstituted alkyl, alkoxy, hydroxyl, —(C=O)$R^{5'}$, —(C=O)$OR^{6'}$, —(C=O)$NR^{7'}R^{8'}$, a linking moiety $R^L$, a targeting moiety $R^T$, and a solubility-enhancing moiety $R^S$.

In some embodiments, each $R^{22a}$, $R^{22b}$, $R^{23a}$, and $R^{23b}$ is independently selected from the group consisting of hydrogen, halogen, —(C=O)$OR^{6'}$, a linking moiety $R^L$, a targeting moiety $R^T$, and a solubility-enhancing moiety $R^S$.

In some embodiments, the dienophile has a structure according to Formula VIII:

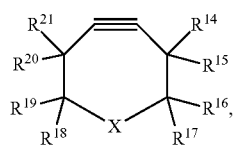

(VIII)

or a pharmaceutically acceptable salt thereof, wherein
each of $R^{14}$, $R^{15}$, $R^{16}$, $R^{17}$, $R^{18}$, $R^{19}$, $R^{20}$, and $R^{21}$ is independently selected from the group consisting of hydrogen, halogen, substituted or unsubstituted alkyl, cycloalkyl, heterocycloalkyl, alkenyl, alkynyl, aryl, heteroaryl, alkoxy, or aryloxy, hydroxyl, —N($R^a$)$_2$, —S$R^a$, —S(O)$R^a$, —S(O)$_2R^a$, —OS(O)$OR^a$, —OS(O)$_2OR^a$, —OP(O$R^a$)$_2$, —OP(O)H$OR^a$, —OP(O)(O$R^a$)$_2$, —OP(O)($R^a$)$_2$, —P(O)(O$R^a$)$_2$, —ONO, —ONO$_2$, —NO$_2$, —(C=O)$R^{5'}$, —(C=O)$OR^{6'}$, —(C=O)$NR^{7'}R^{8'}$, a linking moiety $R^L$, a targeting moiety $R^T$, and a solubility-enhancing moiety $R^S$; and
X is selected from the group consisting of $CR^{23a}R^{23b}$, S, O, and $N^R$.

Any functional groups can be introduced as substituents; however, no functional groups should be present which is reactive towards the diene.

In some embodiments, each $R^{14}$, $R^{15}$, $R^{16}$, $R^{17}$, $R^{18}$, $R^{19}$, $R^{20}$, $R^{21}$, $R^{22a}$, $R^{22b}$, $R^{23a}$, $R^{23b}$, $R^{25}$, and $R^{9'}$ is independently selected to increase the hydrophilicity of the dienophile and therefore the water-solubility. In some embodiments, each $R^{14}$, $R^{15}$, $R^{16}$, $R^{17}$, $R^{18}$, $R^{19}$, $R^{20}$, $R^{21}$, $R^{22a}$, $R^{22b}$, $R^{23a}$, $R^{23b}$, $R^{25}$, and $R^{9'}$ is independently selected to contain hydroxyl-, amine-, and carboxylic acid groups, which can be tethered to diene molecules to improve the aqueous solubility of the diene.

In some embodiments, each $R^{14}$, $R^{15}$, $R^{16}$, $R^{17}$, $R^{18}$, $R^{19}$, $R^{20}$, $R^{21}$, $R^{22a}$, $R^{22b}$, $R^{23a}$, $R^{23b}$, $R^{25}$, and $R^{9'}$ is independently selected to couple or immobilize the diene to solid beads, polyethylene glycol and other soluble and insoluble polymers and macromolecules including proteins, nucleic acids, and carbohydrates to improve solubility of the molecules and/or reduce toxicity by preventing or reducing passage of the diene into cells.

In some embodiments, each $R^{14}$, $R^{15}$, $R^{16}$, $R^{17}$, $R^{18}$, $R^{19}$, $R^{20}$, $R^{21}$, $R^{22a}$, $R^{22b}$, $R^{23a}$, $R^{23b}$, $R^{25}$, and $R^{9'}$ is independently selected to couple to a targeting molecule such as folate, an RGD peptide, other ligands for cancer-associated biomarkers such as prostate specific membrane antigen (PSMA), and certain carbohydrates which can target cancer. Similar strategies can be used to target other diseases and pathological changes.

In some embodiments, the carbon monoxide is generated in vivo.

In some embodiments, generating carbon monoxide in vivo comprises administering the first unsaturated molecule and the second unsaturated molecule to a subject in need thereof.

C. Intramolecular DARinv

In some embodiments, the dienes and dienophiles are present in a unimolecular CO releasing molecule which is stable in storage and in organic solvents. However, in an aqueous solution (e.g. physiological conditions), the hydrophobicity of the dienophile moiety can bring it in proximity with the diene moiety in a folded conformation to offer a significant entropic advantage for the cycloaddition. It is well known that entropic factors can significantly accelerate reactions by orders of magnitude of up to $10^{13}$, and thus account for the reaction rate difference between organic and aqueous solutions.

In some embodiments, the precursor molecule (i.e., the unimolecular CO releasing molecule) has a structure according to Formula IX:

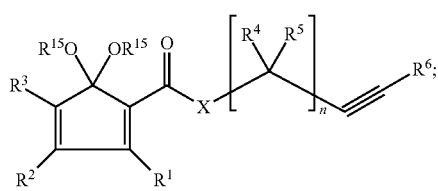

(IX)

or a pharmaceutically acceptable salt thereof, wherein:
each $R^1$, $R^2$, $R^3$, $R^4$, $R^5$, and $R^6$ is independently selected from the group consisting of hydrogen, halogen, substituted or unsubstituted alkyl, cycloalkyl, heterocycloalkyl, alkenyl, alkynyl, aryl, heteroaryl, alkoxy, aryloxy, hydroxyl, —N($R^a$)$_2$, —S$R^a$, —S(O)$R^a$, —S(O)$_2R^a$, —OS(O)$OR^a$, —OS(O)$_2OR^a$, —OP(O$R^a$)$_2$, —OP(O)H$OR^a$, —OP(O)(O$R^a$)$_2$, —OP(O)($R^a$)$_2$, —P(O)(O$R^a$)$_2$, —ONO, —ONO$_2$, —NO$_2$, —(C=O)$R^7$, —(C=O)$R^8$, —(C=O)$NR^9R^{10}$, a protecting moiety $R^P$, a linking moiety $R^L$, a targeting moiety $R^T$, and a solubility-enhancing moiety $R^S$;
or, alternatively, $R^1$ and $R^2$ are independently selected from the group consisting of cycloalkyl, heterocycloalkyl, aryl, and heteroaryl, and are taken together to form a fused tricyclic moiety which is optionally substituted with one or more $R^{11}$ moieties, wherein
each $R^{11}$ is independently selected from the group consisting of halogen, alkyl, cycloalkyl, heterocycloalkyl, alkenyl, alkynyl, aryl, heteroaryl, alkoxy, aryloxy, hydroxyl, —N($R^a$)$_2$, —S$R^a$, —S(O)$R^a$, —S(O)$_2R^a$, —OS(O)OR$^a$, —OS(O)$_2$OR$^a$, —OP(OR$^a$)$_2$, —OP(O)HOR$^a$, —OP(O)(OR$^a$)$_2$, —OP(O)(R$^a$)$_2$, —P(O)(OR$^a$)$_2$, —ONO, —ONO$_2$, —NO$_2$, —(C═O)R$^5$, —(C═O)OR$^6$, —(C═O)NR$^7$R$^8$, a linking moiety R$^L$, a targeting moiety R$^T$, and a solubility-enhancing moiety R$^S$;

R$^a$ is selected from the group consisting of hydrogen, alkyl, cycloalkyl, aryl or heteroaryl;

each R$^7$, R$^8$, R$^9$, and R$^{10}$ is independently selected from the group consisting of hydrogen, alkyl, heteroalkyl, alkenyl, heteroalkenyl, alkynyl, heteroalkynyl, cycloalkyl, heterocycloalkyl, aryl, and heteroaryl;

X is CR$^{12}$R$^{13}$, S, O, or NR$^{14}$, wherein each R$^{12}$ and R$^{13}$ is defined as for R$^1$, and R$^{14}$ is defined as for R$^7$;

each R$^{15}$ is independently selected from the group consisting of hydrogen, alkyl, cycloalkyl, heterocycloalkyl, alkenyl, alkynyl, aryl, and heteroaryl, or, alternatively two OR$^{15}$ are taken together to form an oxo moiety; and subscript n is 1, 2 or 3.

In some embodiments, the precursor molecule has a structure according to Formula IXa:

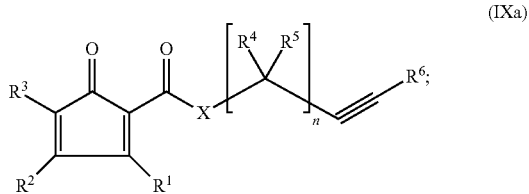

(IXa)

or a pharmaceutically acceptable salt thereof, wherein:

each R$^1$, R$^2$, R$^3$, R$^4$, R$^5$, and R$^6$ is independently selected from the group consisting of hydrogen, halogen, substituted or unsubstituted alkyl, cycloalkyl, heterocycloalkyl, alkenyl, alkynyl, aryl, heteroaryl, alkoxy, aryloxy, hydroxyl, —N(R$^a$)$_2$, —SR$^a$, —S(O)R$^a$, —S(O)$_2$R$^a$, —OS(O)OR$^a$, —OS(O)$_2$OR$^a$, —OP(OR$^a$)$_2$, —OP(O)HOR$^a$, —OP(O)(OR$^a$)$_2$, —OP(O)(R$^a$)$_2$, —P(O)(OR$^a$)$_2$, —ONO, —ONO$_2$, —NO$_2$, —(C═O)R$^7$, —(C═O)OR$^8$, —(C═O)NR$^9$R$^{10}$, a protecting moiety R$^P$, a linking moiety R$^L$, a targeting moiety R$^T$, and a solubility-enhancing moiety R$^S$.

In some embodiments, each R$^1$ and R$^2$ is independently selected from the group consisting of hydrogen, halogen, alkyl, cycloalkyl, heterocycloalkyl, alkenyl, alkynyl, aryl, heteroaryl, alkoxy, and aryloxy.

In some embodiments, each R$^1$ and R$^2$ is independently independently selected from the group consisting of cycloalkyl, heterocycloalkyl, aryl, and heteroaryl.

In some embodiments, the precursor molecule has a structure selected from the group consisting of Formula X and Formula XI:

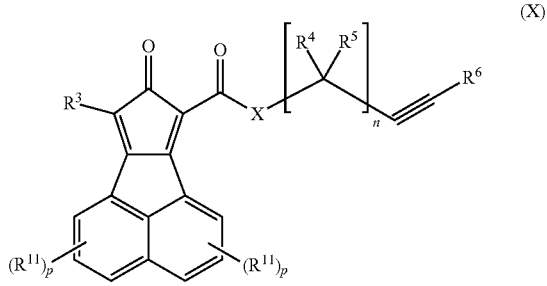

(X)

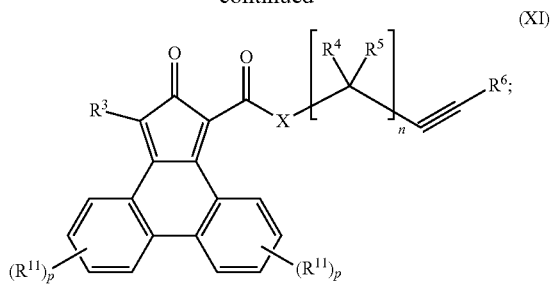

(XI)

or a pharmaceutically acceptable salt thereof, wherein each subscript p is independently 0, 1, 2, or 3.

The carbonyl group in a dienone can be masked by a ketal, which makes the diene unreactive to the alkyne or other dienophile. In the presence of stimuli like acidic conditions (pH 1-2) or esterase activity, the masked carbonyl group is unmasked and followed by the intramolecular DARinv to release carbon monoxide. In some embodiments, the precursor molecule has a structure selected from the group consisting of Formula XII and XIII:

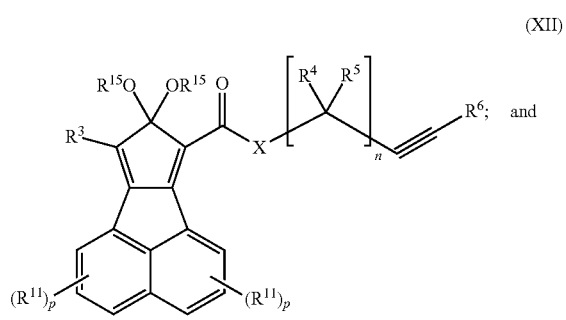

(XII)

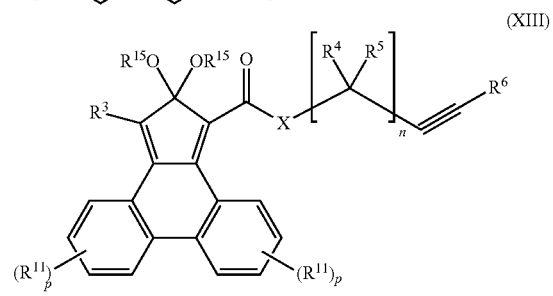

(XIII)

or a pharmaceutically acceptable salt thereof, wherein:

each R$^{15}$ is independently selected from the group consisting of hydrogen, alkyl, cycloalkyl, heterocycloalkyl, alkenyl, alkynyl, aryl, and heteroaryl; and each subscript p is independently selected from 0, 1, 2, and 3.

In some embodiments, R$^3$ is selected from the group consisting of hydrogen, halogen, alkyl, cycloalkyl, heterocycloalkyl, alkenyl, alkynyl, aryl, heteroaryl, alkoxy, and aryloxy.

In some embodiments, R$^3$ is selected from the group consisting of cycloalkyl, heterocycloalkyl, aryl, and heteroaryl.

In some embodiments, X is NR$^{14}$ and R$^{14}$ is selected from the group consisting of hydrogen, alkyl, and heteroalkyl.

In some embodiments, R$^3$ is selected from the group consisting of cycloalkyl, heterocycloalkyl, aryl, and heteroaryl.

In some embodiments, R⁴ and R⁵ are hydrogen.
In some embodiments, subscript n is 1 or 2.
In some embodiments, the precursor molecule is selected from the the group consisting of:

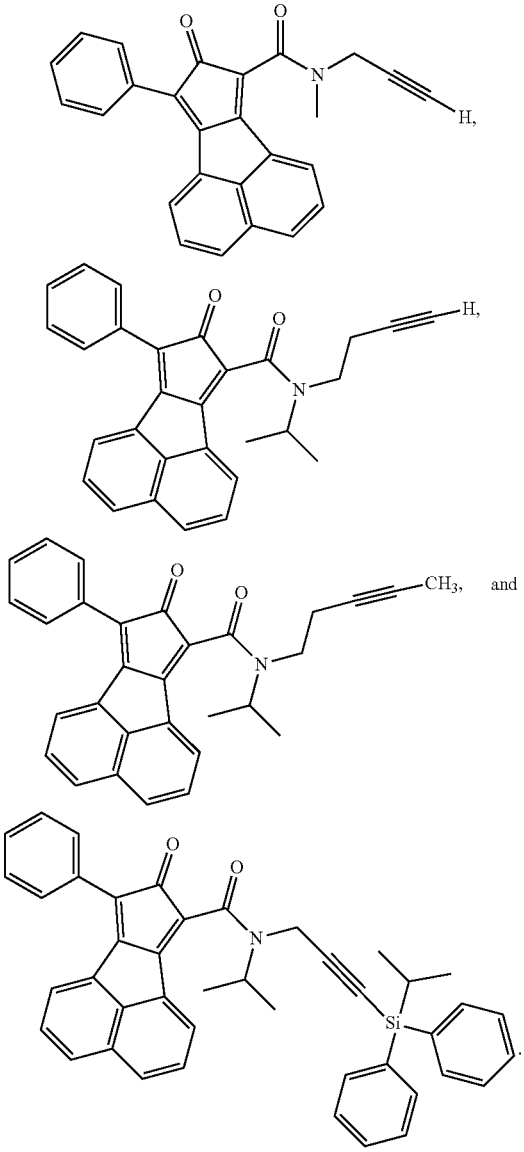

In some embodiments, the precursor molecule has a structure according to Formula XII:

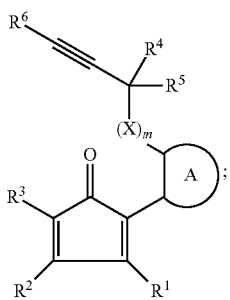

(XIV)

or a pharmaceutically acceptable salt thereof, wherein:

each $R^1$, $R^2$, $R^3$, $R^4$, $R^5$, and $R^6$ is independently selected from the group consisting of hydrogen, halogen, substituted or unsubstituted alkyl, cycloalkyl, heterocycloalkyl, alkenyl, alkynyl, aryl, heteroaryl, alkoxy, aryloxy, hydroxyl, —N(R$^a$)$_2$, —SR$^a$, —S(O)R$^a$, —S(O)$_2$R$^a$, —OS(O)OR$^a$, —OS(O)$_2$OR$^a$, —OP(OR$^a$)$_2$, —OP(O)HOR$^a$, —OP(O)(OR$^a$)$_2$, —OP(O)(R$^a$)$_2$, —P(O)(OR$^a$)$_2$, —ONO, —ONO$_2$, —NO$_2$, —(C=O)R$^7$, —(C=O)OR$^8$, —(C=O)NR$^9$R$^{10}$, a protecting moiety $R^P$, a linking moiety $R^L$, a targeting moiety $R^T$, and a solubility-enhancing moiety $R^S$;

or, alternatively, $R^1$ and $R^2$ are independently selected from the group consisting of cycloalkyl, heterocycloalkyl, aryl, and heteroaryl, and are taken together to form a fused tricyclic moiety which is optionally substituted with one or more $R^{11}$ moieties, wherein each $R^{11}$ is selected from the group consisting of hydrogen, halogen, alkyl, cycloalkyl, heterocycloalkyl, alkenyl, alkynyl, aryl, heteroaryl, alkoxy, aryloxy, hydroxyl, —N(R$^a$)$_2$, —SR$^a$, —S(O)R$^a$, —S(O)$_2$R$^a$, —OS(O)OR$^a$, —OS(O)$_2$OR$^a$, —OP(OR$^a$)$_2$, —OP(O)H OR$^a$, —OP(O)(OR$^a$)$_2$, —OP(O)(R$^a$)$_2$, —P(O)(OR$^a$)$_2$, —ONO, —ONO$_2$, —NO$_2$, —(C=O)R$^5$, —(C=O)OR$^6$, —(C=O)NR$^7$R$^8$, a protecting moiety $R^P$, a linking moiety $R^L$, a targeting moiety $R^T$, and a solubility-enhancing moiety $R^S$;

$R^a$ is selected from the group consisting of hydrogen, alkyl, cycloalkyl, aryl or heteroaryl;

each $R^7$, $R^8$, $R^9$, and $R^{10}$ is independently selected from the group consisting of hydrogen, alkyl, heteroalkyl, alkenyl, heteroalkenyl, alkynyl, heteroalkynyl, cycloalkyl, heterocycloalkyl, aryl, and heteroaryl;

X is $CR^{12}R^{13}$, S, O, or $NR^{14}$, wherein each $R^{12}$ and $R^{13}$ is defined as for $R^1$, and $R^{14}$ is defined as for $R^7$;

"A" is selected from the group consisting of cycloalkyl, heterocycloalkyl, aryl, and heteroaryl; and subscript m is 1, 2 or 3, provided that only one of X is S or O when m is 2 or 3.

In some embodiments, each $R^1$, $R^2$, $R^3$, $R^4$, $R^5$, and $R^6$ is independently selected from the group consisting of hydrogen, halogen, substituted or unsubstituted alkyl, cycloalkyl, heterocycloalkyl, alkenyl, alkynyl, aryl, heteroaryl, alkoxy, aryloxy, hydroxyl, —N(R$^a$)$_2$, —SR$^a$, —S(O)R$^a$, —S(O)$_2$R$^a$, —OS(O)OR$^a$, —OS(O)$_2$OR$^a$, —OP(OR$^a$)$_2$, —OP(O)HOR$^a$, —OP(O)(OR$^a$)$_2$, —OP(O)(R$^a$)$_2$, —P(O)(OR$^a$)$_2$, —ONO, —ONO$_2$, —NO$_2$, —(C=O)R$^7$, —(C=O)OR$^8$, —(C=O)NR$^9$R$^{10}$, a protecting moiety $R^P$, a linking moiety $R^L$, a targeting moiety $R^T$, and a solubility-enhancing moiety $R^S$.

In some embodiments, $R^1$ and $R^2$ are independently selected from the group consisting of hydrogen, halogen, alkyl, cycloalkyl, heterocycloalkyl, alkenyl, alkynyl, aryl, heteroaryl, alkoxy, and aryloxy.

In some embodiments, $R^1$ and $R^2$ are independently selected from the group consisting of cycloalkyl, heterocycloalkyl, aryl, and heteroaryl.

In some embodiments, the precursor molecule has a structure selected from the group consisting of Formulae XV and XVI:

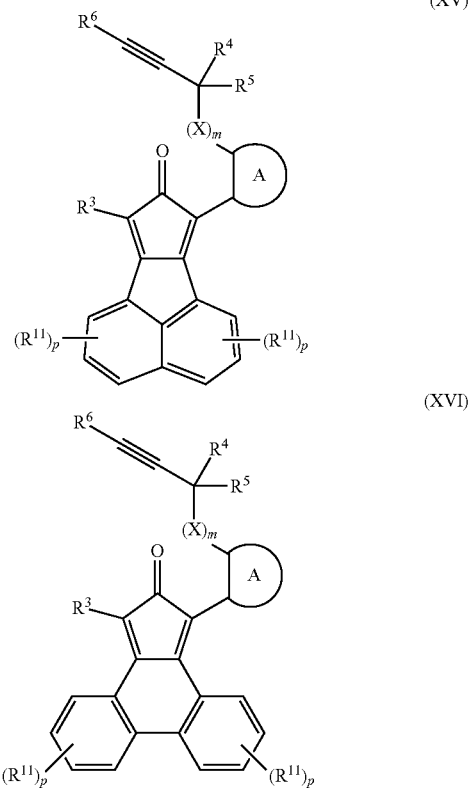

or a pharmaceutically acceptable salt thereof, wherein each subscript p is independently 0, 1, 2, or 3.

In some embodiments, $R^3$ is selected from the group consisting of heterocycloalkyl, heteroaryl, alkoxy, aryloxy, and hydroxyl. In some such embodiments, A is phenyl. In some embodiments, X is O or S.

In some embodiments, $R^3$ is selected from the group consisting of cycloalkyl, heterocycloalkyl, aryl, and heteroaryl. In some such embodiments, A is phenyl.

In some embodiments, the precursor molecule is:

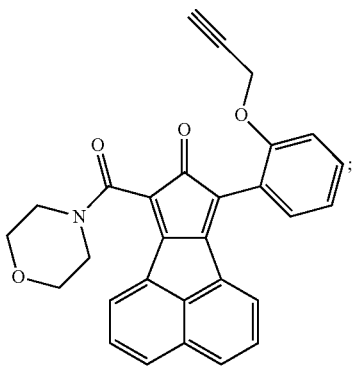 [SMILES: C#CCOc1ccccc1C1=C2C(=C(C(=O)N3CCOCC3)C1=O)c1cccc3cccc2c13]

or a pharmaceutically acceptable salt thereof.

Any functional groups can be introduced as substituents; however, no functional groups should be present which are reactive towards the dienophile as they can interfere with the DARinv. Examples include, but are not limited to, azido groups.

$R^1$-$R^6$ and $R^{11}$-$R^{14}$ can be selected to increase the hydrophilicity of the diene and therefore the water-solubility. In some embodiments, $R^1$-$R^4$ are independently selected to contain hydroxyl-, amine-, and carboxylic acid groups, which can be tethered to diene molecules to improve the aqueous solubility of the diene.

$R^1$-$R^6$ and $R^{11}$-$R^{14}$ can also be selected to couple or immobilize the diene to solid beads, polyethylene glycol and other soluble and insoluble polymers and macromolecules including proteins, nucleic acids, and carbohydrates to improve solubility of the molecules and/or reduce toxicity by preventing or reducing passage of the diene into cells.

$R^1$-$R^6$ and $R^{11}$-$R^{14}$ can also be selected to couple to a targeting molecule such as folate, an RGD peptide, other ligands for cancer-associated biomarkers such as prostate specific membrane antigen (PSMA), and certain carbohydrates which can target cancer. Similar strategies can be used to target other diseases and pathological changes.

Exemplary targeting moieties include proteins, peptides, nucleic acids, lipids, saccharides, or polysaccharides that bind to one or more targets associated with an organ, tissue, cell, or extracellular matrix, or specific type of tumor or infected cell. The degree of specificity with which the reactants are targeted can be modulated through the selection of a targeting molecule with the appropriate affinity and specificity. For example, a targeting moiety can be a polypeptide, such as an antibody that specifically recognizes a tumor marker that is present exclusively or in higher amounts on a malignant cell (e.g., a tumor antigen). Suitable targeting molecules that can be used to direct the reactants to cells and tissues of interest, as well as methods of conjugating target molecules to the reactants, are known in the art. See, for example, Ruoslahti, et al. Nat. Rev. Cancer, 2:83-90 (2002). Targeting molecules can also include neuropilins and endothelial targeting molecules, integrins, selectins, and adhesion molecules. Targeting molecules can be covalently bound to the reactants using a variety of methods known in the art. Targeting moieties can be connected to the compounds of the invention via a linking moiety as described herein. In such cases, the targeting moiety is present as part of a grouping —$R^L$-$R^T$, wherein $R^L$ is the linking moiety and $R^T$ is the targeting moiety.

In some embodiments, the linking moiety in the first unsaturated molecule, the second unsaturated molecule, or the precursor molecule is selected from the group consisting of:

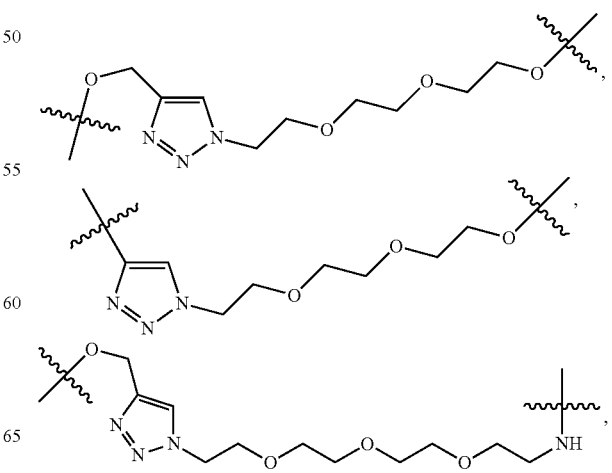

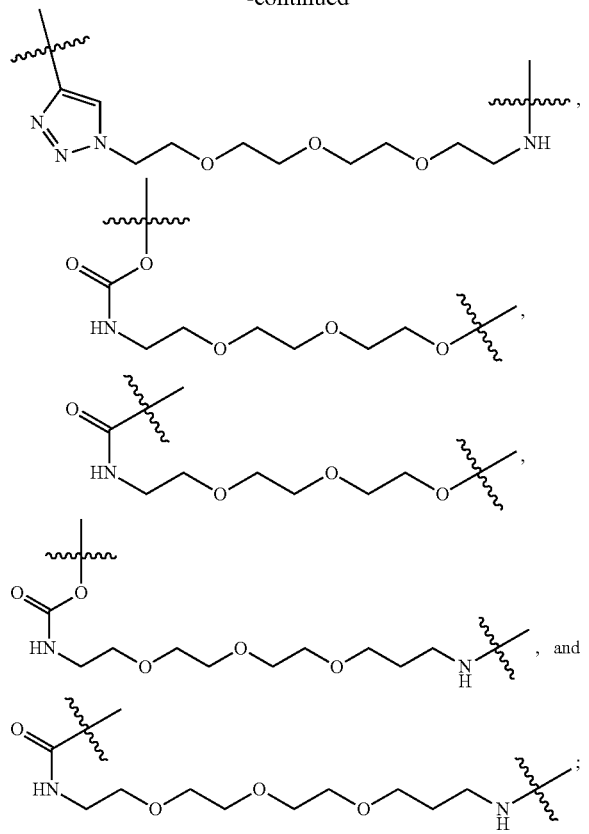

or a pharmaceutically acceptable salt thereof.

In some embodiments, the targeting moiety in the first unsaturated molecule, the second unsaturated molecule, or the precursor molecule is a selected from the group consisting of a folate moiety, and RGD peptide, and a cancer-targeting moiety. In some embodiments, the cancer-targeting moiety is selected from the group consisting of a cancer-targeting carbohydrate and prostate specific membrane antigen (PSMA).

In some embodiments, the targeting moiety in the first unsaturated molecule, the second unsaturated molecule, or the precursor molecule is selected from the group consisting of

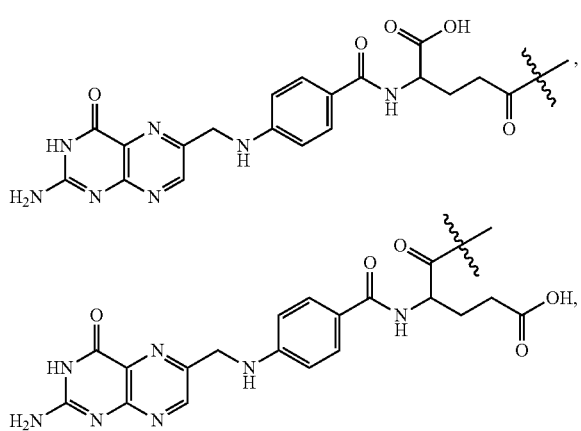

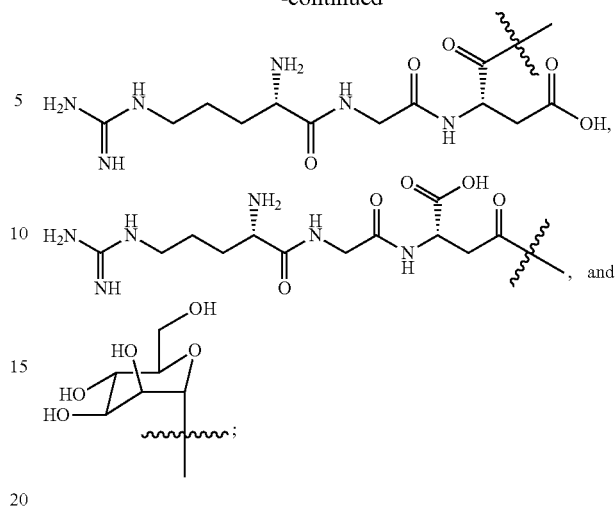

or a pharmaceutically acceptable salt thereof.

In some embodiments, the solubility-enhancing moiety in the first unsaturated molecule, the second unsaturated molecule, or the precursor molecule moiety is a carbohydrate. In some embodiments, the carbohydrate is selected from the group consisting of a monosaccharide, a disaccharide, an oligosaccharide, and a polysaccharide. In some embodiments, the monosaccharide is selected from the group consisting of mannose and glucose. In some embodiments, the polysaccharide is dextran. Solubility-enhancing moieties can be connected to the compounds of the invention via a linking moiety as described herein. In such cases, the solubility-enhancing moiety is present as part of a grouping —$R^L$-$R^S$, wherein $R^L$ is the linking moiety and $R^S$ is the solubility-enhancing moiety.

In some embodiments, the first unsaturated molecule and the second unsaturated molecule, or the precursor molecule, are bound to a support selected from the group consisting of a solid bead, a soluble polymer, an insoluble polymer, a protein, a nucleic acid, and a carbohydrate. In some embodiments, the first unsaturated molecule and the second unsaturated molecule, or the precursor molecule, are covalently bonded to the support. In some embodiments, the first unsaturated molecule and the second unsaturated molecule, or the precursor molecule, are non-covalently bonded to the support. In some embodiments, the first unsaturated molecule and the second unsaturated molecule, or the precursor molecule, are adsorbed to the support or physically entrapped within the support.

In some embodiments, the cycloaddition reaction occurs and carbon monoxide is released under physiological conditions. In some embodiments, the amount of CO released is from about 10 to about 250 ppm.

In some embodiments, the first unsaturated molecule and the second unsaturated molecule, or the precursor molecule, are administered parenterally.

In some embodiments, the first unsaturated molecule and the second unsaturated molecule, or the precursor molecule, are implanted.

In some embodiments, the carbon monoxide is generated in vivo.

In some embodiments, generating carbon monoxide in vivo. comprises administering the precursor molecule to a subject in need thereof.

In a related aspect, the invention provides a method for generating carbon monoxide in vivo, the method comprising administering one or more biocompatible cycloaddition products that release an effective amount of carbon monoxide in vivo under physiological conditions.

In another aspect, the invention provides compounds for releasing CO as described herein. In some embodiments, the compound is selected from compound 30 in Example 1, compounds 54, 55, 56, 57, 60, and 61 in Example 7, and compounds 63, 64, and 66 in Example 8. In some embodiments, the compound is selected from compounds 2a, 2b, and 2c in Example 2. In some embodiments, the compound is selected from compounds 10a, 10b, 10c, and 10d in Example 3. In some embodiments, the compound is compound 51 in Example 4. In some embodiments, the compound has a structure according to Formula II or Formula III as described herein. In some embodiments, the compound has a structure according to Formula IX, Formula IXa, Formula X, Formula XI, Formula XII, Formula XIII, Formula XIV, Formula XV, or Formula XVI as described herein.

II. Pharmaceutical Compositions

In another aspect, the invention provides a pharmaceutical composition comprising one or more pharmaceutically acceptable excipients and
    a first unsaturated molecule and a second unsaturated molecule that react to form a cycloaddition product that releases an effective amount of carbon monoxide under physiological conditions, or
    a precursor molecule having a first site of unsaturation and a second site of unsaturation that react to form a cycloaddition product that releases an effective amount of carbon monoxide under physiological conditions.

In some embodiments, the composition contains the first unsaturated molecule and the second unsaturated molecule. In some embodiments, the first unsaturated molecule and the second unsaturated molecule are formulated together. In some embodiments, the first unsaturated molecule and the second unsaturated molecule are formulated separately.

In some embodiments, the first unsaturated molecule has a structure according to formula:

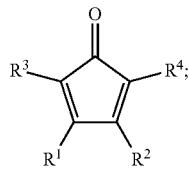

(I)

or a pharmaceutically acceptable salt thereof, wherein:
each $R^1$, $R^2$, $R^3$, and $R^4$ is independently selected from the group consisting of hydrogen, halogen, alkyl, cycloalkyl, heterocycloalkyl, alkenyl, alkynyl, aryl, heteroaryl, alkoxy, aryloxy, hydroxyl, —N(R$^a$)$_2$, —SR$^a$, —S(O)R$^a$, —S(O)$_2$R$^a$, —OS(O)OR$^a$, —OS(O)$_2$OR$^a$, —OP(OR$^a$)$_2$, —OP(O)HOR$^a$, —OP(O)(OR$^a$)$_2$, —OP(O)(R$^a$)$_2$, —P(O)(OR$^a$)$_2$, —ONO, —ONO$_2$, —NO$_2$, —(C=O)R$^5$, —(C=O)OR$^6$, —(C=O)NR$^7$R$^8$, a linking moiety $R^L$, a targeting moiety $R^T$, and a solubility-enhancing moiety $R^S$;
or, alternatively, $R^1$ and $R^2$ are selected from cycloalkyl, heterocycloalkyl, aryl, and heteroaryl, and are taken together to form a fused tricyclic moiety which is optionally substituted with one or more $R^9$ moieties, wherein each $R^9$ is selected from the group consisting of halogen, alkyl, cycloalkyl, heterocycloalkyl, alkenyl, alkynyl, aryl, heteroaryl, alkoxy, aryloxy, hydroxyl, —N(R$^a$)$_2$, —SR$^a$, —S(O)R$^a$, —S(O)$_2$R$^a$, —OS(O)OR$^a$, —OS(O)$_2$OR$^a$, —OP(OR$^a$)$_2$, —OP(O)HOR$^a$, —OP(O)(OR$^a$)$_2$, —OP(O)(R$^a$)$_2$, —P(O)(OR$^a$)$_2$, —ONO, —ONO$_2$, —NO$_2$, —(C=O)R$^5$, —(C=O)OR$^6$, —(C=O)NR$^7$R$^8$, a linking moiety $R^L$, a targeting moiety $R^T$, and a solubility-enhancing moiety $R^S$;
each $R^5$, $R^6$, $R^7$, and $R^8$ is independently selected from the group consisting of hydrogen, alkyl, heteroalkyl, alkenyl, heteroalkenyl, alkynyl, heteroalkynyl, cycloalkyl, heterocycloalkyl, aryl, and heteroaryl; and
$R^a$ is selected from the group consisting of H, alkyl, aryl, cycloalkyl, and heteroaryl.

In some embodiments, the first unsaturated molecule has structure according to formula:

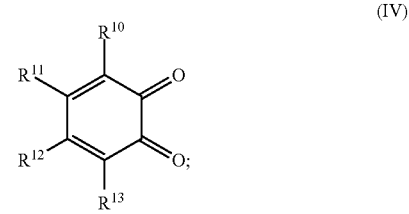

(IV)

or a pharmaceutically acceptable salt thereof, wherein:
each $R^{10}$, $R^{11}$, $R^{12}$ and $R^{13}$ is independently selected from the group consisting of hydrogen, halogen, alkyl, cycloalkyl, heterocycloalkyl, alkenyl, alkynyl, aryl, heteroaryl, alkoxy, aryloxy, hydroxyl, —N(R$^a$)$_2$, —SR$^a$, —S(O)R$^a$, —S(O)$_2$R$^a$, —OS(O)OR$^a$, —OS(O)$_2$OR$^a$, —OP(OR$^a$)$_2$, —OP(O)HOR$^a$, —OP(O)(OR$^a$)$_2$, —OP(O)(R$^a$)$_2$, —P(O)(OR$^a$)$_2$, —ONO, —ONO$_2$, —NO$_2$, —(C=O)R$^5$, —(C=O)OR$^6$, —(C=O)NR$^7$R$^8$, a linking moiety $R^L$, a targeting moiety $R^T$, and a solubility-enhancing moiety $R^S$;
$R^a$ is selected from the group consisting of hydrogen, alkyl, cycloalkyl, aryl or heteroaryl; and
each $R^5$, $R^6$, $R^7$, and $R^8$ is independently selected from the group consisting of hydrogen, alkyl, heteroalkyl, alkenyl, heteroalkenyl, alkynyl, heteroalkynyl, cycloalkyl, heterocycloalkyl, aryl, and heteroaryl.

Any functional groups can be introduced as substituents; however, no functional groups should be present which are reactive towards the dienophile as they can interfere with the DARinv. Examples include, but are not limited to, azido groups.

In some embodiments, each $R^{10}$, $R^{11}$, $R^{12}$ and $R^{13}$ is independently selected to increase the hydrophilicity of the diene and therefore the water-solubility. In some embodiments, $R^{10}$, $R^{11}$, $R^{12}$ and $R^{13}$ are independently selected to contain hydroxyl-, amine-, and carboxylic acid groups, which can be tethered to diene molecules to improve the aqueous solubility of the diene.

In some embodiments, each $R^{10}$, $R^{11}$, $R^{12}$ and $R^{13}$ is independently selected to couple or immobilize the diene to solid beads, polyethylene glycol and other soluble and insoluble polymers and macromolecules including proteins, nucleic acids, and carbohydrates to improve solubility of the molecules and/or reduce toxicity by preventing or reducing passage of the diene into cells.

In some embodiments, each $R^{10}$, $R^{11}$, $R^{12}$ and $R^{13}$ is independently selected to couple to a targeting molecule such as folate, an RGD peptide, other ligands for cancer-associated biomarkers such as prostate specific membrane antigen (PSMA), and certain carbohydrates which can target cancer. Similar strategies can be used to target other diseases and pathological changes.

In some embodiments, the second unsaturated molecule has a structure according to Formula V:

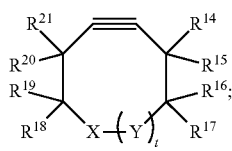

(V)

or a pharmaceutically acceptable salt thereof, wherein:
each $R^{14}$, $R^{15}$, $R^{16}$, $R^{17}$, $R^{18}$, $R^{19}$, $R^{20}$, and $R^{21}$ is independently selected from the group consisting of hydrogen, halogen, substituted or unsubstituted alkyl, cycloalkyl, heterocycloalkyl, alkenyl, alkynyl, aryl, heteroaryl, alkoxy, or aryloxy,
hydroxyl, —N($R^a$)$_2$, —S$R^a$, —S(O)$R^a$, —S(O)$_2R^a$, —OS(O)O$R^a$, —OS(O)$_2$O$R^a$, —OP(O$R^a$)$_2$, —OP(O)H O$R^a$, —OP(O)(O$R^a$)$_2$, —OP(O)($R^a$)$_2$, —P(O)(O$R^a$)$_2$, —ONO, —ONO$_2$, —NO$_2$, —(C=O)$R^{5'}$, —(C=O)O$R^{6'}$, —(C=O)N$R^{7'}R^{8'}$, a linking moiety $R^L$, a targeting moiety $R^T$, and a solubility-enhancing moiety $R^S$;
$R^{14}$ or $R^{15}$ is optionally taken together with $R^{16}$ or $R^{17}$ to form fused cycloalkyl, fused heterocyclyl, fused aryl, or fused heteroaryl, optionally substituted with $R^{9'}$;
$R^{18}$ or $R^{19}$ is optionally taken together with $R^{20}$ or $R^{21}$ to form fused cycloalkyl, fused heterocyclyl, fused aryl, or fused heteroaryl, optionally substituted with $R^{9'}$;
Y is selected from the group consisting of $CR^{22a}R^{22b}$, S, O, and N$R^a$;
X is selected from the group consisting of $CR^{23a}R^{23b}$, S, O, and N$R^a$;
wherein each $R^{22a}$, $R^{22b}$, $R^{23a}$, and $R^{23b}$ is defined the same as $R^{14}$;
wherein $R^{22a}$ or $R^{22b}$ is optionally taken together with $R^{23a}$ or $R^{23b}$ to form a cyclic moiety optionally substituted with $R^{24}$;
wherein $R^{24}$ is same as $R^{14}$;
$R^a$ is selected from the group consisting of hydrogen, alkyl, cycloalkyl, aryl and heteroaryl;
each $R^{5'}$, $R^{6'}$, $R^{7'}$, and $R^{8'}$ is independently selected from the group consisting of hydrogen, alkyl, heteroalkyl, alkenyl, heteroalkenyl, alkynyl, heteroalkynyl, cycloalkyl, heterocycloalkyl, aryl, and heteroaryl; and
subscript t is 0 or 1.

In some embodiments, the composition comprises the precursor molecule.

In some embodiments, the precursor molecule has a structure according to Formula IX:

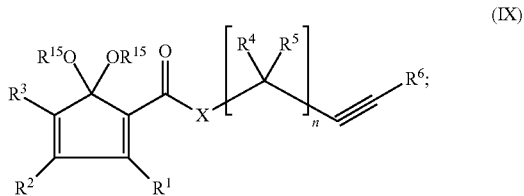

(IX)

or a pharmaceutically acceptable salt thereof, wherein:
each $R^1$, $R^2$, $R^3$, $R^4$, $R^5$, and $R^6$ is independently selected from the group consisting of hydrogen, halogen, substituted or unsubstituted alkyl, cycloalkyl, heterocycloalkyl, alkenyl, alkynyl, aryl, heteroaryl, alkoxy, aryloxy,
hydroxyl, —N($R^a$)$_2$, —S$R^a$, —S(O)$R^a$, —S(O)$_2R^a$, —OS(O)O$R^a$, —OS(O)$_2$O$R^a$, —OP(O$R^a$)$_2$, —OP(O)H O$R^a$, —OP(O)(O$R^a$)$_2$, —OP(O)($R^a$)$_2$, —P(O)(O$R^a$)$_2$, —ONO, —ONO$_2$, —NO$_2$, —(C=O)$R^7$, —(C=O)O$R^8$, —(C=O)N$R^9R^{10}$, a protecting moiety $R^P$, a linking moiety $R^L$, a targeting moiety $R^T$, and a solubility-enhancing moiety $R^S$;
or, alternatively, $R^1$ and $R^2$ are independently selected from the group consisting of cycloalkyl, heterocycloalkyl, aryl, and heteroaryl, and are taken together to form a fused tricyclic moiety which is optionally substituted with one or more $R^{11}$ moieties, wherein
each $R^{11}$ is independently selected from the group consisting of halogen, alkyl, cycloalkyl, heterocycloalkyl, alkenyl, alkynyl, aryl, heteroaryl, alkoxy, aryloxy,
hydroxyl, —N($R^a$)$_2$, —S$R^a$, —S(O)$R^a$, —S(O)$_2R^a$, —OS(O)O$R^a$, —OS(O)$_2$O$R^a$, —OP(O$R^a$)$_2$, —OP(O)H O$R^a$, —OP(O)(O$R^a$)$_2$, —OP(O)($R^a$)$_2$, —P(O)(O$R^a$)$_2$, —ONO, —ONO$_2$, —NO$_2$, —(C=O)$R^5$, —(C=O)O$R^6$, —(C=O)N$R^7R^8$, a linking moiety $R^L$, a targeting moiety $R^T$, and a solubility-enhancing moiety $R^S$;
$R^a$ is selected from the group consisting of hydrogen, alkyl, cycloalkyl, aryl or heteroaryl;
each $R^7$, $R^8$, $R^9$, and $R^{10}$ is independently selected from the group consisting of hydrogen, alkyl, heteroalkyl, alkenyl, heteroalkenyl, alkynyl, heteroalkynyl, cycloalkyl, heterocycloalkyl, aryl, and heteroaryl;
X is $CR^{12}R^{13}$, S, O, or N$R^{14}$, wherein each $R^{12}$ and $R^{13}$ is defined as for $R^1$, and $R^{14}$ is defined as for $R^7$;
each $R^{15}$ is independently selected from the group consisting of hydrogen, alkyl, cycloalkyl, heterocycloalkyl, alkenyl, alkynyl, aryl, and heteroaryl,
or, alternatively two O$R^{15}$ are taken together to form an oxo moiety; and
subscript n is 1, 2 or 3.

In some embodiments, the precursor molecule has a structure according to Formula XII:

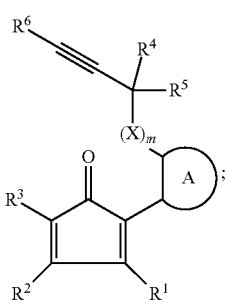

(XIV)

or a pharmaceutically acceptable salt thereof, wherein:
each $R^1$, $R^2$, $R^3$, $R^4$, $R^5$, and $R^6$ is independently selected from the group consisting of hydrogen, halogen, substituted or unsubstituted alkyl, cycloalkyl, heterocycloalkyl, alkenyl, alkynyl, aryl, heteroaryl, alkoxy, aryloxy,
hydroxyl, —N($R^a$)$_2$, —S$R^a$, —S(O)$R^a$, —S(O)$_2R^a$, —OS(O)O$R^a$, —OS(O)$_2$O$R^a$, —OP(O$R^a$)$_2$, —OP(O)H O$R^a$, —OP(O)(O$R^a$)$_2$, —OP(O)($R^a$)$_2$, —P(O)(O$R^a$)$_2$, —ONO, —ONO$_2$, —NO$_2$, —(C=O)R$^7$, —(C=O)OR$^8$, —(C=O)NR$^9$R$^{10}$, a protecting moiety R$^P$, a linking moiety R$^L$, a targeting moiety R$^T$, and a solubility-enhancing moiety R$^S$;

or, alternatively, R$^1$ and R$^2$ are independently selected from the group consisting of cycloalkyl, heterocycloalkyl, aryl, and heteroaryl, and are taken together to form a fused tricyclic moiety which is optionally substituted with one or more R$^{11}$ moieties, wherein each R$^{11}$ is selected from the group consisting of hydrogen, halogen, alkyl, cycloalkyl, heterocycloalkyl, alkenyl, alkynyl, aryl, heteroaryl, alkoxy, aryloxy, hydroxyl, —N(R$^a$)$_2$, —SR$^a$, —S(O)R$^a$, —S(O)$_2$R$^a$, —OS(O)OR$^a$, —OS(O)$_2$OR$^a$, —OP(OR$^a$)$_2$, —OP(O)HOR$^a$, —OP(O)(OR$^a$)$_2$, —OP(O)(R$^a$)$_2$, —P(O)(OR$^a$)$_2$, —ONO, —ONO$_2$, —NO$_2$, —(C=O)R$^5$, —(C=O)OR$^6$, —(C=O)NR$^7$R$^8$, a linking moiety R$^L$;

R$^a$ is selected from the group consisting of hydrogen, alkyl, cycloalkyl, aryl or heteroaryl;

each R$^7$, R$^8$, R$^9$, and R$^{10}$ is independently selected from the group consisting of hydrogen, alkyl, heteroalkyl, alkenyl, heteroalkenyl, alkynyl, heteroalkynyl, cycloalkyl, heterocycloalkyl, aryl, and heteroaryl;

X is CR$^{12}$R$^{13}$, S, O, or NR$^{14}$, wherein each R$^{12}$ and R$^{13}$ is defined as for R$^1$, and R$^{14}$ is defined as for R$^7$;

"A" is selected from the group consisting of cycloalkyl, heterocycloalkyl, aryl, and heteroaryl; and subscript m is 1, 2 or 3, provided that only one of X is S or O when m is 2 or 3.

In one aspect, the invention provides a pharmaceutical composition comprising a cycloaddition product that releases an effective amount of carbon monoxide under physiological conditions.

A. Reactants

In some embodiments, the cycloaddition reaction takes place in vivo to form a product which subsequently releases carbon monoxide. In these embodiments, the diene and dienophile are formulated for administration to the patient. The diene and dienophile can be administered by any known route of administration. The diene and dienophile can be administered together, simultaneously, or sequentially. Since body temperature will typically be sufficient to initiate the reaction, the diene and dienophile can be administered separately (e.g., in different formulations) or in the same formulation but segregated in the formulation to ensure the reaction does not occur or occurs minimally outside the body. If the reaction occurs at body temperature, but not at room temperature (or lower), the reactants can be formulated together.

The diene and/or dienophile can be formulated in a pharmaceutically acceptable solvent, such as purified water, buffer, or other pharmaceutically acceptable solvent. The diene and/or dienophile can also be formulated in a liposome or micelle. The amount of diene and dienophile to be administered can be readily determined based on the amount of carbon monoxide to be generated.

B. Cycloaddition Adducts

In some embodiments, the cycloaddition product is prepared ex vivo and formulated for administration to a patient. Once administered, the higher temperature in the body catalyzes release of carbon monoxide. In such embodiments, the Diels-Alder product can be formulated for any route of administration, preferably enteral or parenteral formulation.

Parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

Suitable surfactants may be anionic, cationic, amphoteric or nonionic surface-active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

C. Nanoparticles and Microparticles

For parenteral administration, the one or more products, and optional one or more additional active agents, can be incorporated into microparticles, nanoparticles, or combinations thereof that provide controlled release of the products and/or one or more additional active agents. In embodiments wherein the formulations contains two or more drugs, the drugs can be formulated for the same type of controlled release (e.g., delayed, extended, immediate, or pulsatile) or the drugs can be independently formulated for different types of release (e.g., immediate and delayed, immediate and extended, delayed and extended, delayed and pulsatile, etc.).

For example, the products and/or one or more additional active agents can be incorporated into polymeric microparticles, which provide controlled release of the drug(s). Release of the drug(s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives.

Polymers which are slowly soluble and form a gel in an aqueous environment, such as hydroxypropyl methylcellulose or polyethylene oxide may also be suitable as materials for drug containing microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

Alternatively, the drug(s) can be incorporated into microparticles prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including but not limited to fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material, which is normally solid at room temperature and has a melting point of from about 30 to 300° C.

In some cases, it may be desirable to alter the rate of water penetration into the microparticles. To this end, rate-controlling (wicking) agents may be formulated along with the fats or waxes listed above. Examples of rate-controlling materials include certain starch derivatives (e.g., waxy maltodextrin and drum dried corn starch), cellulose derivatives (e.g., hydroxypropylmethyl-cellulose, hydroxypropylcellulose, methylcellulose, and carboxymethyl-cellulose), alginic acid, lactose and talc. Additionally, a pharmaceutically acceptable surfactant (for example, lecithin) may be added to facilitate the degradation of such microparticles.

Proteins which are water insoluble, such as zein, can also be used as materials for the formation of drug containing microparticles. Additionally, proteins, polysaccharides and combinations thereof which are water soluble can be formulated with drug into microparticles and subsequently cross-linked to form an insoluble network. For example, cyclodextrins can be complexed with individual drug molecules and subsequently cross-linked.

Encapsulation or incorporation of drug into carrier materials to produce drug containing microparticles can be achieved through known pharmaceutical formulation techniques. In the case of formulation in fats, waxes or wax-like materials, the carrier material is typically heated above its melting temperature and the drug is added to form a mixture comprising drug particles suspended in the carrier material, drug dissolved in the carrier material, or a mixture thereof. Microparticles can be subsequently formulated through several methods including, but not limited to, the processes of congealing, extrusion, spray chilling or aqueous dispersion. In a preferred process, wax is heated above its melting temperature, drug is added, and the molten wax-drug mixture is congealed under constant stirring as the mixture cools. Alternatively, the molten wax-drug mixture can be extruded and spheronized to form pellets or beads. These processes are known in the art.

For some carrier materials it may be desirable to use a solvent evaporation technique to produce drug-containing microparticles. In this case drug and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In some embodiments, drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some embodiments drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

The particles can also be coated with one or more modified release coatings. Solid esters of fatty acids, which are hydrolyzed by lipases, can be spray coated onto microparticles or drug particles. Zein is an example of a naturally water-insoluble protein. It can be coated onto drug containing microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin. Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing microparticles or drug particles, a water soluble protein can be spray coated onto the microparticles and subsequently cross-linked by the one of the methods described above. Alternatively, drug-containing microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations, which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

In certain embodiments, it may be desirable to provide continuous delivery of one or more products to a patient in need thereof. For intravenous or intraarterial routes, this can be accomplished using drip systems, such as by intravenous administration.

D. Injectable/Implantable Solid Implants

The products described herein can be incorporated into injectable/implantable solid or semi-solid implants, such as polymeric implants. In one embodiment, the products are incorporated into a polymer that is a liquid or paste at room temperature, but upon contact with aqueous medium, such as physiological fluids, exhibits an increase in viscosity to form a semi-solid or solid material. Exemplary polymers include, but are not limited to, hydroxyalkanoic acid polyesters derived from the copolymerization of at least one unsaturated hydroxy fatty acid copolymerized with hydroxyalkanoic acids. The polymer can be melted, mixed with the active substance and cast or injection molded into a device. Such melt fabrication require polymers having a melting point that is below the temperature at which the substance to be delivered and polymer degrade or become reactive. The device can also be prepared by solvent casting where the polymer is dissolved in a solvent and the drug dissolved or dispersed in the polymer solution and the solvent is then evaporated. Solvent processes require that the polymer be soluble in organic solvents. Another method is compression molding of a mixed powder of the polymer and the drug or polymer particles loaded with the active agent.

Alternatively, the products can be incorporated into a polymer matrix and molded, compressed, or extruded into a device that is a solid at room temperature. For example, the products can be incorporated into a biodegradable polymer, such as polyanhydrides, polyhydroalkanoic acids (PHAs), PLA, PGA, PLGA, polycaprolactone, polyesters, polyamides, polyorthoesters, polyphosphazenes, proteins and polysaccharides such as collagen, hyaluronic acid, albumin and gelatin, and combinations thereof and compressed into solid device, such as disks, or extruded into a device, such as rods.

The release of the one or more products from the implant can be varied by selection of the polymer, the molecular weight of the polymer, and/or modification of the polymer to increase degradation, such as the formation of pores and/or incorporation of hydrolyzable linkages. Methods for modifying the properties of biodegradable polymers to vary the release profile of the products from the implant are well known in the art.

E. Enteral Formulations

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Carrier also includes all components of the coating composition which may include plasticizers, pigments, colorants, stabilizing agents, and glidants. Delayed release dosage formulations may be prepared as described in standard references. These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers are used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

F. Controlled Release Formulations

Oral dosage forms, such as capsules, tablets, solutions, and suspensions, can for formulated for controlled release. For example, the one or more products and optional one or more additional active agents can be formulated into nanoparticles, microparticles, and combinations thereof, and encapsulated in a soft or hard gelatin or non-gelatin capsule or dispersed in a dispersing medium to form an oral suspension or syrup. The particles can be formed of the drug and a controlled release polymer or matrix. Alternatively, the drug particles can be coated with one or more controlled release coatings prior to incorporation in to the finished dosage form.

In another embodiment, the one or more products and optional one or more additional active agents are dispersed in a matrix material, which gels or emulsifies upon contact with an aqueous medium, such as physiological fluids. In the case of gels, the matrix swells entrapping the active agents, which are released slowly over time by diffusion and/or degradation of the matrix material. Such matrices can be formulated as tablets or as fill materials for hard and soft capsules.

In still another embodiment, the one or more products, and optional one or more additional active agents are formulated into a sold oral dosage form, such as a tablet or capsule, and the solid dosage form is coated with one or more controlled release coatings, such as a delayed release coatings or extended release coatings. The coating or coatings may also contain the products and/or additional active agents.

1. Extended Release Dosage Forms

The extended release formulations are generally prepared as diffusion or osmotic systems, which are known in the art. A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

2. Delayed Release Dosage Forms

Delayed release formulations can be created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

In a related aspect, the invention provides a kit comprising:
  a first unsaturated molecule and a second unsaturated molecule that react to form a cycloaddition product that releases an effective amount of carbon monoxide under physiological conditions, or
  a precursor molecule having a first site of unsaturation and a second site of unsaturation that react to form a cycloaddition product that releases an effective amount of carbon monoxide under physiological conditions

III. Methods of Making

A. Dienes

The reaction rate of the cycloaddition reaction and subsequent release of CO can be controlled/tuned by manipulating the electron density of the diene through the introduction of functional groups at the 1, 2, 3, and/or 4-positions. Scheme 1 shows the synthetic route of dienone analogs, wherein $R^1$-$R^4$ are as defined above. Dienone analogs 2 and 3 could also be obtained by such method.

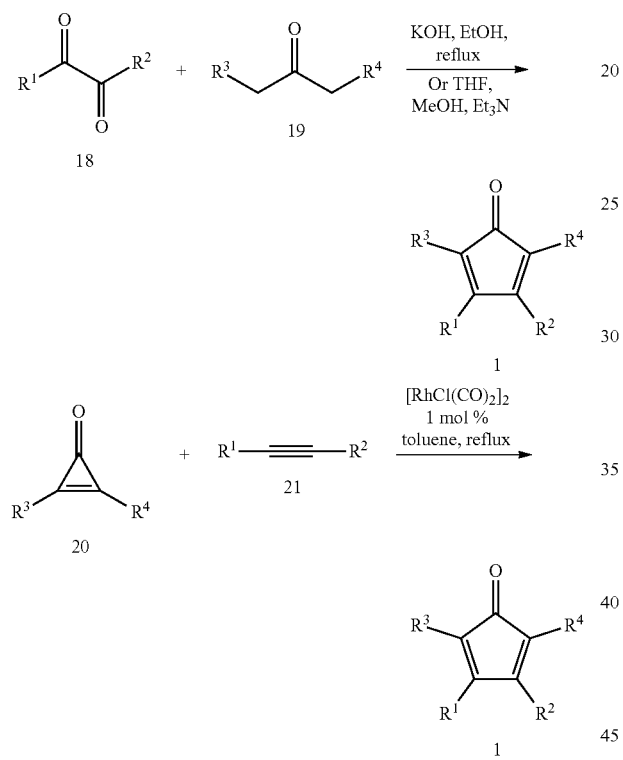

B. Dienophiles

In some embodiments, the dienophile is a strained alkyne such as a cyclooctyne or cycloheptyne. Cycloalkynes can be prepared by techniques known in the art as described, for example, in U.S. Pat. Nos. 7,807,619, and 8,519,122. For example, cycloalkynes can be produced via 3-elimination of the analogous substituted cycloalkene. Alternatively, cycloalkynes can be produced by the ring expansion of a cyclic alkylidinecarbene. Other synthetic methods are known in the art.

C. Intramolecular DARinv

In some embodiments, the dienes and dienophiles were combined into one molecule, which were stable in organic solvent and storage, and released CO under physiological conditions by the intramolecular DARinv. Scheme 2 shows synthetic route to unimolecular CO releasing molecules where $R^1$-$R^6$, X and n are as defined above. By using different starting materials (15), the other analogs 10 and 11 could also be obtained by this method.

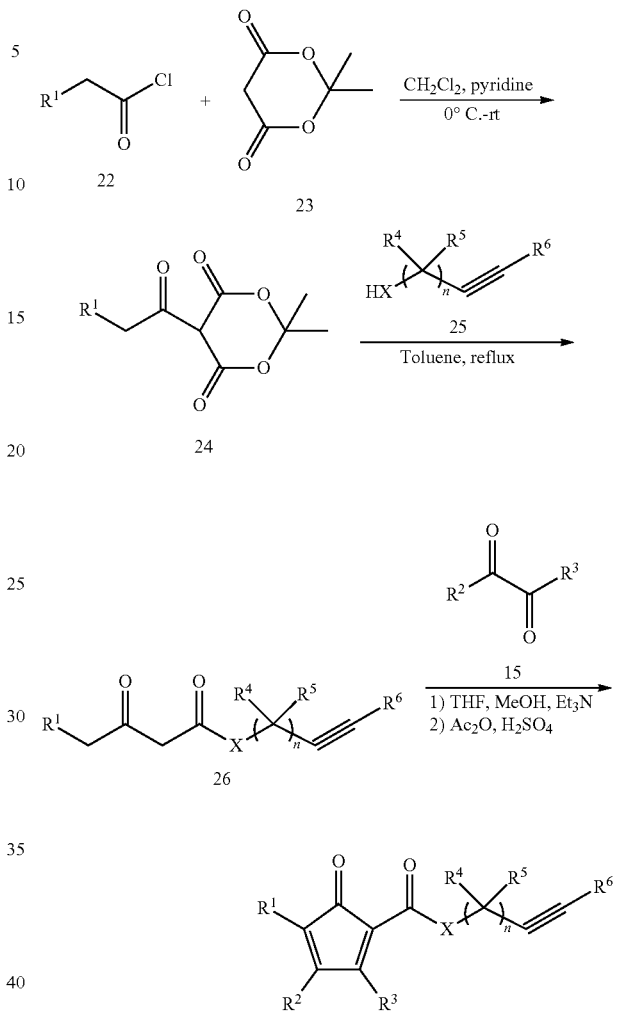

In other embodiments, the carbonyl group of the unimolecular CO releasing molecule is masked as a ketal, which is sensitive to acids and/or esterase activity. Scheme 3 shows synthetic route to acid or esterase activated CO prodrugs, where $R^1$-$R^6$, X and n are as defined above. And R' was chosen from nitro substituted phenyl, fluoro substituted phenyl, or succinimide to give the activated ester. By using a different starting material 24, which can be easily synthesized according to Scheme 1, other analogues 13 and 14 can also be obtained by this method.

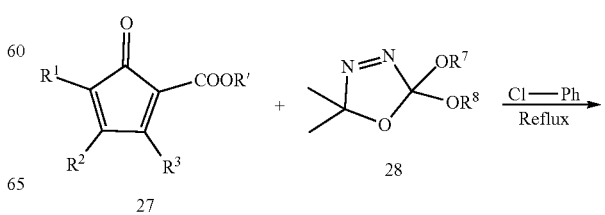

-continued

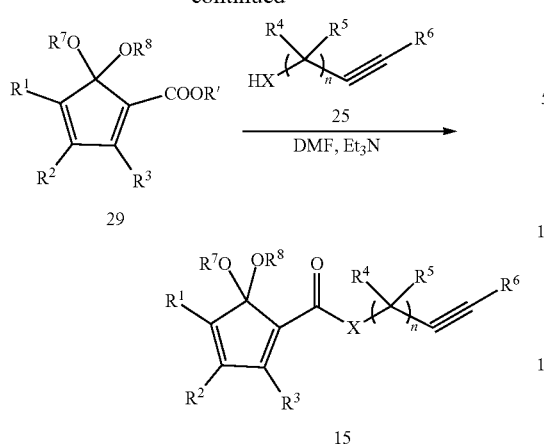

29

D. Cycloaddition Products

Dienone analogues (1) can react with BCN analogues (6a) as shown in Scheme 4. Dienones can be reacted with dienophiles (e.g., strained alkynes) in a cyclization reaction to form inverse electron demand Diels-Alder (DARinv) products as shown in the schemes below:

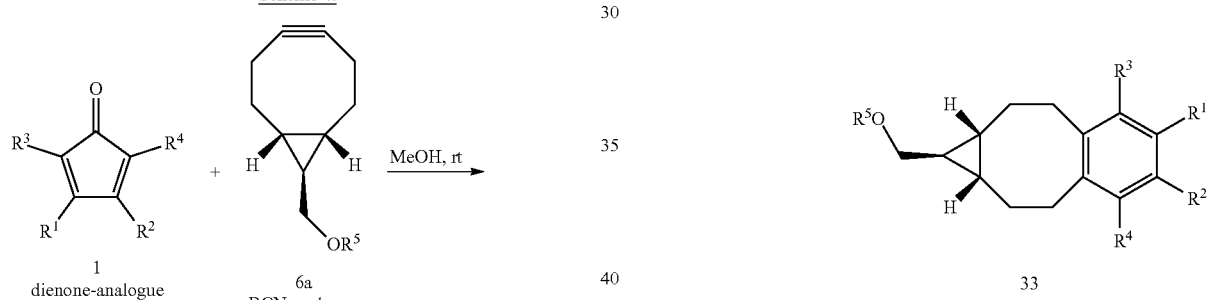

The reaction described in Schemes 4-5 applies to the various stereoisomers of BCN. This is true with other similar cycloaddition reactions described in this invention. Scheme 5 shows the reaction of diene-dione analogues (4) react with BCN analogues (6a).

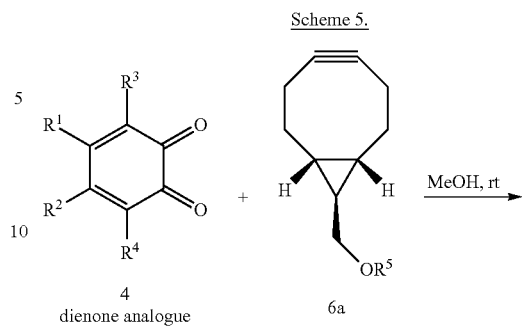

Scheme 6 shows the reaction of dienone analogues (1) with cyclooctyne analogues (5).

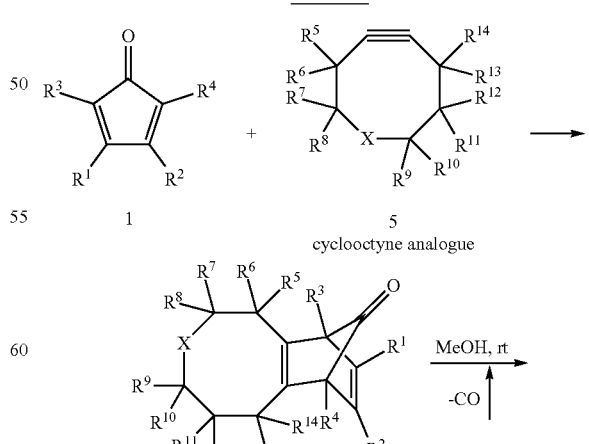

-continued
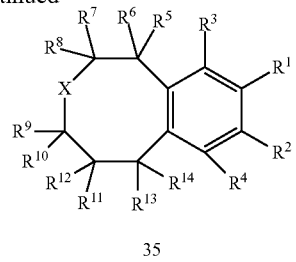
35
Scheme 7 shows the reaction of dienone analogues (1) with DIBO analogues (7).
Scheme 7.
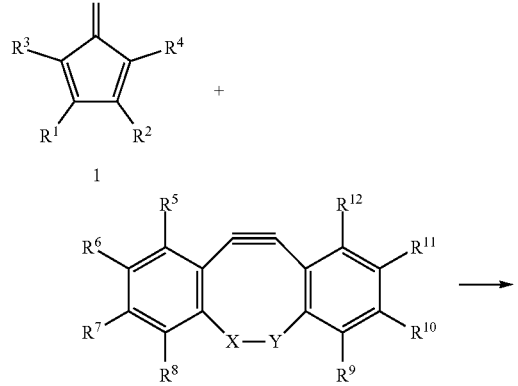
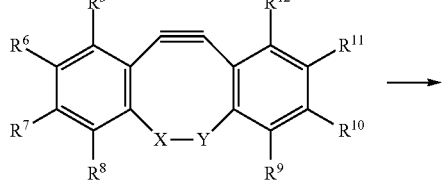
7
DIBO analogue
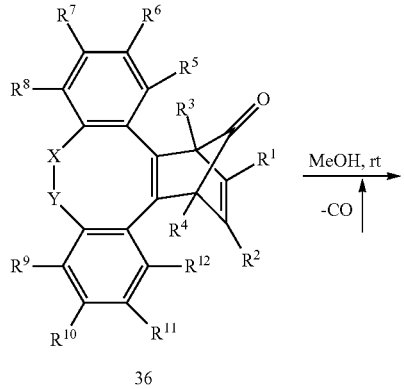
36
37
Scheme 8 shows the reaction of dienone analogues (1) with TMTH analogues (8)
Scheme 8.
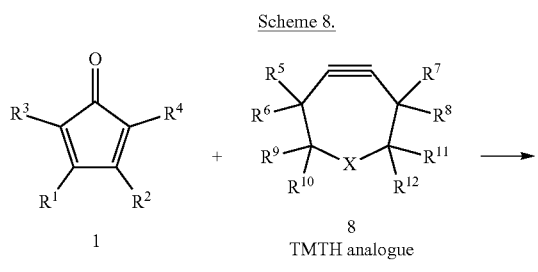
1      8
TMTH analogue
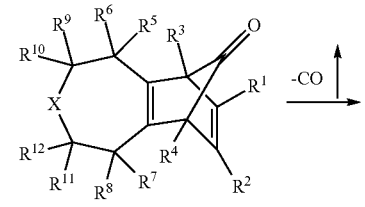
38
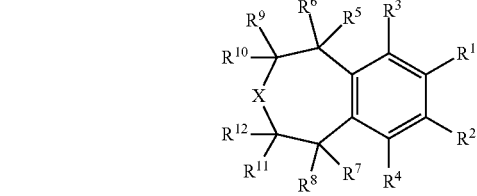
39
Scheme 9 shows the reaction of dienone analogues (1) with other DARinv systems (40)
Scheme 9.
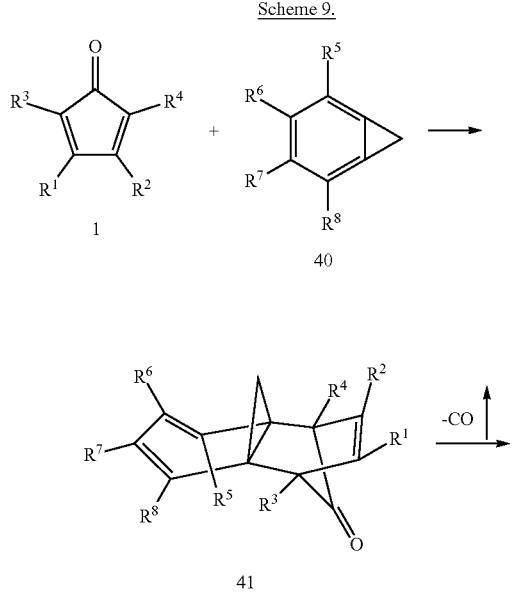

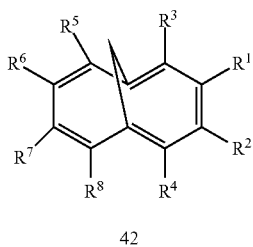

42

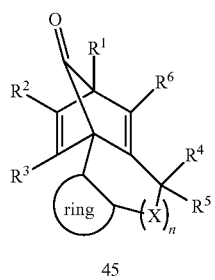

45

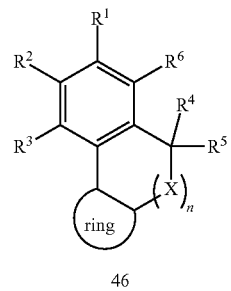

46

Scheme 10 shows unimolecular CO releasing analogues 9 undergoing intramolecular DARinv. Dienone analogues 2-3 can also react with BCN 6a or other dienophiles 5, 7, 8 and 40 listed in scheme 4 and 6-9 to release CO and yield similar cycloadducts.

Other unimolecular CO releasing molecules 13 and 14 can undergo reactions similar to those shown in scheme 11 to release CO and the fluorescent cycloadducts.

IV. Methods of Use

CO has beneficial therapeutic effects. Studies have shown that CO has anti-inflammatory, anti-proliferative, and anti-apoptotic effects when the concentrations of CO in carrier gas (air) ranges from 10 to 250 ppm.

CO has been found to play a key beneficial role in various inflammatory and cardiovascular diseases. Among the various inflammatory related disorders, inflammatory bowel disease (IBD), which is chronic intestinal inflammatory disorder, may be effectively treated by CO. So far, the pathogenesis of IBD is still unclear due to multiple factors involved in the inflammatory processes such as genetic mutations, bacterial infections, and physiological and immunological stress responses.

Tumor necrosis factor alpha (TNF-α) plays a central role in the pathogenesis of IBD, as evidenced by the successful treatment of patients with anti-TNF-α antibodies in multiple clinical trials. The anti-inflammatory effects of CO have been reported using cell culture and animal models of sepsis. CO administration or HO-1 overexpression in RAW 264.7 cells inhibits tumor necrosis factor alpha (TNF-α) expression after treatment with lipopolysaccharide (LPS). In several inflammatory models, CO has been reported to inhibit GM-CSF expression, resulting in attenuation of inflammation. The effective and targeted treatments of IBD are largely limited due to significant systemic side effects. Until now, anti-inflammatory drugs and immunosuppressants are two options used in IBD treatment. There are some mitogen-activated protein kinase (MAPK) inhibitors being developed as treatment options.

Rheumatoid arthritis, psoriasis, uveitis, mid-ear inflammation, and osteoarthritis are more examples of inflammatory disorders that may be treated with CO. Administration of CO from carbon monoxide releasing molecules (CORMs) in a model of collagen-induced arthritis suppressed the clinical and histopathological manifestations of the disease. The data is consistent with the reduction in the levels of inflammatory cytokines, such as interleukins and TNF-α, in joint tissues and decreased cellular infiltration, joint inflammation and cartilage destruction.

Besides anti-inflammatory effects, evidence suggests that CO plays a beneficial role in treating cardiovascular disease. Pulmonary arterial hypertension (PAH), one type of pulmonary hypertension, is an uncurable disease, and is described as high blood pressure in the arteries of the lungs. It is driven by an increased expansion of vascular smooth muscle in the pulmonary arterioles and leads to right heart hypertrophy and infarct. Breathing low concentrations of CO gas (e.g., Scheme 10.

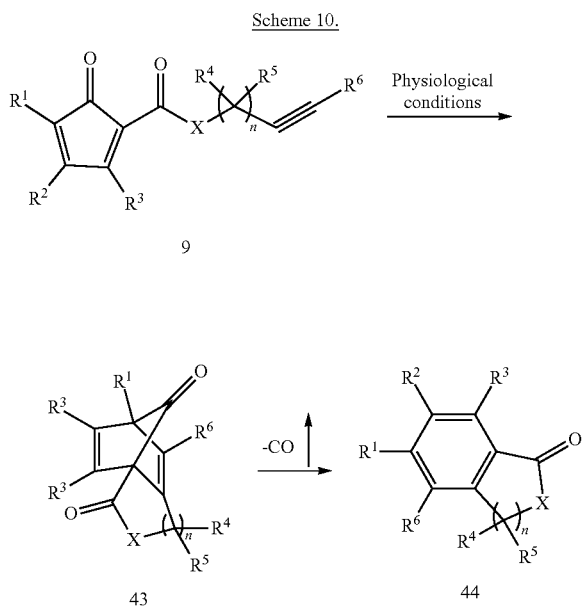

Scheme 11.

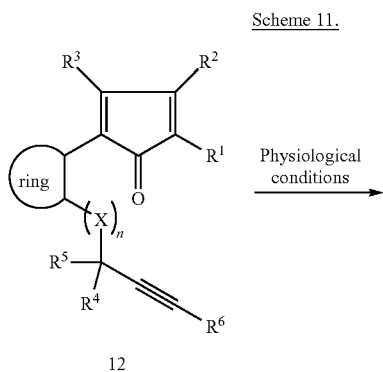

12

150 ppm) has been investigated as a treatment to improve pulmonary arterial hypertension and is currently in phase II clinical trials. Preliminary results have shown that after 16 weeks, the pulmonary vascular resistance has decreased 20% compared to the pre-therapy value. The mechanism of action of CO in the treatment of PAH mechanism has been reported as involving endothelial derived NO to induce apoptosis of the hyper-proliferative vascular smooth muscle cells.

CO can also be used to treat a variety of other disorders including cancer, thrombosis, reduce rejection in organ transplantation (e.g., organ protection), organ preservation, wound healing, autoimmune disorders, hypertension and cardiovascular disease, HIF-1alpha stabilization and protection of cells in stroke, heart attack, hypothermia, etc., and diabetes (e.g., increase sensitization of cells towards insulin) as well as stimulate blood cell formation and maturation, and protect and promote growth of neurons. CO can also be used to prevent, minimize, or reverse toxicity associated with the administration of various therapeutic agents, such as doxorubicin.

The specific dose level selected for any particular patient will depend upon a variety of factors, including the activity of the specific compound employed, the age, body weight, general health, sex, diet, time of administration, route of administration, and rate of excretion, drug combination and the severity of the condition undergoing therapy.

Carbon monoxide releasing compounds (i.e., the first unsaturated molecule, the second unsaturated molecule, or the precursor molecule) can be administered at any suitable dose in the methods of the invention. In general, a carbon monoxide releasing compound is administered at a dose ranging from about 0.1 milligrams to about 1000 milligrams per kilogram of a subject's body weight (i.e., about 0.1-1000 mg/kg). The dose of the carbon monoxide releasing compound can be, for example, about 0.1-1000 mg/kg, or about 1-500 mg/kg, or about 25-250 mg/kg, or about 50-100 mg/kg. The dose of the carbon monoxide releasing compound can be about 1, 2, 3, 4, 5, 10, 15, 20, 25, 30, 35, 40, 45, 50, 55, 60, 65, 70, 75, 85, 90, 95, 100, 150, 200, 250, 300, 350, 400, 450, 500, 550, 600, 650, 700, 750, 800, 850, 900, 950 or 1000 mg/kg. The dose of the carbon monoxide releasing compound can be administered at a dose below about 1, below about 2, below about 3, below about 4, below about 5, below about 10, below about 15, below about 20, below about 25, below about 30, below about 35, below about 40, below about 45, below about 50, below about 55, below about 60, below about 65, below about 70, below about 75, below about 85, below about 90, below about 95, below about 100, below about 150, below about 200, below about 250, below about 300, below about 350, below about 400, below about 450, below about 500, below about 550, below about 600, below about 650, below about 700, below about 750, below about 800, below about 850, below about 900, below about 950, or below about 1000 mg/kg.

The dosages can be varied depending upon the needs of the patient, the particular formulation being administered, and other factors. The dose administered to a patient should be sufficient to result in a beneficial therapeutic response in the patient. The size of the dose will also be determined by the existence, nature, and extent of any adverse side-effects that accompany the administration of the drug in a particular patient. Determination of the proper dosage for a particular situation is within the skill of the typical practitioner. The total dosage can be divided and administered in portions over a period of time suitable to address the carbon monoxide requirement.

Administration of a carbon monoxide releasing compound can be conducted for a period of time which will vary depending upon the nature of the particular carbon monoxide requirement, its severity and the overall condition of the patient. Administration can be conducted, for example, hourly, every 2 hours, three hours, four hours, six hours, eight hours, or twice daily including every 12 hours, or any intervening interval thereof. Administration can be conducted once daily, or once every 36 hours or 48 hours, or once every month or several months. Following treatment, a patient can be monitored for changes in his or her condition and for alleviation of the symptoms of the carbon monoxide requirement. The dosage of the carbon monoxide releasing compound can either be increased in the event the patient does not respond significantly to a particular dosage level, or the dose can be decreased if an alleviation of the symptoms of the carbon monoxide requirement is observed, or if the carbon monoxide requirement has been ablated, or if unacceptable side effects are seen with a particular dosage.

A therapeutically effective amount of carbon monoxide releasing compound can be administered to the subject in a treatment regimen comprising intervals of at least 1 hour, or 6 hours, or 12 hours, or 24 hours, or 36 hours, or 48 hours between dosages. Administration can be conducted at intervals of at least 72, 96, 120, 168, 192, 216, or 240 hours, or the equivalent amount of days. The dosage regimen can consist of two or more different interval sets. For example, a first part of the dosage regimen can be administered to a subject multiple times daily, daily, every other day, or every third day. The dosing regimen can start with dosing the subject every other day, every third day, weekly, biweekly, or monthly. The first part of the dosing regimen can be administered, for example, for up to 30 days, such as 7, 14, 21, or 30 days. A subsequent second part of the dosing regimen with a different interval administration administered weekly, every 14 days, or monthly can optionally follow, continuing for 4 weeks up to two years or longer, such as 4, 6, 8, 12, 16, 26, 32, 40, 52, 63, 68, 78, or 104 weeks. Alternatively, if the carbon monoxide requirement decreases, the dosage may be maintained or kept at lower than maximum amount. If the requirement increases, the first dosage regimen can be resumed until an improvement is seen, and the second dosing regimen can be implemented again. This cycle can be repeated multiple times as necessary.

EXAMPLES

Materials and Methods

All reagents and solvents were reagent grade or were purified by standard methods before use. Column chromatography was carried out on flash silica gel (Sorbent 230-400 mesh). TLC analysis was conducted on silica gel plates (Sorbent Silica G UV254). NMR spectra were recorded at $^1$H (400 MHz) and $^{13}$C (100 MHz) on a Bruker instrument. Chemical shifts (δ values) and coupling constants (J values) are given in ppm and hertz respectively, using solvents ($^1$H NMR, $^{13}$C NMR) as the internal standard. BCN was synthesized according to literature procedures.

Example 1. Synthesis of Carbon Monoxide-Releasing Molecule 30

A molecule was synthesized that generates a controlled amount of CO at room temperature with tunable reaction rates. This click reaction can be activated under physiological conditions and delivers CO over an extended period of time. The release of CO was demonstrated by the deoxymyoglobin (deoxyMb) trapping assay and detection by a commercially available CO detector. (Model: Kidde KN-COB-B-LPM). Scheme 12 shows inverse-electron demand Diels-Alder reaction between tetraphenylcyclopentadiene (TPCPD, 1) and dienophiles.

To a solution of TPCPD (1) in $CH_2Cl_2$ (0.5 mL), exo-BCN (6a) in $CH_2Cl_2$ (0.5 mL) was added. The reaction was stirred at room temperature for 5 min. The progress of the reaction was monitored by TLC (hexane/ethyl Acetate 1:1, $R_{f\,product}$=0.4). Upon completion, the reaction mixture was directly loaded on the flash column chromatography and purified using hexane:ethyl Acetate 10:1, to give a white solid product. (Yield: 94%). $^1$H NMR ($CDCl_3$): δ 7.17-7.03 (m, 10H, Ph-H), 6.82-6.70 (m, 10, Ph-H) 3.45 (d, J=4.0 Hz, 2H, —$CH_2$—OH), 2.84-2.77 (m, 2H, —$CH_2$—C≡C—), 2.71-2.65 (br, 2H, —$CH_2$—C≡C—), 2.25-2.22 (br, 1H, —CH—$CH_2$OH), 1.53 (br, 2H, —C—CH—C—), 0.89-0.87 (br, 2H, —$CH_2$—), 0.79-0.77 (br, 2H, —$CH_2$—) $^{13}$C NMR ($CDCl_3$) δ 195.9, 141.7, 140.9, 140.7, 140.3, 138.6, 131.4, 131.0, 130.5, 130.4, 127.2, 127.1, 126.4, 126.2, 125.8, 124.9, 66.6, 30.7, 29.9, 22.6, 21.5. MS calcd. for $C_{38}H_{34}O$ $[M+Na]^+$ 529.2507, found 529.2491.

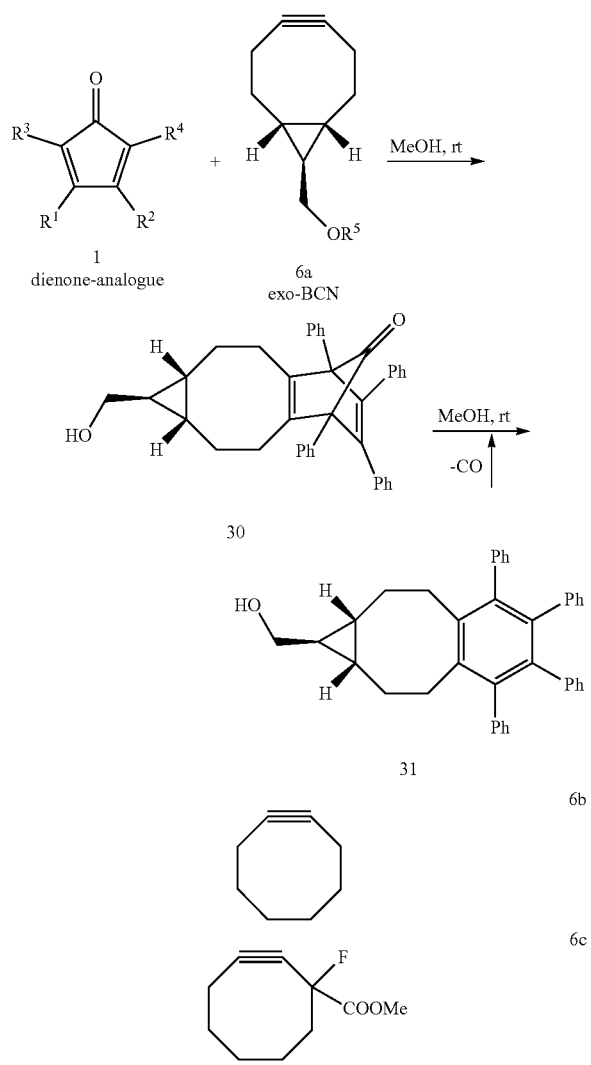

Scheme 12.

Separate solutions of pure TPCPD (1) and pure exo-BCN (6a) (>95-98% by $^1$H-NMR) were prepared in HPLC-grade methanol (acetonitrile, 1,2-dichloroethane, dioxane) at room temperature. The stability of TPCPD in methanol (25 μM) was examined by monitoring its absorption maximum at 335 nm. The solutions containing TPCPD (1, 50 μM, 400 μL) and 18-fold excess of exo-BCN (6a, 900 μM, 400 μL) were added into quartz cuvettes, thoroughly mixed and sealed with a PTFE cap. All kinetic runs were triplicates. Curve fitting was operated in Prism5 software.

Figure 1B:
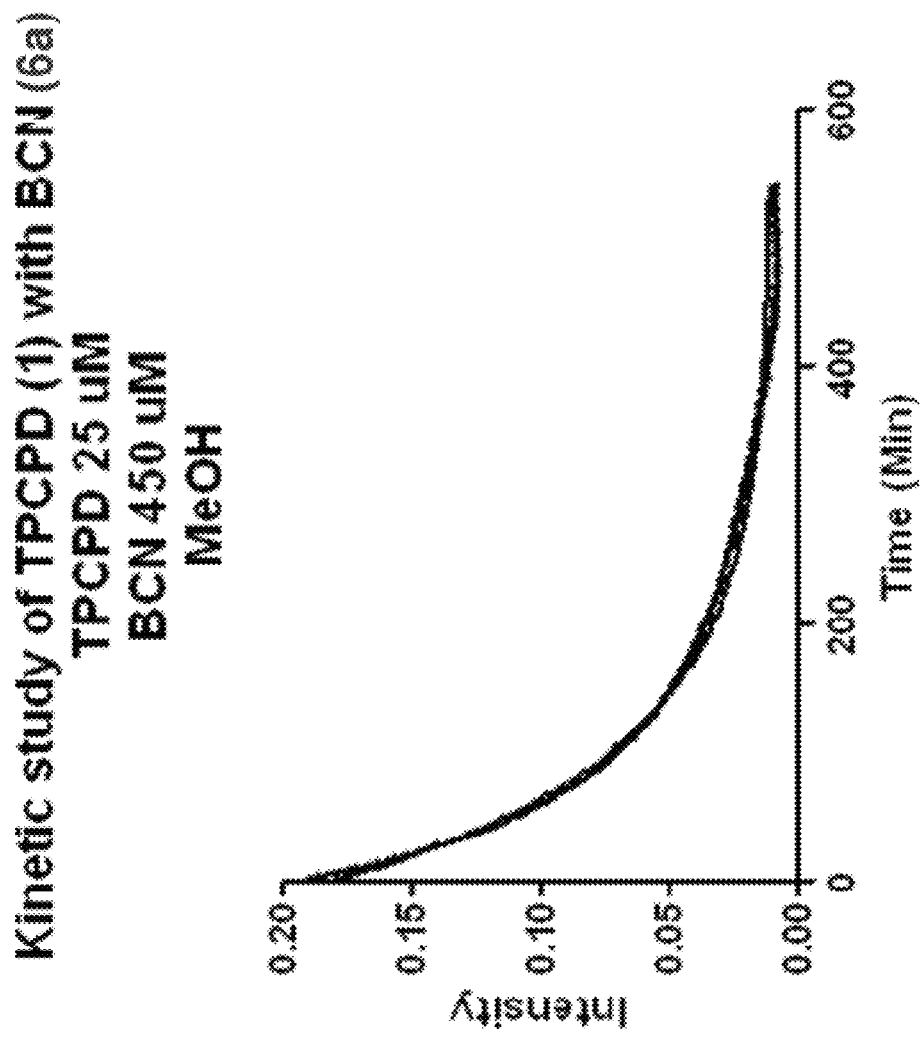
FIG. 1B is a graph showing the kinetics of the reaction of TPCPD and BCN as a function of time.

The reaction between 1 and 6a (Scheme 8) leads to significant changes in the UV-Vis spectrum of TPCPD (30) due to its conversion to the cyclization product 31 (FIG. 1A). Therefore, the reaction can be easily monitored. The reaction performed in dry methanol and the rate constant for the reaction between TPPD and BCN was found to be 0.50 $M^{-1}s^{-1}$ (FIG. 1B). Gas bubble formation was readily apparent, suggesting the release of CO as a byproduct.

It was observed that the reaction rate between TPCPD and BCN was moderately sensitive to the reaction solvent. Methanol, acetonitrile, 1,2-dichloroethene (DCE), and dioxane were chosen for the kinetic studies. The reaction appears to be faster in polar solvents than in nonpolar solvents. For example, half-life ($t_{1/2}$) of the reaction is 99 min in acetonitrile (Table 1), which is faster than in DCE (130 min), and in dioxane (282 min). The reaction in methanol was observed to be faster than in acetonitrile, which clearly indicates that the protic solvent has an enhancing effect on the reaction rate. In order to utilize the reaction under physiological conditions, the reaction rate was measured at physiological temperature, 37° C. The results are shown in Table 1.

TABLE 1

Second order rate constants of TPCPD with BCN in different solvents.

| Solvent | MeOH | | $CH_3CN$ | DCE | Dioxane |
|---|---|---|---|---|---|
| | r.t. | 37° C. | r.t. | r.t. | r.t. |
| Half life* | 55 min | 23 min | 99 min | 130 min | 282 min |
| $k_2$ ($M^{-1}s^{-1}$) | 0.50 ± 0.01 | 1.1 ± 0.002 | 0.26 ± 0.004 | 0.17 ± 0.003 | 0.096 ± 0.001 |

*All half-life values were determined for exo-BCN at 450 μM (6a).

From Table 1, it is observed that the second order rate constant at 37° C. increased about 2 fold compared to the rate at room temperature, 23° C.

Previously reported computational studies have shown the difference in HOMO energies for various cycloocytynes. For example, the HOMO of BCN (6a) is 1.5 kcal $mol^{-1}$ higher than that of cyclooctyne (6b, Scheme 12), presumably resulting in enhanced reactivity. Installing electron-withdrawing groups on cyclooctyne (6b), such as fluorocyclooctyne (6c), decreases the HOMO energy substantially (11.5 kcal/mol). Therefore, the reaction rates for TPCPD and these three cyclooctynes are different. The reaction between TPCPD and BCN finished within 5 min at 50 mM concentration, while the reaction with cyclooctyne finished in 15 min and the reaction with fluorocycolooctyne did not reach completion even after 24 hours at the same concentration. Such results are in qualitative agreement with that of the computational work.

Example 2. Synthesis of Carbon Monoxide-Releasing Molecules

In order to facilitate the monitoring of CO release, dienone analogues 2a-2c were synthesized, which reacted with exo-BCN to release CO and to form fluorescent products 31a-31c. Scheme 13 shows the synthetic route to dienones 2a-2c, and their reactions with exo-BCN 6a to form cycloadducts 31a-31c.

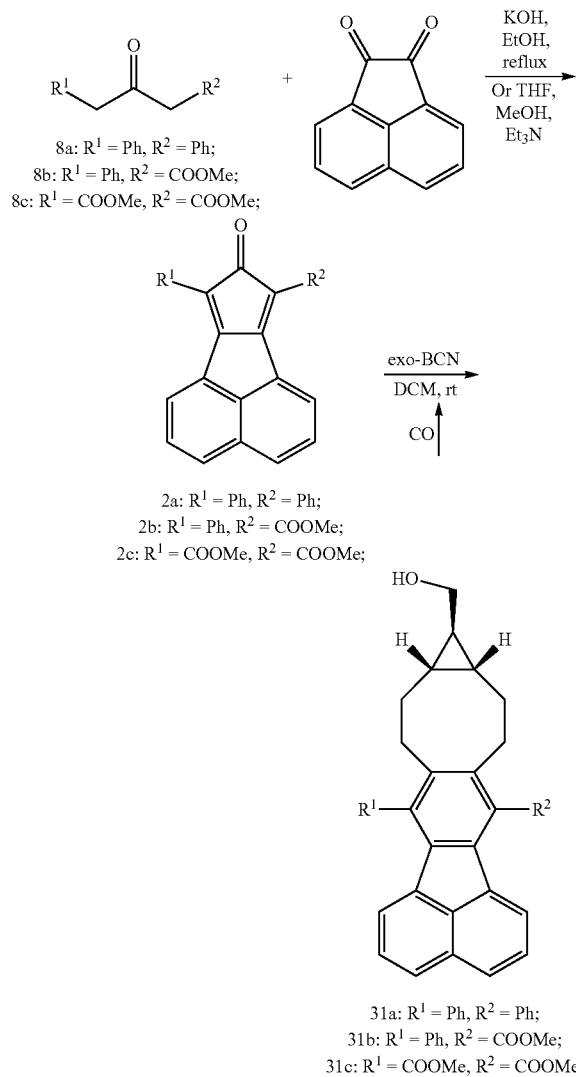

Preparation of Dienone 2a

To a solution of compound 8a (1.0 g, 4.76 mmol) and acenaphthylene-1,2-dione (0.87 g, 1 equiv) in ethanol (20 ml), under reflux was added a solution of KOH (0.28 g, 1 equiv) in ethanol (5 ml). After addition, the reaction mixture was stirred under reflux for additional 2 hrs. On cooling, dark precipitate obtained by filtration, was washed with ethanol to afford compound 2a as a dark brown solid (yield: 85%). $^1$H NMR (400 MHz, CDCl$_3$): δ 8.09 (d, J=7.2 Hz, 2H), 7.89 (d, J=8.0 Hz, 2H), 7.86 (d, J=7.6 Hz, 4H), 7.61 (t, J=7.6 Hz, 2H), 7.55 (t, J=7.6 Hz, 4H), 7.43 (t, J=7.2 Hz, 2H).

Preparation of Dienone 2b

A solution of compound 8b (1.0 g, 5.2 mmol) and acenaphthylene-1,2-dione (0.95 g, 1 equiv) in THF/MeOH (30/10 ml) was treated with Et$_3$N (0.79 g, 1.5 equiv), and the reaction mixture was stirred overnight at room temperature. Thus formed dark green precipitate was filtered, and washed with methanol to give compound 2b as dark green solid (yield: 80%). $^1$H NMR (400 MHz, CDCl$_3$) δ 8.79 (d, J=7.2 Hz, 1H), 8.15-8.03 (m, 2H), 7.95 (d, J=8.0 Hz, 1H), 7.84 (d, J=7.2 Hz, 2H), 7.80 (d, J=7.6 Hz, 1H), 7.64 (t, J=8.0 Hz, 1H), 7.55 (t, J=8.0 Hz, 2H), 7.47 (t, J=7.6 Hz, 1H), 4.03 (s, 3H).

Preparation of Dienone 2c

Compound 2c was synthesized using a method similar to 2b. Compound 2c was obtained in 89% yield as a dark red solid. $^1$H NMR (400 MHz, CDCl$_3$): δ 8.68 (d, J=6.8 Hz, 2H), 8.10 (d, J=8.0 Hz, 2H), 7.80 (t, J=7.2 Hz, 1H), 4.01 (s, 6H).

Preparation of Compound 31a

Compound 31a was synthesized using a method similar to 31. Compound 31a was obtained in 90% yield as a pale yellow solid. $^1$H NMR (400 MHz, CDCl$_3$) δ 7.71-7.54 (m, 10H), 7.47-7.45 (m, 2H), 7.25 (t, J=8.0 Hz, 2H), 3.76 (d, J=6.4 Hz, 2H), 2.81-2.66 (m, 4H), 2.19-2.06 (br, 2H), 1.81-1.52 (br, 2H), 1.27-0.89 (m, 3H).

Preparation of Compound 31b

Compound 31b was synthesized using a method similar to 31. Compound 31b was obtained in 92% yield as a pale yellow solid. $^1$H NMR (400 MHz, CDCl$_3$): δ 7.81 (d, J=8.0 Hz, 1H), 7.76 (d, J=6.8 Hz, 1H), 7.71 (d, J=8.0 Hz, 1H), 7.65-7.53 (m, 5H), 7.43-7.33 (m, 2H), 7.26 (t, J=8.4 Hz, 1H), 6.30 (d, J=6.2 Hz, 1H), 4.15 (s, 3H), 3.74 (br, 2H), 3.21-2.81 (m, 3H), 2.51-2.20 (m, 1H), 1.90-1.54 (m, 3H), 1.01-0.79 (m, 4H). $^{13}$C NMR (101 MHz, CDCl$_3$): δ 171.0, 136.2, 136.0, 134.7, 132.8, 132.7, 129.7, 129.7, 129.1, 129.0, 127.7, 127.7, 127.7, 127.0, 126.4, 122.8, 121.4, 60.4, 59.7, 52.3, 34.5, 29.7, 28.8, 27.9, 13.9.

Preparation of Compound 31c

Compound 31c was synthesized using a method similar to 31. Compound 31c was obtained in 95% yield as a pale yellow solid. $^1$H NMR (400 MHz, CDCl$_3$): δ 7.87 (d, J=8.0 Hz, 2H), 7.74 (d, J=7.2 Hz, 2H), 7.62 (t, J=7.6 Hz, 2H), 4.12 (s, 6H), 3.74 (s, 2H), 3.02 (br, 2H), 2.95-2.80 (m, 2H), 2.34 (br, 2H), 1.41 (s, 2H), 1.21-1.03 (m, 1H), 0.90-0.60 (m, 2H). $^{13}$C NMR (101 MHz, CDCl$_3$): δ 170.2, 134.1, 133.8, 132.6, 130.1, 129.9, 127.9, 127.4, 121.8, 59.5, 52.3, 29.7, 22.2, 16.0, 14.2.

Example 3. Synthesis of Unimolecular Carbon Monoxide-Releasing Molecules

Scheme 14 shows the synthesis of the unimolecular CO releasing compounds.

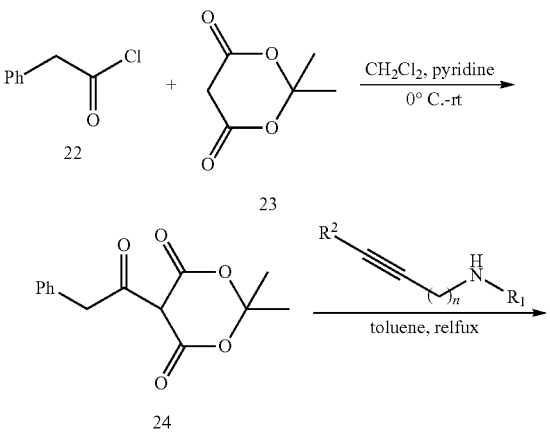

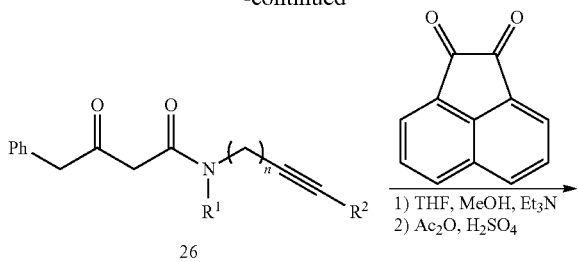

26
26a: R¹ = Me, R² = H, n = 1;
26b: R¹ = iso-Pr, R² = H, n = 2;
26c: R¹ = iso-Pr, R² = Me, n = 2;
26d: R¹ = iso-Pr, R² = TBDPS, n = 1

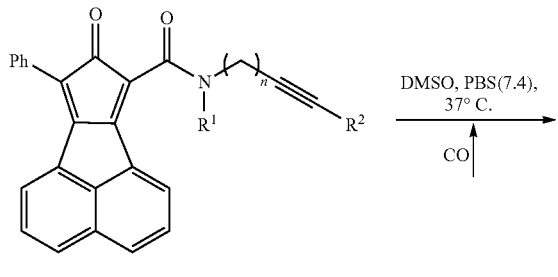

10a: R¹ = Me, R² = H, n = 1;
10b: R¹ = iso-Pr, R² = H, n = 2;
10c: R¹ = iso-Pr, R² = Me, n = 2;
10d: R¹ = iso-Pr, R² = TBDPS, n = 1

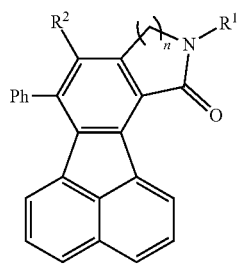

44a: R¹ = Me, R² = H, n = 1;
44b: R¹ = iso-Pr, R² = H, n = 2;
44c: R¹ = iso-Pr, R² = Me, n = 2;
44d: R¹ = iso-Pr, R² = TBDPS, n = 1

Preparation of Compound 24

To a solution of compound 23 (2.0 g, 13.9 mmol) and pyridine (2.2 g, 2 equiv) in CH$_2$Cl$_2$ (50 ml) at 0° C. was added a solution of 22 (3.2 g, 1.5 equiv). After the completion of addition, the reaction was warmed to room temperature, and stirred for an additional 3 hrs. The reaction mixture was then washed successively with 5% HCl solution and brine. The organic layer was dried with anhydrous Na$_2$SO$_4$, filtered and concentrated. Thus obtained residue was purified by column chromatography (Hexane: ethyl acetate=2:1) to afford compound 24 as colorless solid (80% yield). ¹H NMR (400 MHz, CDCl$_3$) δ 15.35 (s, 1H), 7.44-7.29 (m, 5H), 4.45 (s, 2H), 1.74 (s, 6H).

Preparation of Compound 26a

A solution of 24 (0.5 g, 1.9 mmol) and N-methylprop-2-yn-1-amine (0.26 g, 2 equiv) in toluene was heated under reflux for 2 hrs. The reaction mixture was concentrated under vacuum, and the residue was directly purified by column chromatography (Hexane: ethyl acetate=6:1) to afford compound 26a as light brown oil (85% yield). ¹H NMR (400 MHz, CDCl$_3$): δ 7.28-7.19 (m, 5H), 3.92 (s, 2H), 3.67 (s, 2H), 3.34 (s, 2H), 3.19 (s, 3H), 2.25 (s, 1H).

Preparation of Compound 26b

Compound 26b was synthesized using a method similar to 26a. Compound 26b was obtained in 85% yield. ¹H NMR (400 MHz, CDCl$_3$): δ 7.40-7.27 (m, 5H), 3.86 (s, 2H), 3.75-3.64 (m, 1H), 3.59 (s, 2H), 3.45 (t, J=6.8 Hz, 2H), 2.51-2.45 (m, 2H), 2.02 (t, J=6.4 Hz, 1H), 1.12 (d, J=7.6 Hz, 6H).

Preparation of Compound 26c 26c was synthesized using a method similar to 26a. 26c was obtained as a mixture of tautomers in 80% yield. ¹H NMR (400 MHz, CDCl$_3$) δ 15.09 (s, 0.23H), 14.97 (s, 0.29H), 7.38-7.29 (m, 3H), 7.26-7.25 (m, 2H), 5.12 (s, 0.29H), 5.02 (s, 0.34H), 4.74-4.72 (m, 0.29H), 4.59-4.50 (m, 0.25H), 390-3.87 (m, 1H), 3.75-3.70 (m, 0.49H), 3.61-3.50 (m, 2H), 3.38-3.20 (m, 2H), 2.48-2.23 (m, 2H), 1.85-1.72 (m, 2.5H), 1.59 (s, 0.5H), 1.19 (d, J=6.8 Hz, 2H), 1.15 (d, J=6.8 Hz, 2H), 1.11 (d, J=6.8 Hz, 2H).

Preparation of Compound 26d 26d was synthesized using a method similar to 26a. 26d was obtained in 82% yield. ¹H NMR (400 MHz, CDCl$_3$) δ 14.66 (s, 0.3H), 7.76-7.73 (m, 4H), 7.47-7.29 (m, 9H), 7.26-7.24 (m, 2H), 5.13 (s, 0.4H), 4.45 (s, 1.25H), 4.10 (s, 0.5H), 3.88 (s, 1.45H), 3.69 (s, 0.5H), 3.59 (s, 0.9H), 3.55 (s, 0.6H), 3.14-3.00 (m, 3H), 1.10-1.09 (m, 9H).

Preparation of Compound 10a

A solution of 26a (400 mg, 1.7 mmol), acenaphthylene-1,2-dione (318 mg, 1 equiv) in THF/MeOH (10/1 ml) was treated with Et$_3$N (264 mg, 1.5 equiv), and the mixture was stirred at room temperature for 3 hrs, after which the mixture was concentrated under vacuum, and residue was dissolved in acetic anhydride. The resulted solution was cooled to 0° C., and one drop of concentrated sulfuric acid was added. The reaction mixture was stirred for additional 0.5 h at 0° C., and 10 ml methanol was added. The black precipitate ppt obtained was filtered immediately, and washed with cold methanol to afford compound 10a as a mixture of monomer and dimer in 60% yield. ¹H NMR (400 MHz, CDCl$_3$): δ 8.07 (d, J=7.2 Hz, 1H), 8.04 (d, J=7.2 Hz, 1H), 7.98 (d, J=8.0 Hz, 1H), 7.91 (d, J=8.0 Hz, 1H), 7.82 (d, J=7.6 Hz, 2H), 7.71 (t, J=7.6 Hz, 1H), 7.62 (t, J=7.7 Hz, 1H), 7.54 (t, J=7.6 Hz, 2H), 7.45 (t, J=7.4 Hz, 1H), 4.46 (s, 1.3H), 4.27 (s, 0.7H), 3.26 (s, 1H), 3.22 (s, 2H), 2.34 (s, 0.62H), 2.31 (s, 0.33H).

Preparation of Compound 10b

Compound 10b was synthesized using a method similar to 10a. Compound 10b was obtained in 55% yield as a mixture of monomer and dimer. ¹H NMR (400 MHz, CDCl$_3$): δ 8.04 (d, J=7.2 Hz, 1.24H), 7.96-7.94 (m, 2H), 7.90 (d, J=8.0 Hz, 1.27H), 7.81 (d, J=7.6 Hz, 2.49H), 7.71 (t, J=7.6 Hz, 1.27H), 7.62 (t, J=7.6 Hz, 1.29H), 7.54 (t, J=7.6 Hz, 2.34H), 7.44 (t, J=7.4 Hz, 1.22H), 4.73 (s, 0.3H), 4.23-4.06 (m, 1H), 3.69-3.54 (m, 2.63H), 2.83-2.69 (m, 2H), 2.48 (m, 0.64H), 2.10 (s, 1H), 1.87 (s, 0.36H), 1.44 (d, J=6.4 Hz, 1.49H), 1.27 (d, J=6.4 Hz, 6H).

Preparation of Compound 10c

Compound 10c was synthesized using a method similar to 10a. 10c was obtained in 50% yield as a mixture of monomer and dimer. ¹H NMR (400 MHz, CDCl$_3$) δ 8.04 (d, J=7.6 Hz, 2H), 8.00 (d, J=7.1 Hz, 1H), 7.93-7.80 (m, 9H), 7.76-7.71 (m, 0.5H), 7.67 (s, 1.67H), 7.65-7.58 (m, 1.62H), 7.55 (t, J=7.6 Hz, 3H), 7.50-7.44 (m, 3H), 7.41 (s, 6H), 7.36-7.31 (m, 1.5H), 7.27-7.22 (m, 2H), 7.19-7.15 (m, 0.8H), 4.66 (s, 2H), 4.46 (s, 1H), 3.35 (s, 1.5H), 3.30 (s, 3H), 1.15 (s, 6H), 1.02 (s, 3H).

Preparation of Compound 10d

Compound 10d was synthesized using a method similar to 10a. 10d was obtained in 60% yield as a mixture of monomer and dimer. ¹H NMR (400 MHz, CDCl$_3$) δ 9.55 (d, J=8.0 Hz, 1H), 7.90 (d, J=8.0 Hz, 1H), 7.73 (m, 2H), 7.47 (d, J=8.0 Hz, 4H), 7.33 (m, 3H), 7.24 (t, J=8.0 Hz, 4H), 7.19-7.15 (m, 5H), 5.67 (d, J=8.0 Hz, 1H), 3.87 (s, 2H), 3.01 (s, 3H), 1.11 (s, 9H).

Intramolecular DARinv of 10a

A solution of compound 10a in DMSO/PBS (7.4) was incubated at 37° C. for 5 mins, after which the intramolecular DARinv reaction was finished. Then the reaction mixture was extracted with ethyl acetate, and the obtained organic layer was dried with anhydrous $Na_2SO_4$. Filtered and concentrated, the obtained pale yellow solid was characterized by $^1H$ NMR, $^{13}C$ NMR, and MS as the intramolecular DARinv product. $^1H$ NMR (400 MHz, $CDCl_3$) δ 9.42 (d, J=7.2 Hz, 1H), 7.93 (d, J=8.0 Hz, 1H), 7.83 (d, J=8.0 Hz, 1H), 7.77 (t, J=8.0, 1H), 7.64-7.54 (m, 5H), 7.41 (t, J=8.0, 1H), 7.28 (s, 1H), 7.16 (d, J=7.2 Hz, 1H), 4.54 (s, 2H), 3.31 (s, 3H). $^{13}C$ NMR (101 MHz, $CDCl_3$) δ 169.04, 141.33, 140.59, 140.40, 137.09, 136.73, 135.85, 134.67, 132.60, 129.59, 128.93, 128.70, 128.57, 128.38, 128.15, 127.86, 127.63, 127.28, 127.12, 123.32, 122.72, 52.97, 29.48. MS(ESI) $[M+1]^+$ 348.14

Intramolecular DARinv of 10b

A solution of compound 10b in DMSO/PBS (7.4) was incubated at 37° C. for 3 hrs, after which the intramolecular DARinv reaction finished. Then the reaction mixture was extracted with ethyl acetate, and the obtained organic layer was dried with anhydrous $Na_2SO_4$, filtered and concentrated. Thus obtained pale yellow solid was characterized by $^1H$ NMR as the intramolecular DARinv product. $^1H$ NMR (400 MHz, $CDCl_3$): δ 9.27 (d, J=7.2 Hz, 1H), 7.88 (d, J=8.0 Hz, 1H), 7.79 (d, J=8.0 Hz, 1H), 7.71 (t, J=7.6 Hz, 1H), 7.61-7.53 (m, 5H), 7.32 (t, J=8.0 Hz, 1H), 7.08 (s, 1H), 7.04 (d, J=7.2 Hz, 1H), 5.37-5.18 (m, 1H), 3.53 (t, J=6.0 Hz, 2H), 3.05 (t, J=6.0 Hz, 2H), 1.32 (d, J=6.8 Hz, 6H).

Intramolecular DARinv of 10c

A solution of compound 10b in DMSO/PBS (7.4) was incubated at 37° C. for 24 hrs, after which the intramolecular DARinv reaction was finished. Then the reaction mixture was extracted with ethyl acetate, and the obtained organic layer was dried with anhydrous $Na_2SO_4$. Filtered and concentrated, the obtained pale yellow solid was characterized by $^1H$ NMR as the intramolecular DARinv product. $^1H$ NMR (400 MHz, $CDCl_3$) δ 9.12 (d, J=8.0 Hz, 1H), 7.83 (d, J=8.4 Hz, 1H), 7.73 (d, J=8.4 Hz, 1H), 7.68 (t, J=8.0 Hz, 1H), 7.63-7.54 (m, 3H), 7.36 (d, J=8.0 Hz, 2H), 7.24 (t, J=8.0 Hz, 1H), 6.32 (d, J=8.0 Hz, 1H), 5.29-5.26 (m, 1H), 3.57-3.46 (m, 2H), 3.05-2.94 (m, 2H), 2.12 (s, 3H), 1.33 (d, J=6.8 Hz, 6H).

Intramolecular DARinv of 10d

A solution of compound 10b in DMSO/PBS (7.4) was incubated at 37° C. for 5 mins, after which the intramolecular DARinv reaction finished. Then the reaction mixture was extracted with ethyl acetate, and the obtained organic layer was dried with anhydrous $Na_2SO_4$, filtered and concentrated. Thus obtained pale yellow solid was characterized by 1H NMR as the intramolecular DARinv product. $^1H$ NMR (400 MHz, $CDCl_3$) δ 9.55 (d, J=8.0 Hz, 1H), 7.90 (d, J=8.0 Hz, 1H), 7.73 (m, 2H), 7.47 (d, J=8.0 Hz, 4H), 7.33 (m, 3H), 7.24 (t, J=8.0 Hz, 4H), 7.19-7.15 (m, 5H), 5.67 (d, J=8.0 Hz, 1H), 3.87 (s, 2H), 3.01 (s, 3H), 1.11 (s, 9H).

Example 4. Synthesis of Unimolecular Carbon Monoxide Releasing Molecule 51

Scheme 15 shows the synthesis of the unimolecular CO releasing molecules.

Preparation of Compound 46

To a solution of compound 45 (2.0 g, 13.2 mmol) in MeOH (30 ml) was added HCl solution (0.2 ml, 35%), and the resulting mixture was heated under reflux overnight. Then the mixture was concentrated, and the residue was dissolved in ethyl acetate (50 ml), and washed with $NaHCO_3$, brine successively. The organic layer was dried over anhydrous $Na_2SO_4$, then filtered and concentrated, and the pale yellow solid was used for next step without further purification (yield 90%). $^1H$ NMR (400 MHz, $CDCl_3$): δ 7.36 (s, 1H), 7.23 (t, J=7.6 Hz, 1H), 7.12 (d, J=8.0 Hz, 1H), 6.97 (d, J=8.0 Hz, 1H), 6.91 (td, J=7.6, 1.0 Hz, 1H), 3.78 (s, 3H), 3.71 (s, 2H).

Preparation of Compound 47

A mixture of 46 (1.0 g, 6.0 mmol), $K_2CO_3$ (1.3 g, 9.0 mmol), and 3-bromoprop-1-yne (1.4 g, 12 mmol) in $CH_3CN$ (40 ml) was heated under reflux for 1 h. The reaction mixture was filtered, and the filtrate was concentrated. The red oil obtained was purified over silica gel to afford the compound 47 (0.9 g, 80%) as yellow oil. $^1H$ NMR (400 MHz, $CDCl_3$): δ 7.28 (t, J=7.6 Hz, 1H), 7.23 (d, J=7.6 Hz, 1H), 7.04-6.97 (m, 2H), 4.73 (d, J=2.4 Hz, 2H), 3.72 (s, 3H), 3.69 (s, 2H), 2.51 (t, J=2.4 Hz, 1H).

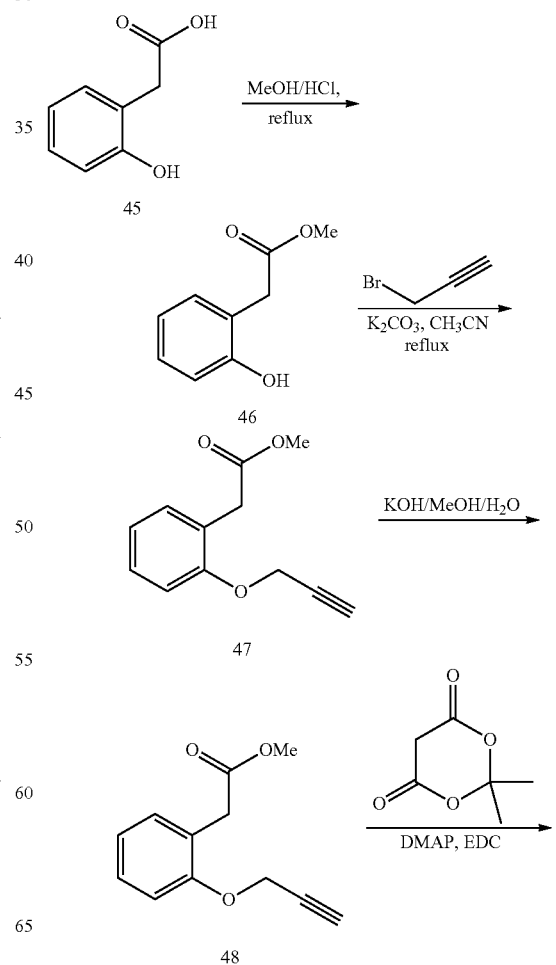

Scheme 15.

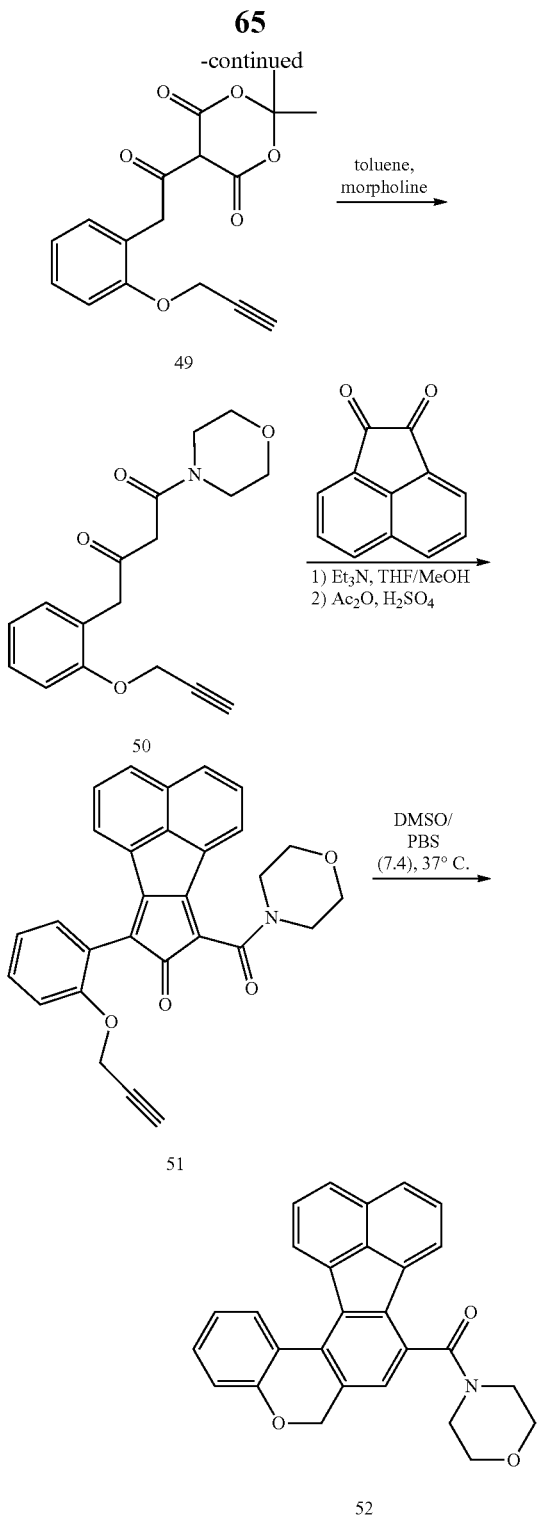

Preparation of Compound 48

A solution of compound 47 (1.0 g, 5 mmol), and KOH (0.4 g, 7.5 mmol) in MeOH/H$_2$O (20/5 ml) was stirred at room temperature overnight. The reaction mixture was poured into ice water, and was extracted with ethyl acetate. The aqueous layer was acidified with HCl (10%) to pH 2, and extracted in ethyl acetate. The combined organic layer was dried over anhydrous Na$_2$SO$_4$, followed by filtration and concentration which afforded compound 48 as a white solid (0.8 g, 90%). $^1$H NMR (400 MHz, CDCl$_3$): δ 7.30 (t, J=8.0 Hz, 1H), 7.24 (d, J=8.0 Hz, 1H), 7.03 (m, 2H), 4.74 (d, J=4.0 Hz, 2H), 3.71 (s, 2H), 2.51 (t, J=4.0 Hz, 1H).

Preparation of Compound 49

To a mixture of compound 48 (0.5 g, 2.6 mmol), 2,2-dimethyl-1,3-dioxane-4,6-dione (0.45 g, 3.1 mmol) and DMAP (0.38 g, 3.1 mmol) in DCM (40 ml) at 0° C. was added EDC (0.48 g, 3.1 mmol) portion wise. The resulting solution was warmed to room temperature, and stirred for overnight. The reaction mixture was washed with 5% KOH solution, and the combined aqueous solution was acidified with HCl to pH 2, and extracted with ethyl acetate. The obtained organic layer was washed with brine, and dried over anhydrous Na$_2$SO$_4$, then filtered and concentrated, and the obtained pale yellow solid was recrystallized from ethyl acetate and hexane as a pale yellow solid (0.6 g, 75%). $^1$H NMR (400 MHz, CDCl$_3$): δ 7.17-7.06 (m, 1H), 6.99 (m, 1H), 6.84 (m, 2H), 4.47 (s, 2H), 4.10 (s, 2H), 1.45 (s, 1H), 1.45 (s, 6H).

Preparation of Compound 50

A solution of compound 49 (400 mg, 1.3 mmol) and morpholine (220 mg, 2.5 mmol) in toluene (10 ml) was heated under reflux overnight. The reaction mixture was concentrated, and the obtained brown oil was purified over silica gel column to afford the title compound as a pale yellow oil (310 mg, 80%). $^1$H NMR (400 MHz, CDCl$_3$): δ 7.32-7.22 (m, 1H), 7.17 (m, 1H), 6.97 (m, 2H), 4.69 (d, J=4.0 Hz, 2H), 3.77 (s, 2H), 3.67-3.55 (m, 8H), 3.32-3.24 (m, 2H), 2.52 (t, J=4.0 Hz, 1H).

Preparation of Compound 51

Compound 51 was synthesized by a method similar to 10a. Compound 51 was obtained in 60% yield as a dark solid. $^1$H NMR (400 MHz, CDCl$_3$): δ 8.11 (d, J=8.0 Hz, 1H), 7.97 (d, J=8.0 Hz, 1H), 7.87 (dd, J=8.0, 4.0 Hz, 1H), 7.69 (t, J=8.0 Hz, 1H), 7.65-7.57 (m, 2H), 7.54-7.49 (m, 1H), 7.46 (t, J=8.0 Hz, 1H), 7.23 (d, J=8.0 Hz, 1H), 7.16 (t, J=7.6 Hz, 1H), 4.72 (d, J=4.0 Hz, 2H), 3.86 (br, 4H), 3.78 (br, 2H), 3.59 (br, 2H), 2.52 (t, J=4.0 Hz, 1H).

Intramolecular DARinv of 51

A solution of compound 51 in DMSO/PBS (7.4) was incubated at 37° C. for 16 hours, after which the intramolecular DARinv reaction was finished. Then the reaction mixture was extracted with ethyl acetate, and the obtained organic layer was dried with anhydrous Na$_2$SO$_4$, then filtered and concentrated, and the obtained pale yellow solid was characterized by $^1$H NMR as the intramolecular DARinv product 52. $^1$H NMR (400 MHz, CDCl$_3$): δ 8.51 (d, J=7.2 Hz, 1H), 8.41 (d, J=7.6 Hz, 1H), 7.92 (m, 3H), 7.70-7.63 (t, J=7.6 Hz, 1H), 7.60 (t, J=7.7 Hz, 1H), 7.41 (t, J=7.6, 1H), 7.26-7.18 (m, 2H), 7.11 (s, 1H), 5.10 (dd, J=12 Hz, 2H), 4.23-3.72 (m, 4H), 3.70-3.14 (m, 4H).

Example 5. CO-Deoxy-Myoglobin Assay

Figure 2:
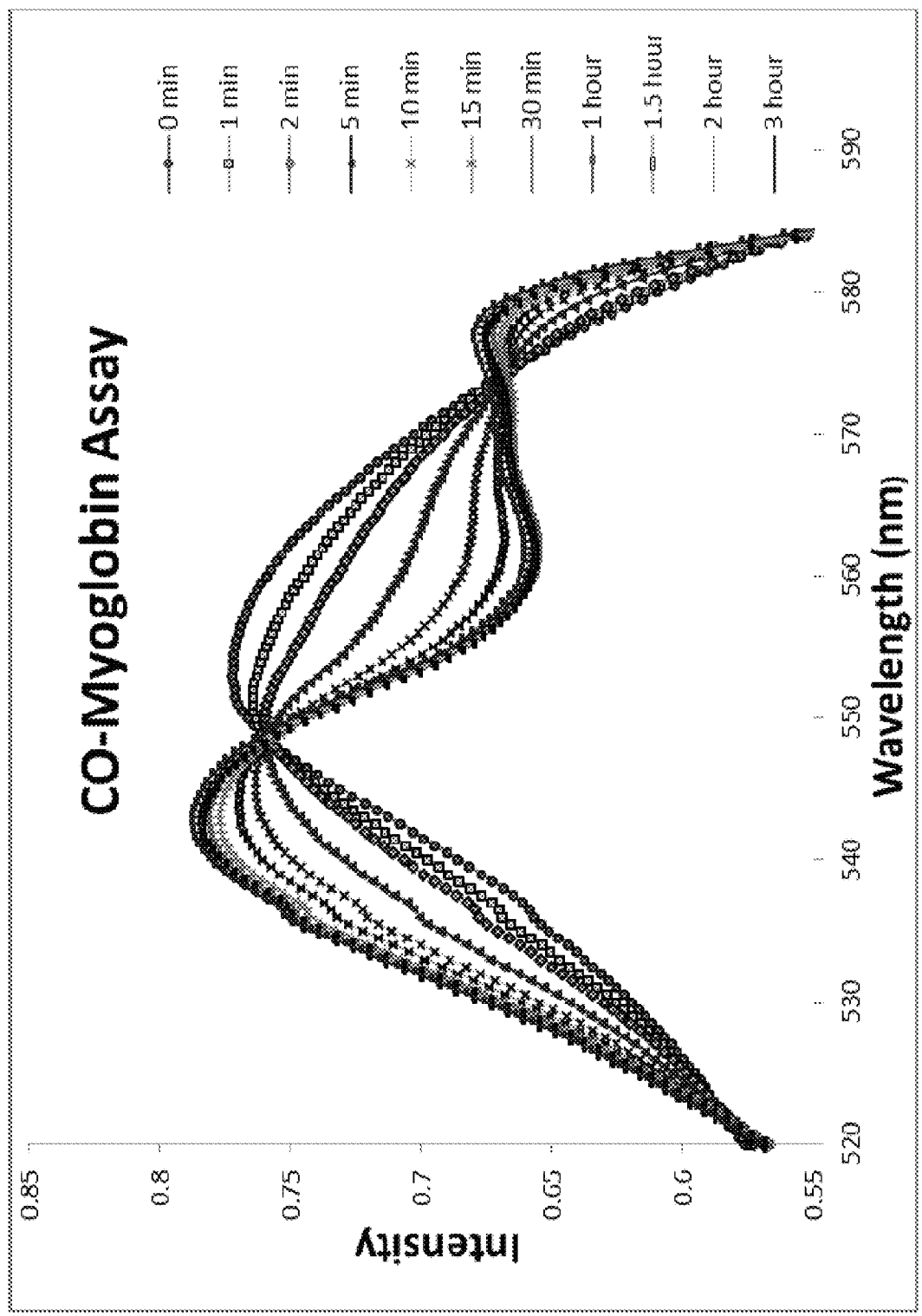
FIG. 2 shows a UV-Vis absorption spectrum showing the conversion of deoxy-myoglobin (Mb) to carbon monoxide myoglobin (MbCO) due to the release of CO from the reaction of TPCPD and BCN.

The deoxy-myoglobin assay was performed to confirm the formation of CO. If free CO is released from the click reaction, it is expected that CO would convert deoxy-Mb to Mb-CO with a concomitant change of its UV spectrum. Deoxy-Mb has an affinity for CO which is 230 fold stronger than for 02. The conversion can be monitored by observing the change in the Q-bands of the heme group in both deoxy-Mb (540 nm) and Mb-CO (540 nm and 580 nm) using UV-vis spectroscopy. FIG. 2 shows that CO release takes place during the quick cyclization and oxidation steps. This spectroscopic change is consistent with what has been observed with other carbon monoxide releasing molecules (CORMs).

A CO detection experiment was also carried out in a 1 L glass jar equipped with a commercially available CO detector and reaction vessel. Five minutes after the addition of BCN (final concentration 100 mM) to a TPCPD solution, the CO detector indicated that detectable levels of CO had been reached in the closed container.

Example 6. Cytotoxicity Assay

Figure 3A:
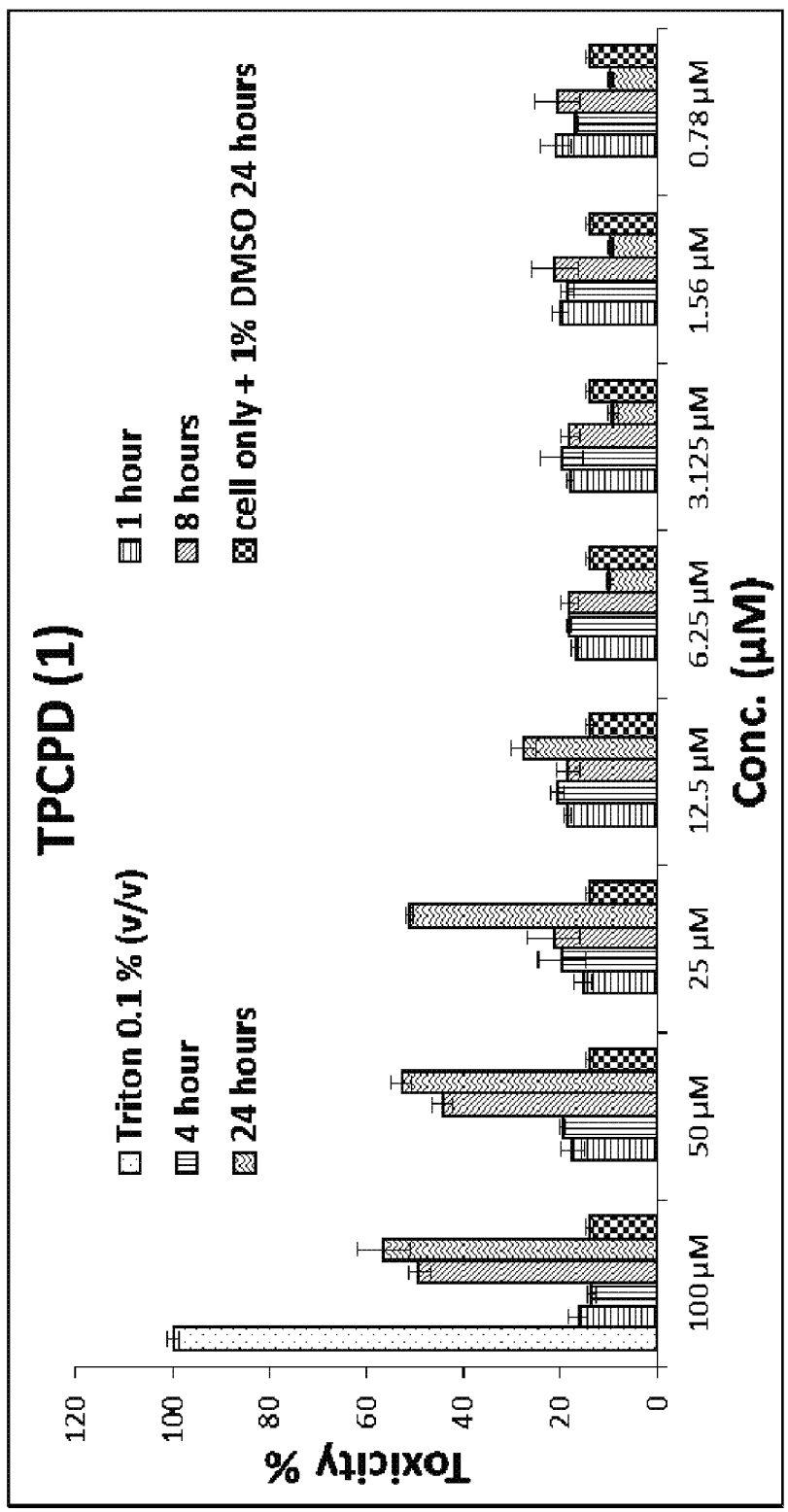
FIG. 3A shows a graph showing the percent cytotoxicity as a function of concentration for TPCPD.
Figure 3B:
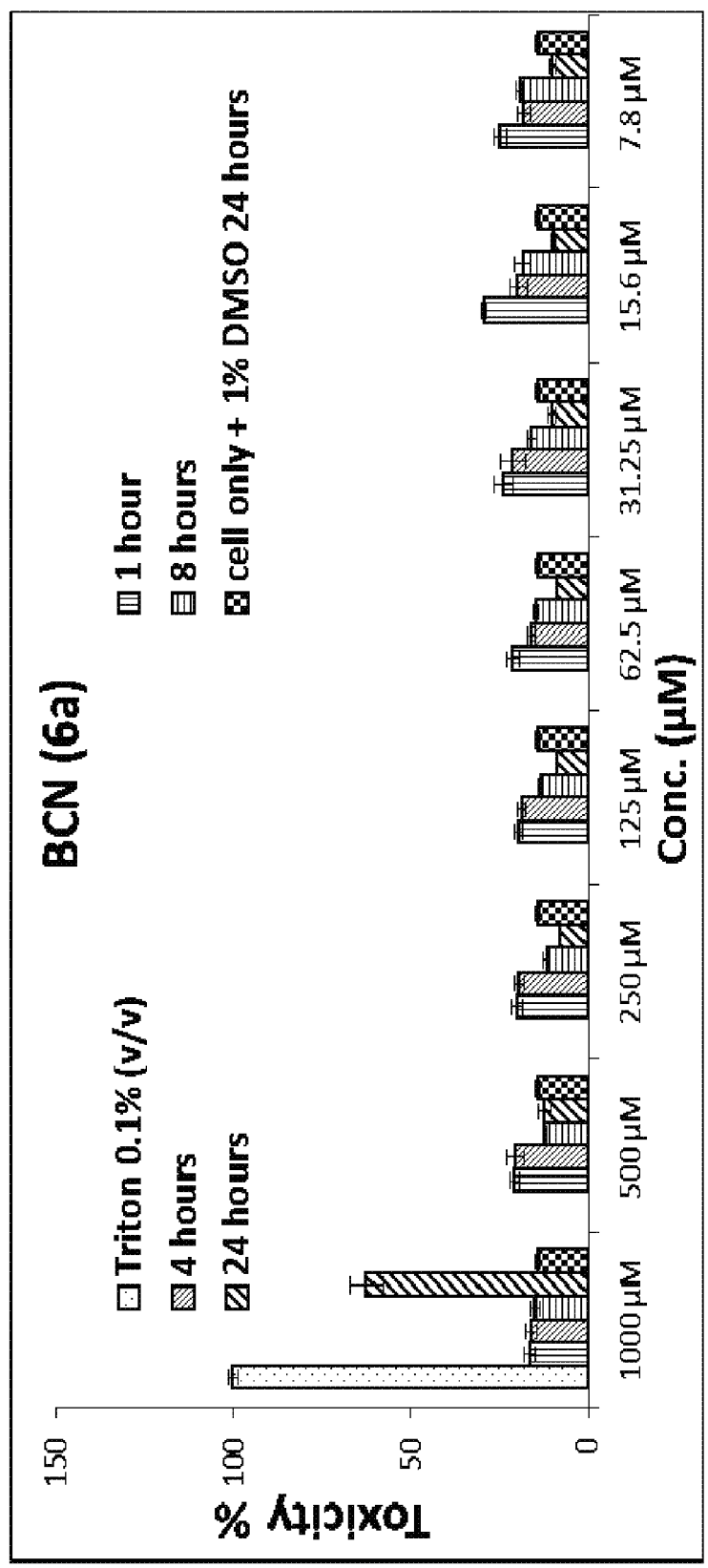
FIG. 3B shows a graph showing the percent cytotoxicity as a function of concentration for BCN.
Figure 3C:
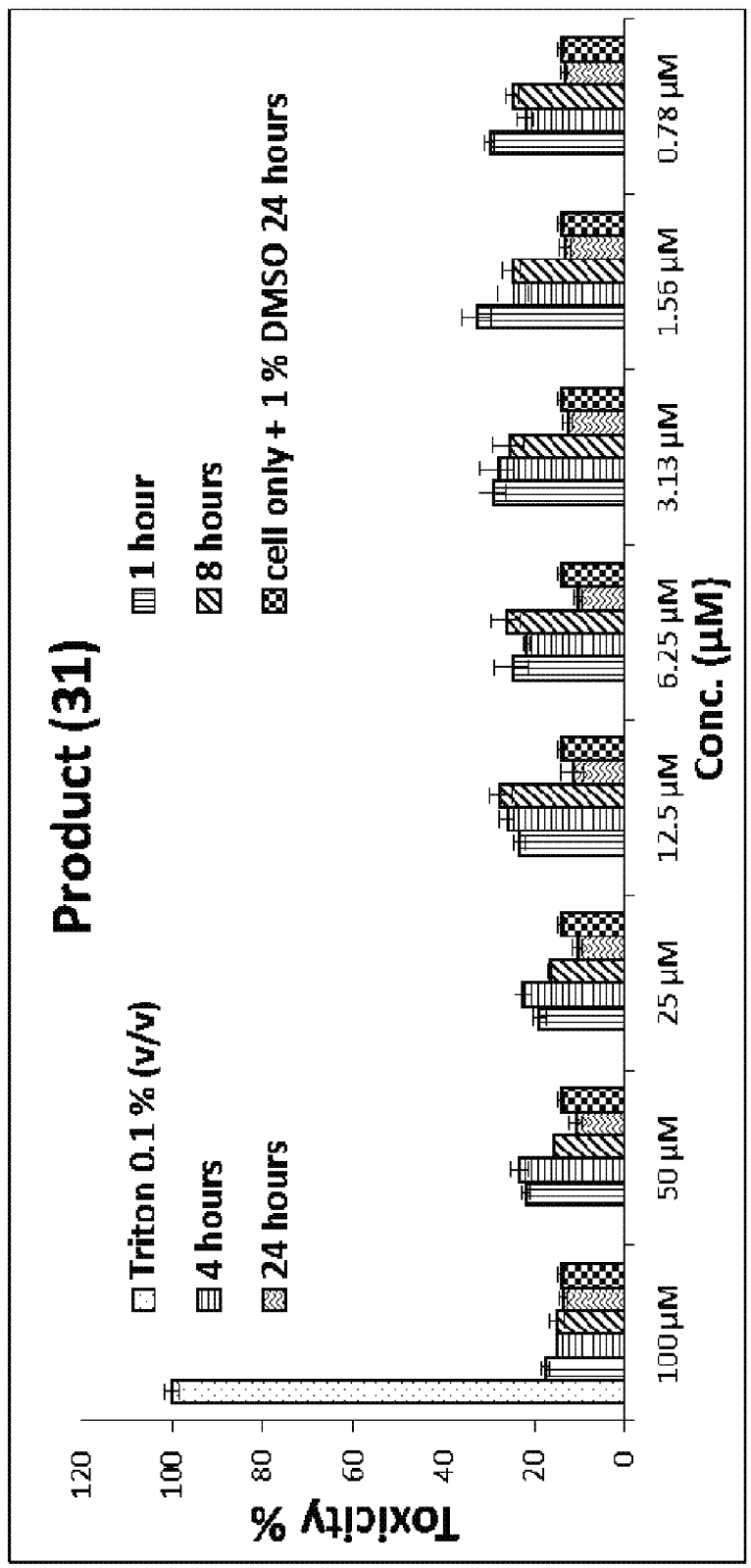
FIG. 3C shows a graph showing the percent cytotoxicity as a function of concentration of the product of the reaction of TPCPD and BCN.

In order to assess the cytotoxic effect of the reactants, 1 and 6a, as well as product 31, on RAW cells, the cytotoxicity test WST-1 was performed to examine induction by TPCPD (1) and BCN (6a) over varying concentrations and periods of time (FIGS. 3A-3C).

RAW264.7 cell were seeded in 6-well plates and incubated overnight. Cells were then stimulated with LPS (10 mg/mL) for 1 h. TPCPD (1) and BCN (6a) (different concentrations) were added to well after 1 hr LPS treatment (same for all wells). As a control, the product (31) was used at same concentration as the anti-inflammation test to confirm that the suppression of TNF-α is result of CO instead of the reagent (or product) themselves (compounds 1, 6a, and 31). TNF-α secretion in the medium was measured with an eBioscience kit (mouse TNF-α ELISA kit, eBioscience, San Diego, Calif., USA).

Different concentrations of each molecule were assessed: from 0.78 to 100 µM for 1 and 31 and 7.8 to 1000 µM for 6a. Different time points were assessed (1 h, 4 h, 8 h and 24 h). Triton 0.1% was used as a positive control of cytotoxicity and the subsequent value was established as 100% of cytotoxicity.

After 1 h and 4 h of treatment none of the compounds led to any cytotoxicity within the concentration range studied. At 8 h, 1 (FIG. 3A) displayed a toxicity of 44% and 49% for the higher concentrations (50 µM and 100 µM). Neither 6a (FIG. 3B) and nor the product (FIG. 3C) displayed any sign of cytotoxicity within the concentration range studied. At 24 h, 1 exhibited cytotoxicity of more than 50% for concentrations higher than 12.5 µM. 6a displayed cytotoxicity of 60% only at 1 mM and the product 31 was not cytotoxic within the concentration ranged tested.

Example 7. Water-Solubility and Cell Viability Improvement

In order to improve the water solubility and minimize the effect of the reactants on cell viability, 1 and 6a were modified with mannose to give water soluble 57 (TPCPD-M) and 61 (BCN-M) as described in Scheme 16.

Figure 4:
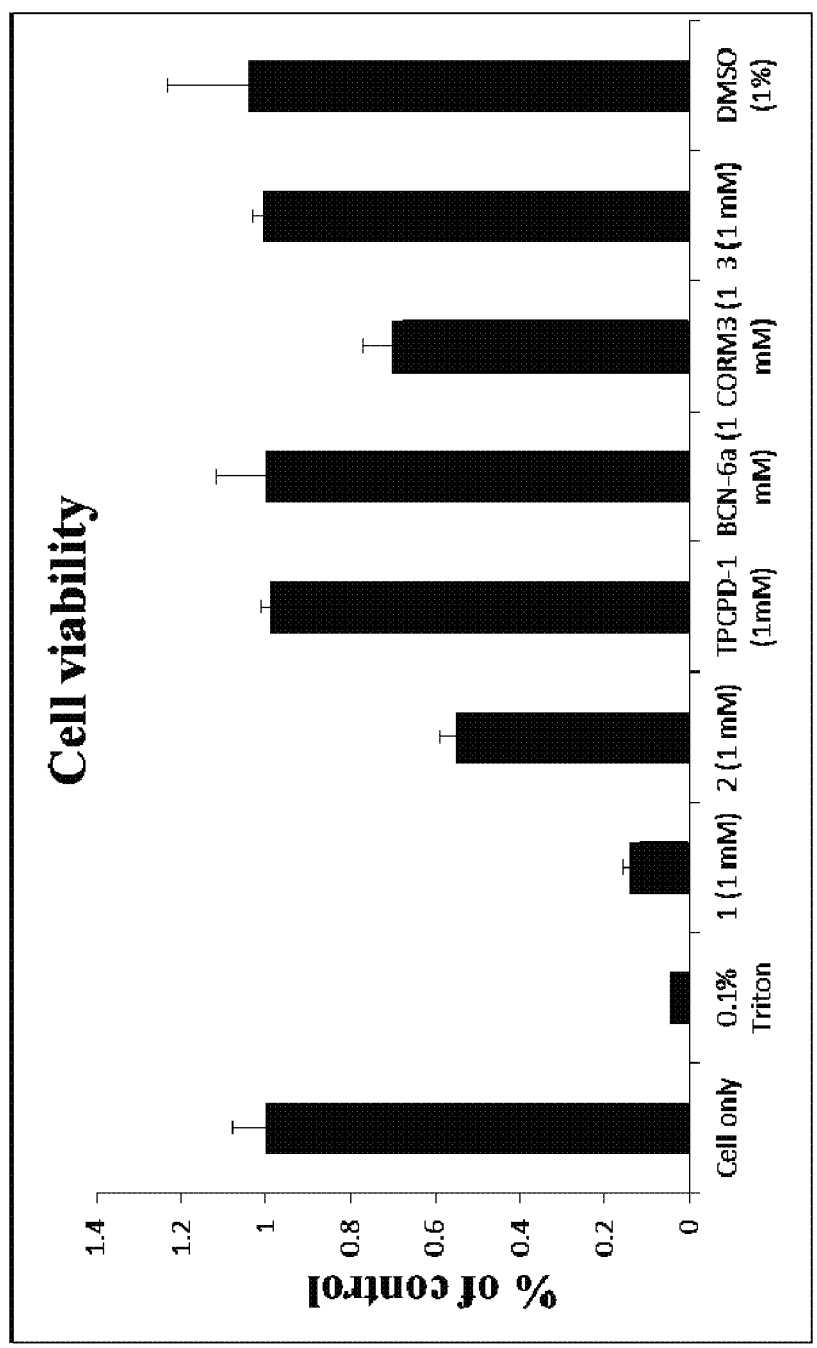
FIG. 4 shows a graph showing cell viability (percent of control) as a function of various dienes, dienophiles, and cycloaddition products.

The cytotoxicity test, MTT assay, was performed to define the concentration using TPCPD-M (57, 1 mM) and BCN-M (61, 1 mM) (FIG. 4). After 24 h of treatment, none of the compounds led to any cytotoxicity within 1 mM concentration. As a control, CORM3 at 1 mM concentration (FIG. 4) displayed a toxicity with a 30% decrease in cell viability for 1 mM concentration.

Preparation of 54

To a 10 mL reaction tube equipped with a stir bar, 3,4-bis(4-hydroxyphenyl)-2,5-diphenylcyclopenta-2,4-dienone (53, 50 mg, 0.12 mmol) in $CH_3CN$ (2 mL), propargyl bromide (179 mg (80 wt. % in toluene), 1.2 mmol), $K_2CO_3$ (50 mg, 0.36 mmol), and NaI (1.8 mg, 0.012 mmol) were added. The vessel was sealed and the mixture was stirred in an oil bath at 80° C. for 2 hours. The progress of the reaction was monitored by TLC (hexane/ethyl acetate 8:1, $R_{fproduct}$=0.5). Upon completion, the seal was removed and the reaction solution was cooled to room temperature. The reaction mixture was filtered. The filtrate was collected and dried under vacuum to give a crude product. The crude product was directly loaded on the flash column for chromatography (eluted by hexane/ethyl Acetate 10:1) to give dark brown solid product 54 (50 mg, yield: 84%). $^1$H NMR ($CDCl_3$): δ 7.27 (br, 10H), 6.89 (d, J=8 Hz, 4H), 6.81 (d, J=8 Hz, 4H) 4.68 (m, 4H), 2.56 (S, 2H), $^{13}$C NMR ($CDCl_3$): δ 200.1, 157.8, 153.7, 131.1, 131.0, 130.1, 128.0, 127.3, 126.1, 124.9, 114.3, 78.1, 15.7, 55.8. MS calcd. For $C_{35}H_{24}O_3$ $[M+H]^+$ 493.1804, found 493.1807.

Preparation of TPCPD-Man(OAc) (56)

To a solution of 54 (50 mg, 0.1 mmol) in 1 mL $CH_3CN$, compound 55 (113 mg, 0.22 mmol) was added, followed by the addition of CuI (0.1 eq.), DBU (0.4 eq.) and sodium ascorbate (0.5 eq.). Then the solution was stirred at room temperature overnight. The progress of the reaction was monitored by TLC (hexane/ethyl acetate 2:1, $R_{fproduct}$=0.4) Upon completion; the reaction mixture was directly loaded on the flash column for chromatography (eluted by hexane/ethyl acetate 4:1) to give dark brown solid product 56. (98 mg, yield: 65%). $^1$H NMR ($CDCl_3$): δ 7.82 (s, 2H, NH), 7.22 (br, 10H), 6.85 (d, J=8 Hz, 4H) 6.80 (d, J=8 Hz, 4H), 5.34-5.24 (m, 8H), 5.14 (s, 4H), 4.85 (s, 2H), 4.58-4.55 (m, 4H), 4.27-4.23 (m, 2H), 4.10-4.03 (m, 4H), 3.91-3.88 (m, 4H), 3.80-3.77 (m, 2H), 3.647-3.60 (m, 4H), 2.12 (s, 6H), 2.07 (s, 6H), 2.01 (s, 6H), 1.96 (s, 6H). $^{13}$C NMR ($CDCl_3$): δ 199.7, 170.6, 160.0, 169.9, 169.6, 158.6, 153.8, 143.3, 131.1, 131.0, 130.0, 127.9, 127.2, 125.7, 124.7, 124.03, 114.1, 97.6, 77.3, 77.0, 76.7, 70.6, 70.5, 69.9, 69.5, 69.4, 69.0, 68.40, 67.3, 66.0, 62.3, 61.8, 50.3, 20.8, 20.7, 20.6. MS calcd. For $C_{75}H_{86}N_6O_{27}$ $[M+H]^+$ 1503.5619, found 1503.5627.

Preparation of TPCPD-M (57)

To a solution of 56 (50 mg, 0.033 mmol) in 0.5 mL THF cooled to 0° C., NaOH aqueous solution (0.2 M, 0.5 mL) was added dropwise. Then this mixture was stirred for 1 h at 0° C. The progress of the reaction was monitored by TLC (hexane/ethyl acetate 2:1, starting material 56, $R_f$=0.2). Upon completion, $H^+$ resin was added to adjust the pH to 7. The reaction mixture was filtered. The filtrate was collected and dried under vacuum to give a crude product. The crude product was directly loaded on P2 column for chromatography (eluted by $H_2O$) to give dark brown solid product 57 (34 mg, yield: 90% after lyophilization).

Scheme 16.
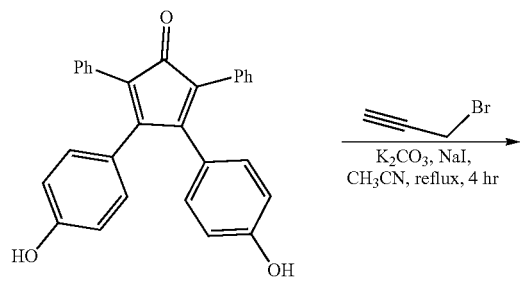
53
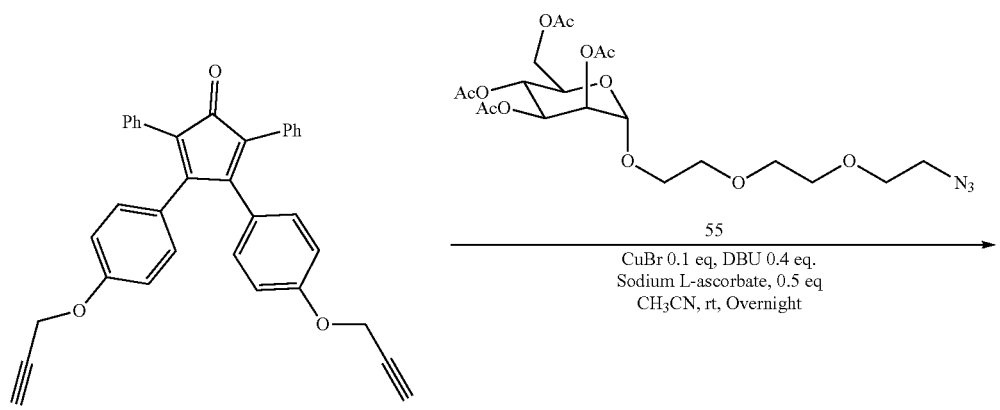
54
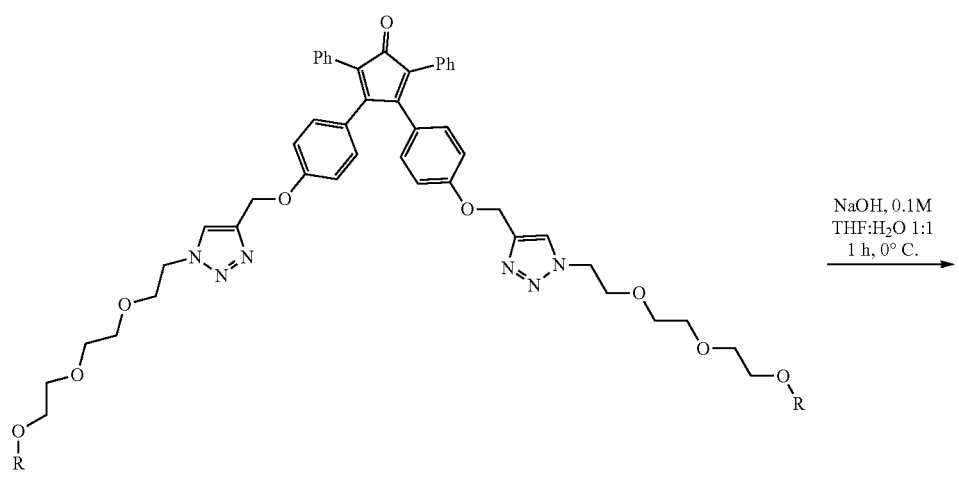
56
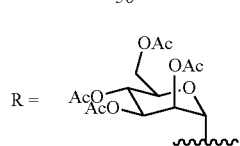

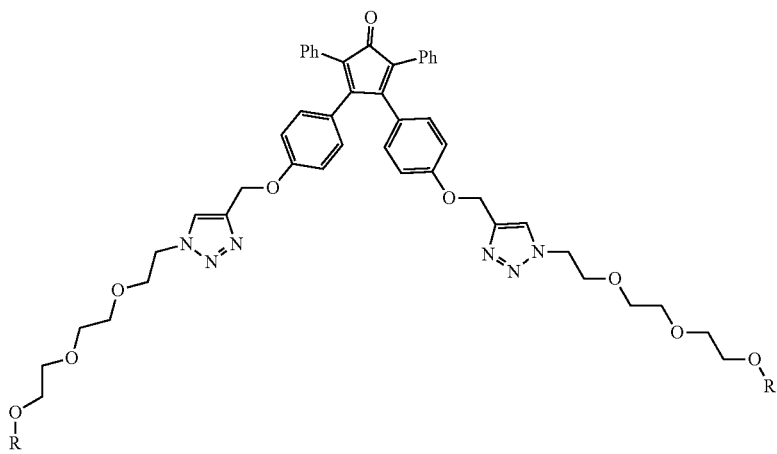
57
TPCPD-M
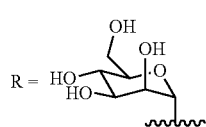
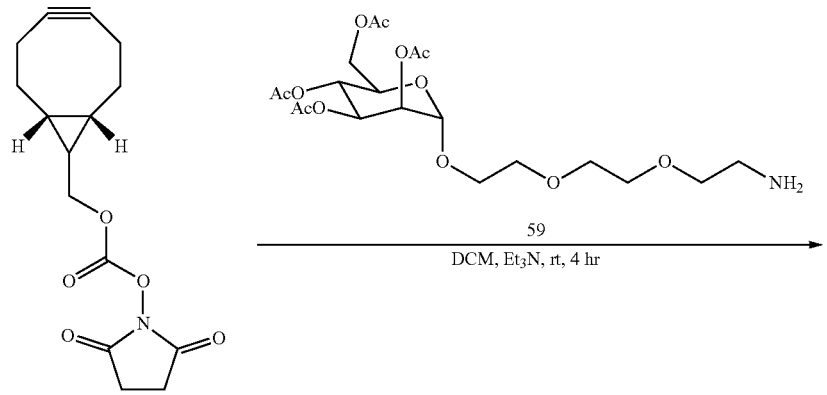
59
————————→
DCM, Et₃N, rt, 4 hr
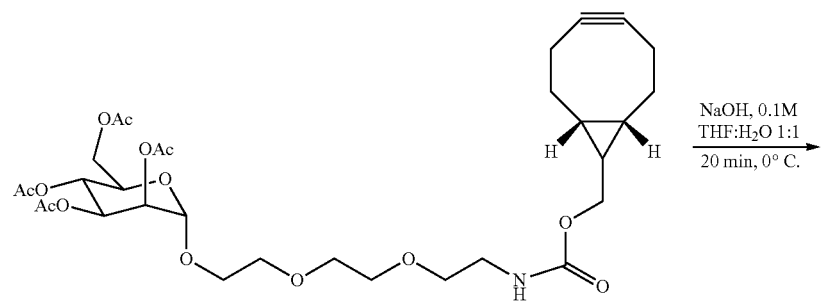
60
NaOH, 0.1M
THF:H₂O 1:1
————————→
20 min, 0° C.

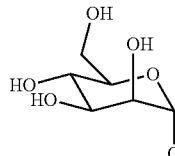

61

57: $^1$H NMR (CD$_3$OD): δ 8.12 (s, 2H), 7.24-7.18 (m, 8H), 6.87 (br, 10H), 5.14 (s, 4H), 4.78 (m, 3H), 4.61-4.59 (m, 5H), 3.91-3.89 (m, 5H), 3.82-3.77 (m, 8H), 3.72-3.68 (m, 6H), 3.67-3.35 (m, 23H). $^{13}$C NMR (CD$_3$OD): δ 197.4, 160.2, 155.8, 144.5, 132.6, 132.3, 131.3, 129.0, 128.4, 127.1, 126.3, 126.2, 115.5, 101.7, 74.6, 72.6, 72.1, 71.6, 71.5, 71.4, 70.4, 68.6, 67.7, 62.9, 62.4, 51.5, 49.6, 49.4, 49.2, 49.0, 48.8, 48.6, 48.4. MS calcd. For C$_{59}$H$_{70}$N$_6$O$_{19}$ [M−H]$^+$ 1165.4617, found 1165.4538.

Preparation of BCN-Man(OAc) (60)

To a solution of 58 (50 mg, 0.17 mmol) in 2 mL DCM, 59 (123 mg, 0.25 mmol) was added 1 mL DCM, followed by the addition of Et$_3$N (52 mg, 0.52 mmol). This mixture was stirred at room temperature for 4 h. The progress of the reaction was monitored by TLC (hexane/ethyl acetate 1:1, R$_{fproduct}$=0.2). Upon completion, the reaction mixture was directly loaded on a flash column for chromatography (hexane/ethyl acetate 2:1) to give colorless oil product 60. (111 mg, yield: 68%). $^1$H NMR (CDCl$_3$): δ 5.37-5.15 (m, 8H), 4.84 (d, J=15.7 Hz, 2H), 4.27 (dd, J=12.2, 4.8 Hz, 2H), 4.17-4.00 (m, 4H), 3.80 (dd, J=12.2, 7.4 Hz, 1H), 3.75-3.56 (m, 8H), 3.54 (t, J=5.0 Hz, 2H), 3.36 (d, J=4.7 Hz, 2H), 2.29-2.16 (m, 4H), 2.13 (d, J=7.3 Hz, 3H), 2.08 (s, 3H), 2.02 (s, 3H), 1.97 (s, 3H), 1.56 (d, J=10.3 Hz, 2H), 1.33 (dd, J=17.7, 7.7 Hz, 1H), 0.90 (dd, J=22.0, 12.4 Hz, 2H). MS calcd. For C$_{31}$H$_{45}$NO$_{14}$ [M+H]$^+$ 656.2918, found 656.2922.

Preparation of BCN-M (61)

To a solution of 60 (50 mg, 0.076 mmol) in 0.5 mL THF cooled to 0° C., NaOH aqueous solution (0.2 M, 0.5 mL) was added dropwise. Then this mixture was stirred for 20 min at 0° C. The progress of the reaction was monitored by TLC (hexane/ethyl acetate 1:1, R$_{fproduct}$=0.4). Upon completion, H$^+$ resin was added to adjust the pH to 7. The reaction mixture was filtered, and the filtrate was collected and dried under vacuum to give a crude product. The crude product was directly loaded on a P2 column for chromatography (eluted by H$_2$O) to give dark brown solid product 31. (25 mg, yield: 70% after lyophilization). $^1$H NMR (D$_2$O): δ 4.23 (d, J=7.8 Hz, 2H), 4.04-3.96 (m, 1H), 3.95-3.82 (m, 2H), 3.82-3.60 (m, 8H), 3.37 (d, J=6.5 Hz, 2H), 2.28 (dd, J=24.4 Hz, 12.4 Hz, 4H), 1.63 (d, J=10.6 Hz, 2H), 1.43 (d, J=8.7 Hz, 1H), 1.10-0.93 (m, 2H). MS calcd. For C$_{23}$H$_{37}$NO$_{10}$ [M−H]$^+$ 486.2339, found 486.2342.

Example 8. Synthesis of Targeted CO Releasing Molecules

In order to achieve the targeted delivery of CO, 1 and 6a were modified with folic acid to give folic conjugates 52 (TPCPD-F) and 55 (BCN-F) as described in Scheme 17. It should be noted that the conjugate with two folate molecules conjugated to one TPCPD work the same in targeted delivery of such a reagent.

Scheme 17.

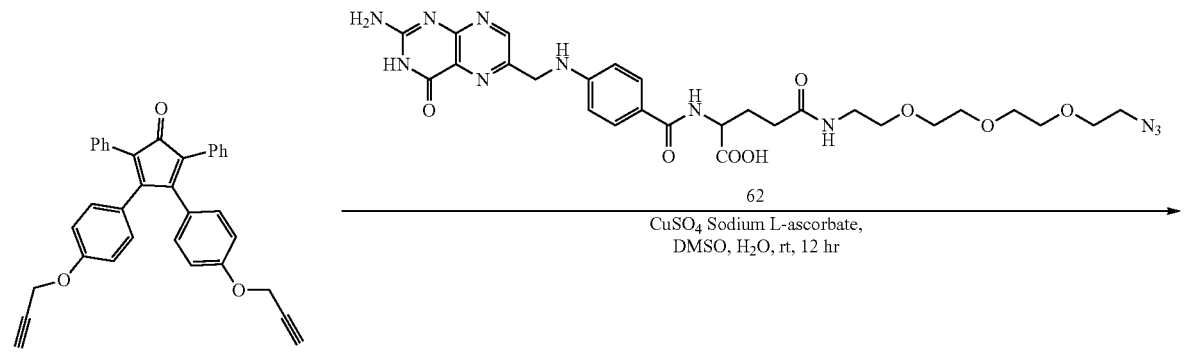

-continued
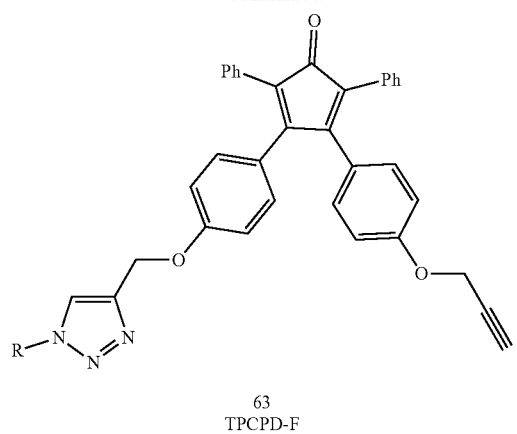
63
TPCPD-F
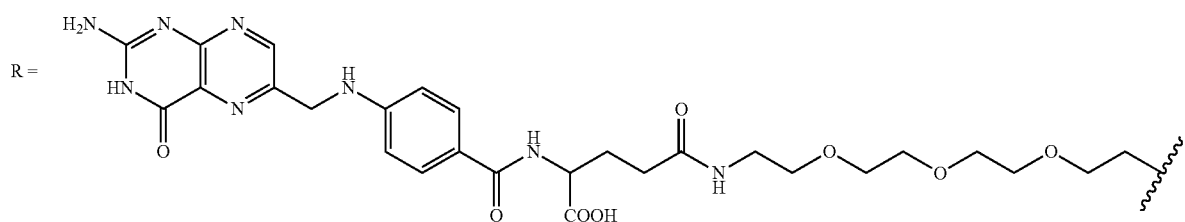
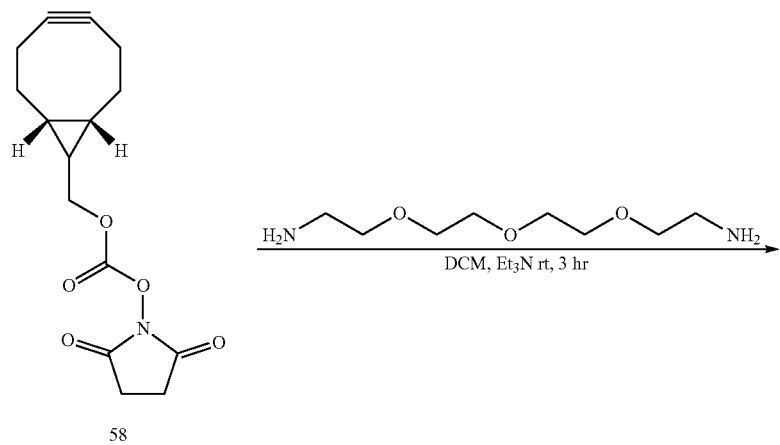
58
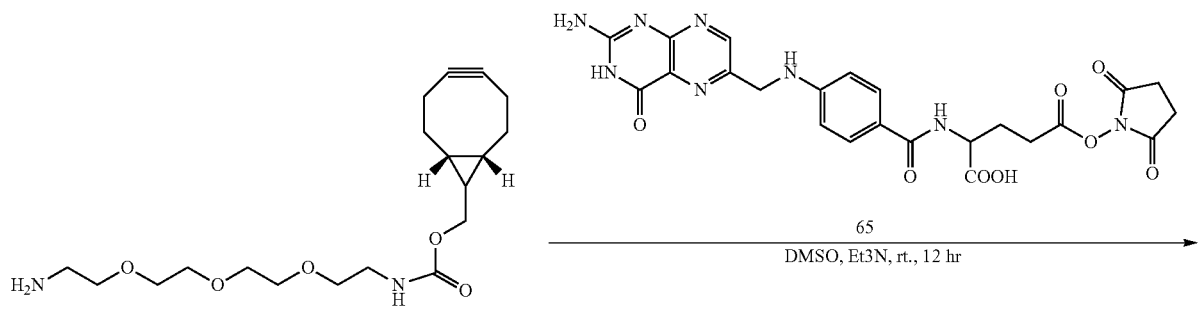
64

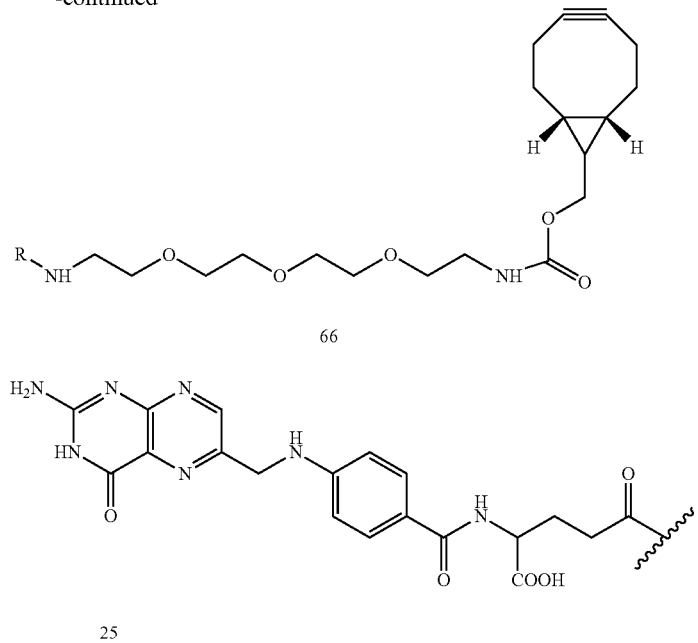

66

R = [structure of folic acid derivative with H₂N, pteridine, NH, benzamide, COOH groups]

Preparation of TPCPD-F (63)

To a 5 mL vial, compound 54 (15 mg, 0.03 mmol), azido-folic acid 62 (6.4 mg, 0.01 mmol), CuSO4.5H₂O (3.7 mg, 0.015 mmol), (+)-sodium L-ascorbate (8 mg, 0.04 mmol), DMSO (0.9 mL) and H₂O (0.1 mL) were added. The reaction was kept stirring at room temperature for 12 hr, diluted with H₂O (1 mL), and poured into diethyl ether (13 mL). The brown dark solid was separated through centrifugation and washed with methanol (10 mL) and diethyl ether (20 mL). After drying under vacuum, brown dark solid 63 was obtained (5.6 mg, yield: 49%).

Preparation of BCN-F (66)

To a solution of 4,7,10-Trioxa-1,13-tridecanediamine (220 mg, 1.0 mmol) and triethylamine (30 mg, 0.3 mmol) in CH₂Cl₂ (0.8 mL), compound 58 (29 mg, 0.1 mmol) in CH₂Cl₂ (0.5 mL) was added dropwise in 5 min. The reaction was stirred at room temperature for 3 hr and diluted with ethyl acetate (20 mL). The organic layer was washed with H₂O (3×3 mL) and dried by Na₂SO₄. Solvent was removed by using a rotavapor to yield colorless oil 64 (32 mg), which was directly used in next step without further purification. To a solution of NHS-folic acid 65 (43 mg, 0.08 mmol) in DMSO (1 mL), compound 64 (32 mg, 0.08 mmol) in DMSO (0.5 mL) was added, followed by the addition of triethylamine (10 mg, 0.1 mmol). The reaction was kept stirring at room temperature for 12 hr, diluted with dichloromethylene (5 mL), and then poured into diethyl ether (30 mL). The yellow precipitate was filtered, washed with diethyl ether (30 mL), and dried by vacuum to give yellow solid 66 (42 mg, yield: 51%).

Example 9. CO Displays Anti-Inflammatory Effects on Macrophage Cell Line

Recent studies have reported that at the concentration range of 100-250 ppm in carrier gas (air), exogenous CO differentially and selectively suppresses the expression of lipopolysaccharide (LPS)-induced proinflammatory cytokines TNF-a, interleukin-1b and macrophage expression of the anti-inflammatory cytokine IL-10 from macrophages.

Figure 5:
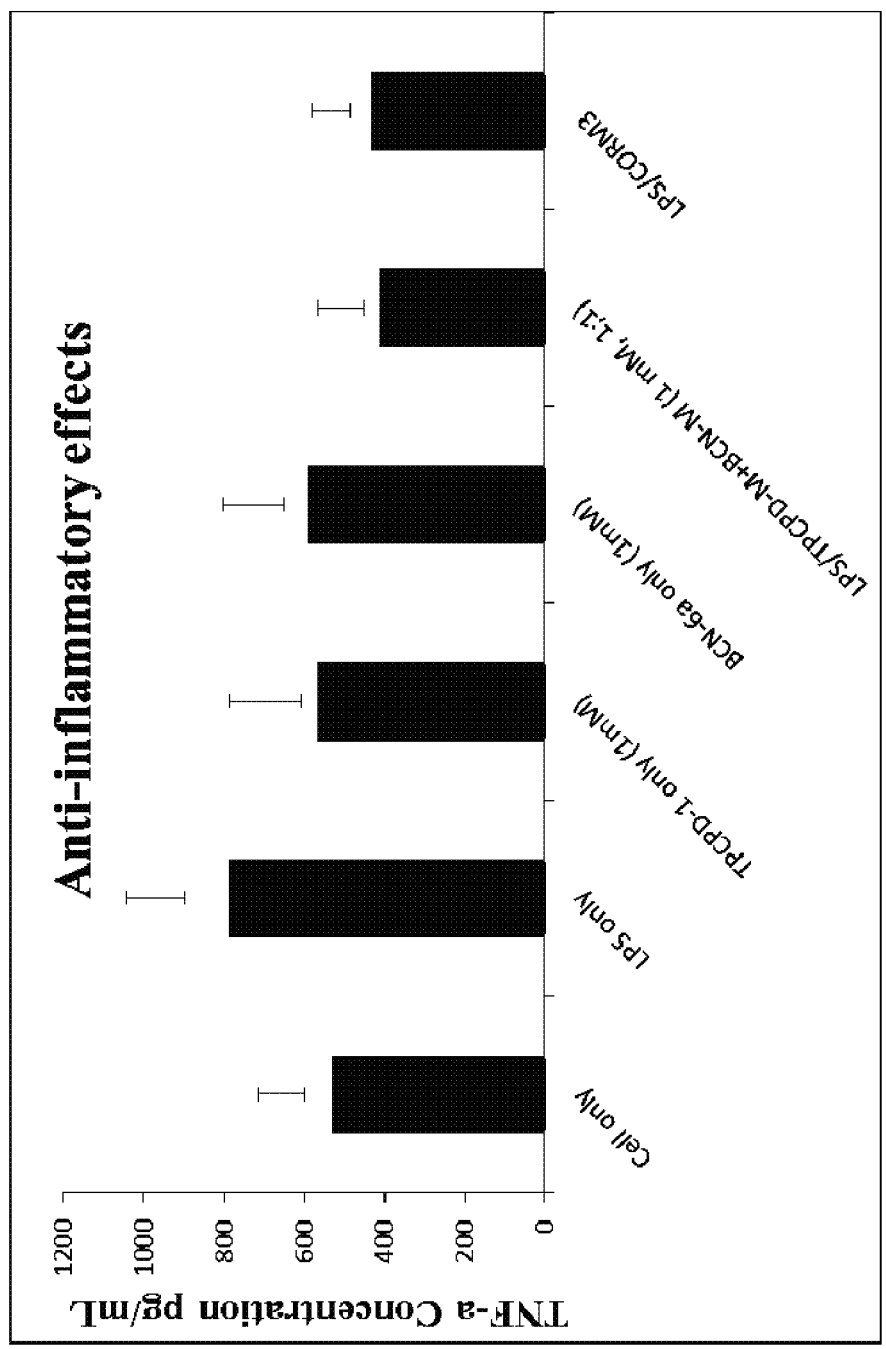
FIG. 5 shows a graph showing the amount of secretion of TNFα as a function of the concentration of reactants and products after 24 hours.

TNF-α is a major pro-inflammatory cytokine, mainly secreted from macrophages and dendritic cells. Its production is induced in vitro by stimulation with LPS. The accumulation of TNF-α was assessed by ELISA in the culture supernatant of the macrophage cell line, RAW 264.7 (FIG. 5). The cells were stimulated for 1 h and then co-treated by TPCPD-M (61) and BCN-M (57) for 24 h. As shown in FIG. 4, LPS stimulation at 10 ng/mL induced a 2-fold increase in secretion of TNF-α in culture supernatant. A 50% decrease of the LPS-induced accumulation of TNF-α was observed after co-treatment with TPCPD-M and BCN-M at the respective concentration of 1 mM+1 mM.

As a control, the effect of the TPCPD-M and BCN-M were tested separately (FIG. 5). These compounds or their corresponding cycloaddition product do not lead to any inhibition of the LPS-induced accumulation of TNF-α. Altogether, these data demonstrate that the CO produced from the reaction between TPCPD-M and BCN-M displayed anti-inflammatory effects in macrophage cell culture.

Example 10. Cell Imaging Studies for Two-Component CO Releasing Systems

In order to facilitate the monitoring of CO release, fused polycyclic dienones were designed. After the cyclization reaction, CO was released along with a fluorescent molecule, which could be used to monitor CO release.

HeLa cells were cultured in DMEM (Dulbecco's Modified Eagle's Medium) supplemented with 10% heat inactivated FBS (fetal bovine serum) and 1% PSN (penicillin-streptomycin). For the live cell imaging, HeLa cells were seeded in 6-well plates one day before the imaging experiment. 100 μM BCN with different concentrations (5 μM, 10 μM and 20 μM) of compound 2b was added into the cell culture and incubated for 4 hours at 37° C. The cells treated with compound 2b only, without BCN, were tested as controls. After 4 hours, the cell culture media containing compounds was replaced with fresh DMEM. For the fixed cell imaging, the cells were seeded on microscope square glass cover slips in 6-well plates one day before the imaging experiment. The cells were then treated with either compound 2b only (5 µM, 10 µM and 20 µM), or compound 2b together with 100 µM BCN, for 4 hours at 37° C. Thereafter, the cells were washed with PBS and fixed in 4% paraformaldehyde for 30 minutes at room temperature. The fixed cells were then immersed in 0.3M glycine for 20 minutes at room temperature to quench the autofluorescence from formaldehyde. After that, the coverslips containing the cell samples were washed with water and mounting onto glass slides by hard-set mounting media. The fluorescent images were taken under DAPI channel (excitation: 358 nm; emission: 461 nm) using a Zeiss fluorescent microscope.

Figure 6:
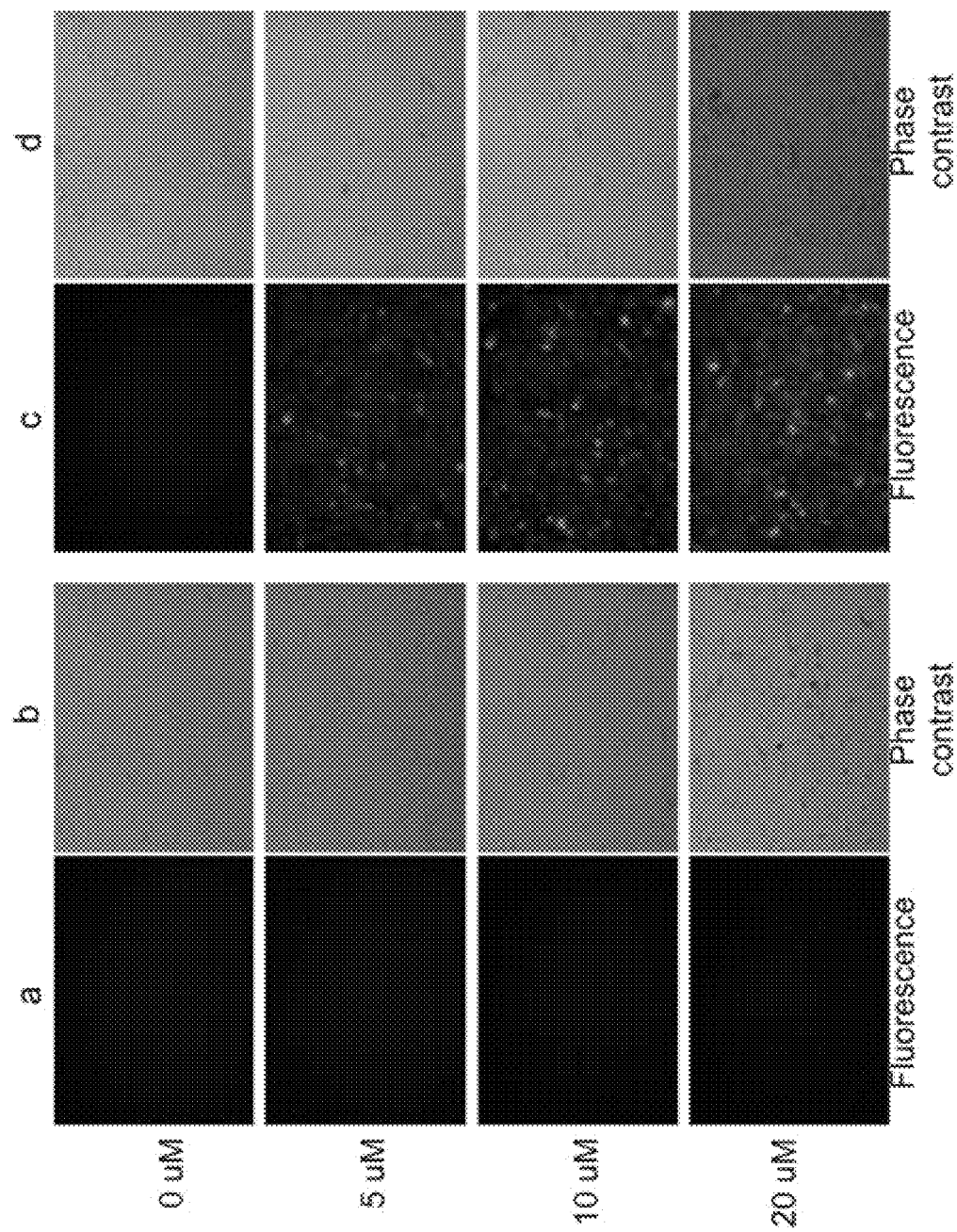
FIG. 6 shows a fluorescent imaging of living HeLa cells treated with compound 2b and 100 μM exo-BCN+compound 2b: (a) fluorescent images of live HeLa cells treated with compound 2b; (b) corresponding phase contrast images of (a); (c) fluorescent images of live HeLa cells treated with 100 μM exo-BCN+compound 2b; and (d) corresponding phase contrast images of (c).
Figure 7:
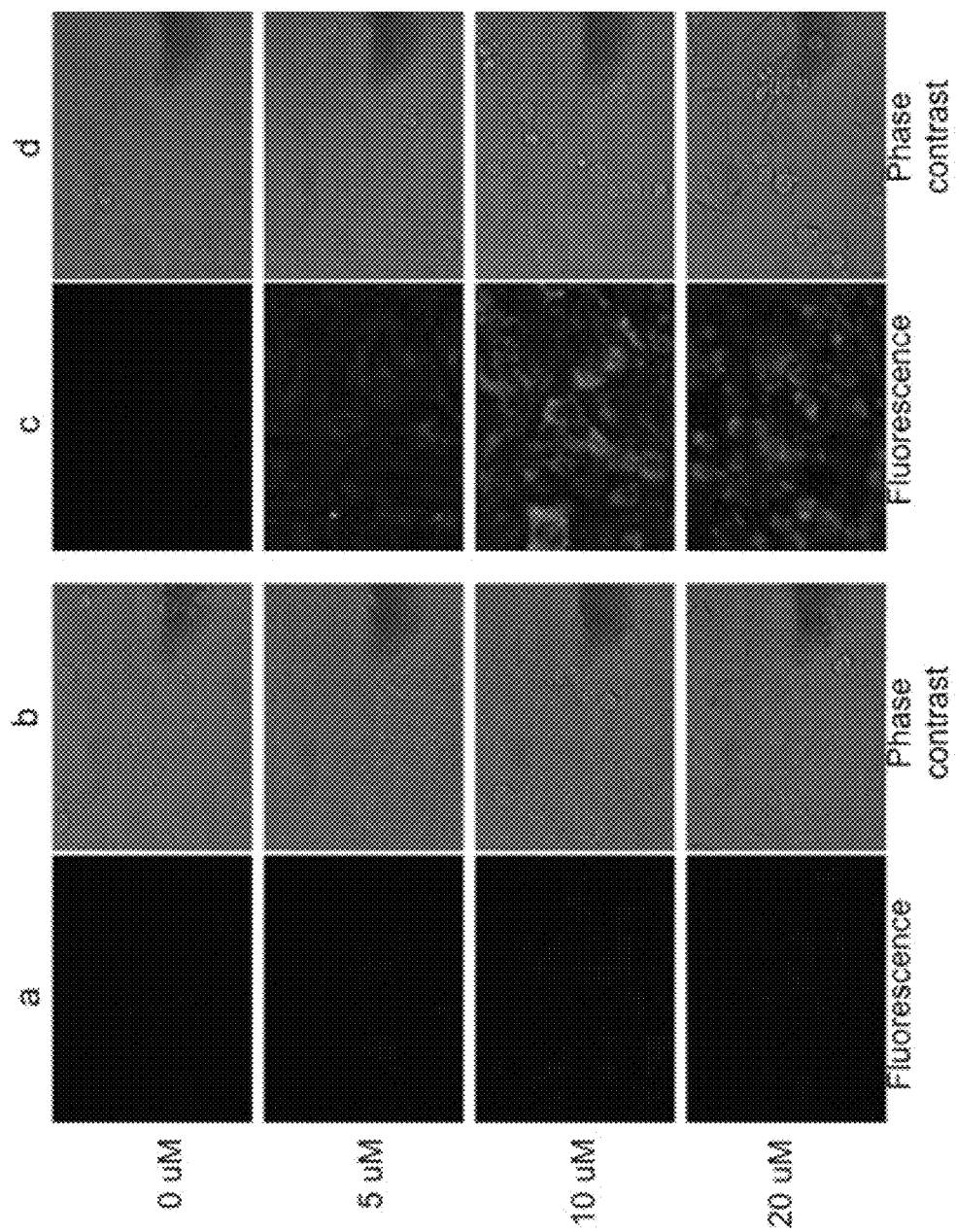
FIG. 7 shows a fluorescent imaging of fixed HeLa cells treated with compound 2b and 100 μM exo-BCN+compound 2b: (a) fluorescent images of fixed HeLa cells treated with compound 2b; (b) corresponding phase contrast images of (a); (c) fluorescent images of fixed HeLa cells treated with 100 μM exo-BCN+compound 2b; and (d) corresponding phase contrast images of (c).

The results are shown in FIG. 6 and FIG. 7. The cells treated with compound 2b only shows no fluorescence. The cells treated with both BCN and compound 2b shows fluorescence in a concentration dependent manner.

Example 11. Cell Imaging Studies for One-Component CO Releasing Systems

HeLa cells, or RAW 264.7 cells were cultured in DMEM (Dulbecco's Modified Eagle's Medium) supplemented with 10% heat inactivated FBS (fetal bovine serum) and 1% PSN (penicillin-streptomycin). For live cell imaging, the cells were seeded in 6-well plates one day before the imaging experiment. Different concentrations of compound 10b were added into the cell culture and incubated for 3 hours at 37° C. After 3 hours, the cell culture media containing compounds was replaced with fresh DMEM. For fixed cell imaging, the cells were seeded on microscope square glass cover slips in 6-well plates one day before the imaging experiment. The cells were then treated with different concentrations of compound 10b for 3 hours at 37° C. Thereafter, the cells were washed with PBS and fixed in 4% paraformaldehyde for 30 minutes at room temperature. The fixed cells were then immersed in 0.3M glycine for 20 minutes at room temperature to quench the autofluorescence from formaldehyde. After that, the coverslips containing the cell samples were washed with water and mounting onto glass slides by hard-set mounting media. The fluorescent images were taken under DAPI channel (excitation: 358 nm; emission: 461 nm) using a Zeiss fluorescent microscope.

Figure 8:
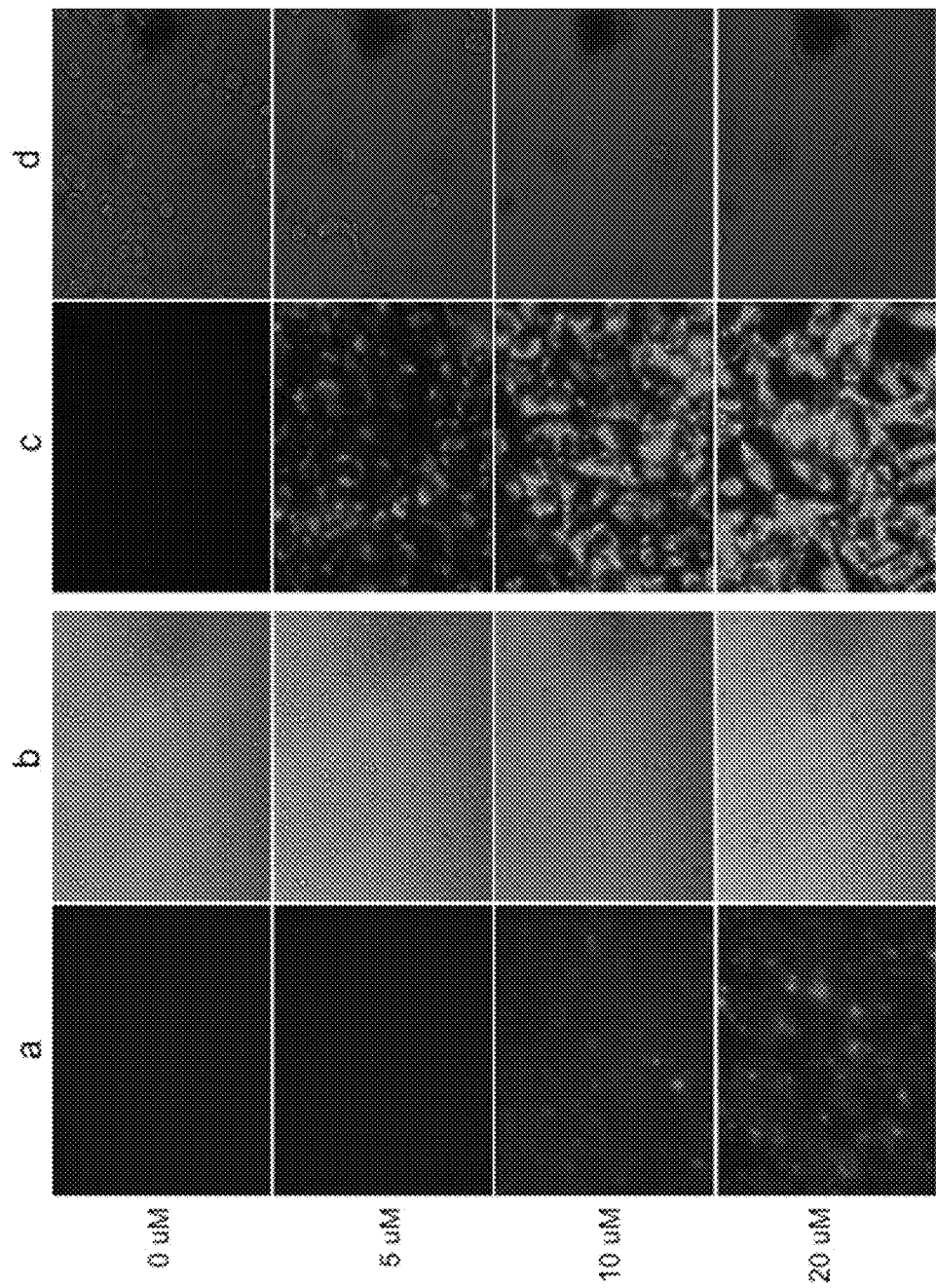
FIG. 8 shows a fluorescent imaging of HeLa cells treated with compound 10b: (a) fluorescent images of live HeLa cells treated with compound 10b; (b) corresponding phase contrast images of (a); (c) fluorescent images of fixed HeLa cells treated with compound 10b; and (d) corresponding phase contrast images of (c).
Figure 9:
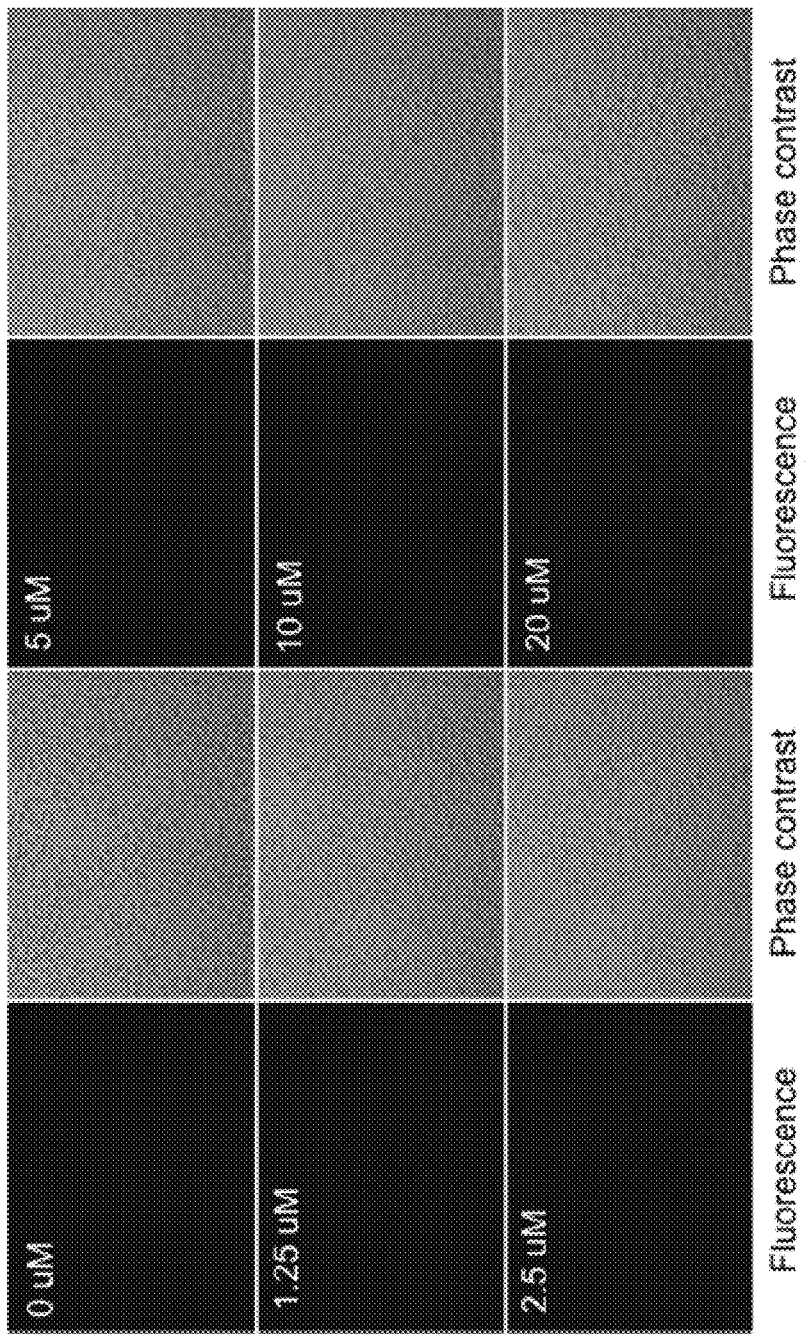
FIG. 9 shows a fluorescent imaging of living RAW 264.7 cells treated with different concentrations of compound 10b. (The second and forth rows are corresponding phase contrast images of first and third rows).
Figure 10:
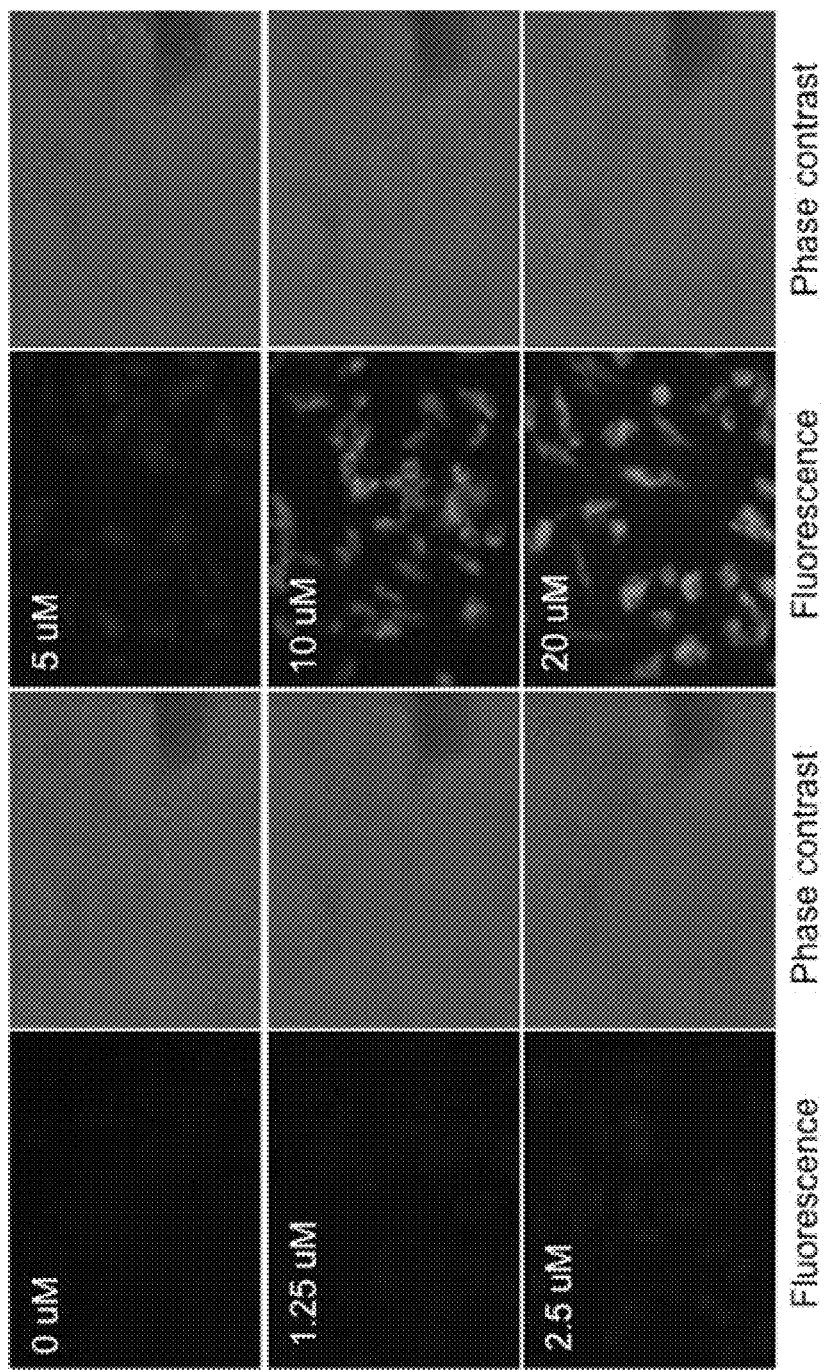
FIG. 10 shows a fluorescent imaging of fixed RAW 264.7 cells treated with different concentrations of compound 10b. (The second and forth rows are corresponding phase contrast images of first and third rows).

The results are shown in FIGS. 8-10. The fluorescence intensity of the treated cells increases with the increase in concentration of compound 10b. It can be seen in the images that CO was released primarily in cytoplasm.

Example 12. Cytotoxicity of Compound 10b

Figure 11:
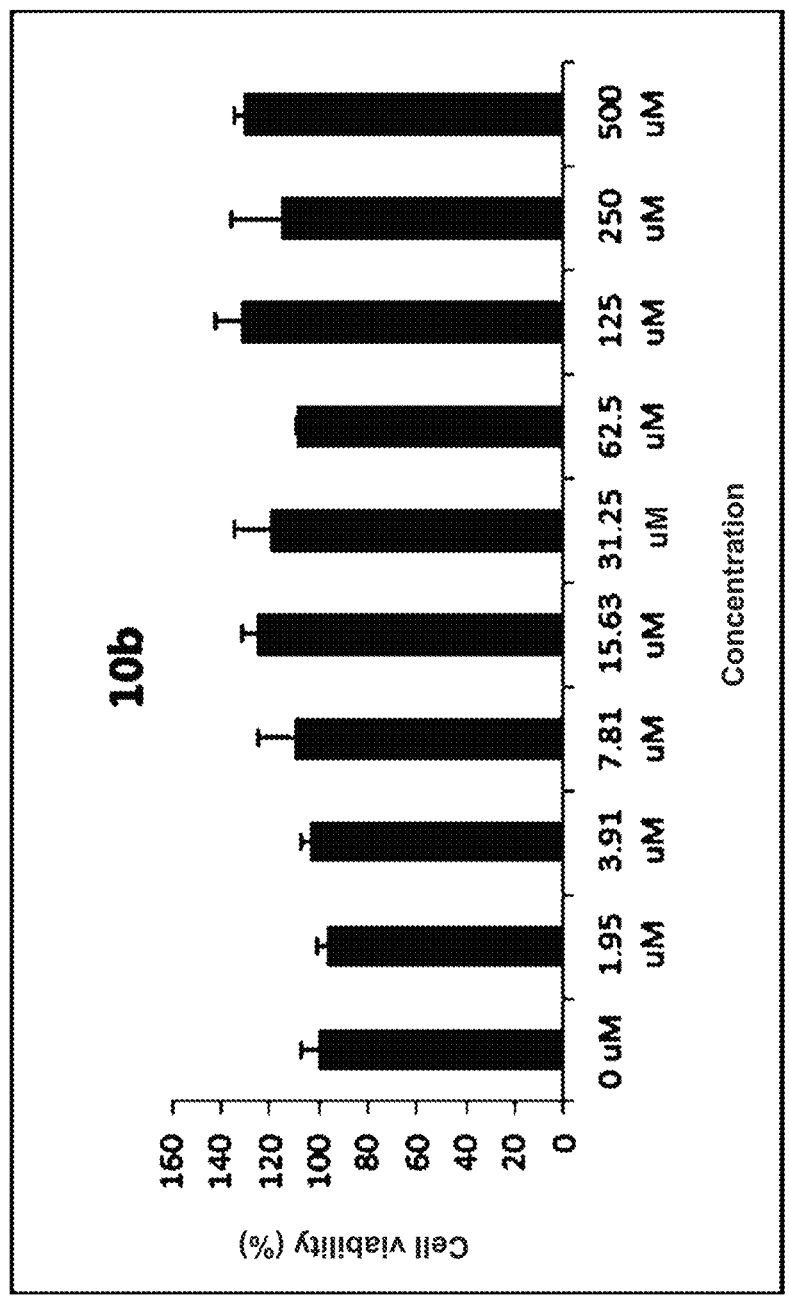
FIG. 11 shows cytotoxicity studies of compound 10b on RAW 264.7 cell for 24 hours.
Figure 12:
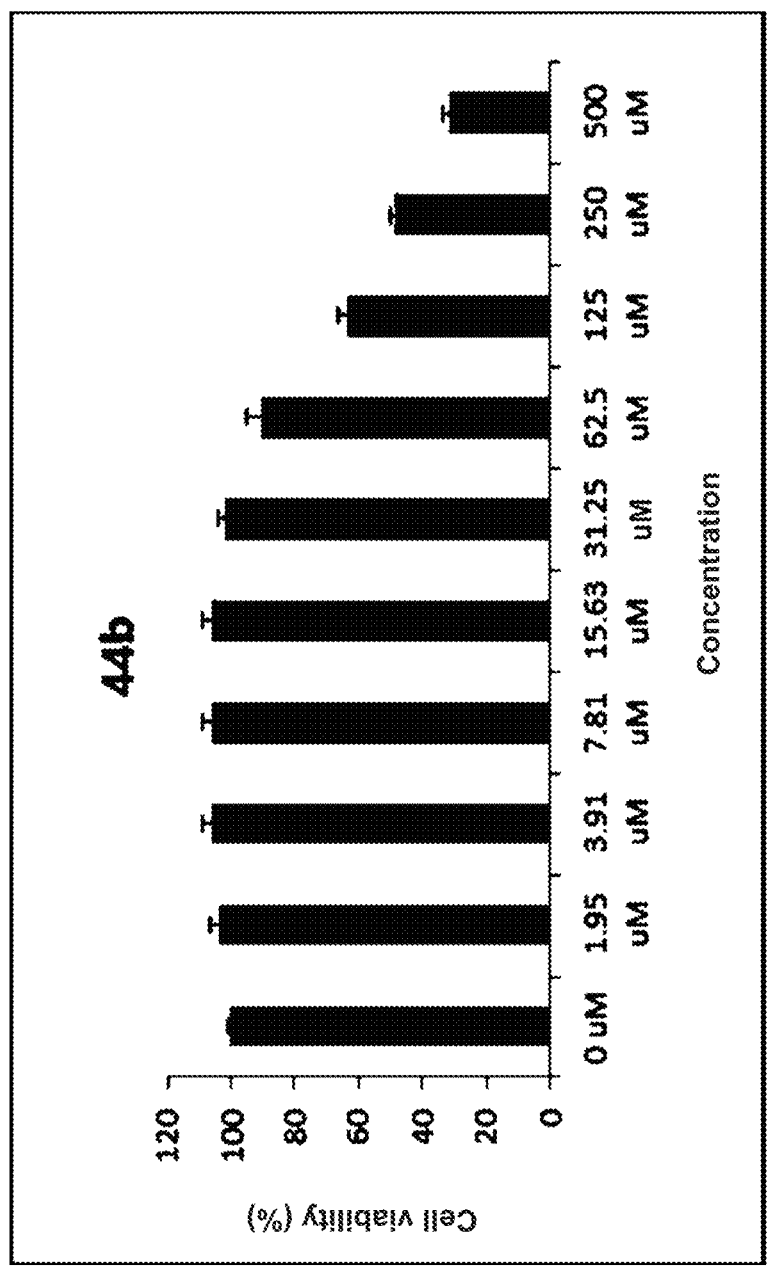
FIG. 12 shows cytotoxicity studies of compound 44b on RAW 264.7 cell for 24 hours.

The toxicity of compound 10b and product of compound 10b (44b) after CO release were tested on RAW 264.7 cells, which is a mouse macrophage cell line used for anti-inflammation test. Different concentrations of 10b and 44b product were added into the cell culture media (Dulbecco's Modified Eagle's Medium supplemented with 10% heat inactivated fetal bovine serum and 1% penicillin-streptomycin). All samples with different concentrations of 10b or 44b product contained 1% DMSO in the cell culture media. RAW 264.7 cells were seeded in 96-well plate one day before the experiment. The cells were then incubated with the compound for 24 hours at 37° C. with 5% $CO_2$. The cell viability was tested by MTT assay. Basically, after 24 hours of incubation, 0.5 mg/mL MTT (3-(4,5-Dimethylthiazol-2-yl)-2,5-Diphenyltetrazolium Bromide) was added into the cell culture and incubated for 4 hours. Thereafter, the supernatant was removed and 100 µL of DMSO were added into the wells containing cells. After shaking gently for 3 minutes, absorbance at 570 nm was read by plate reader. The results are shown in FIGS. 11 and 12.

Figure 13:
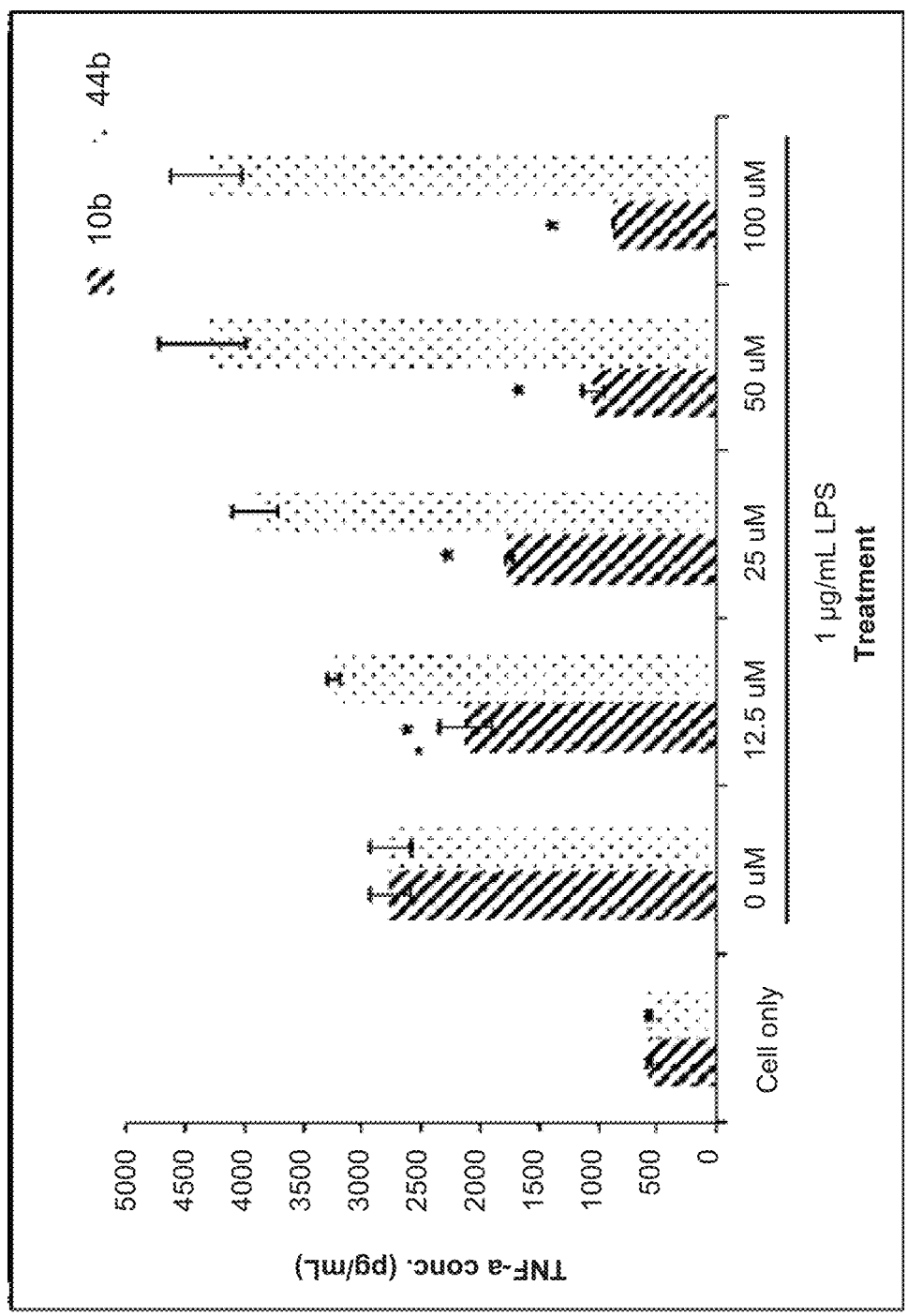
FIG. 13 shows the effect of compound 10b on TNF-α expression in RAW 264.7 cells. (*p<0.05).
Figure 14:
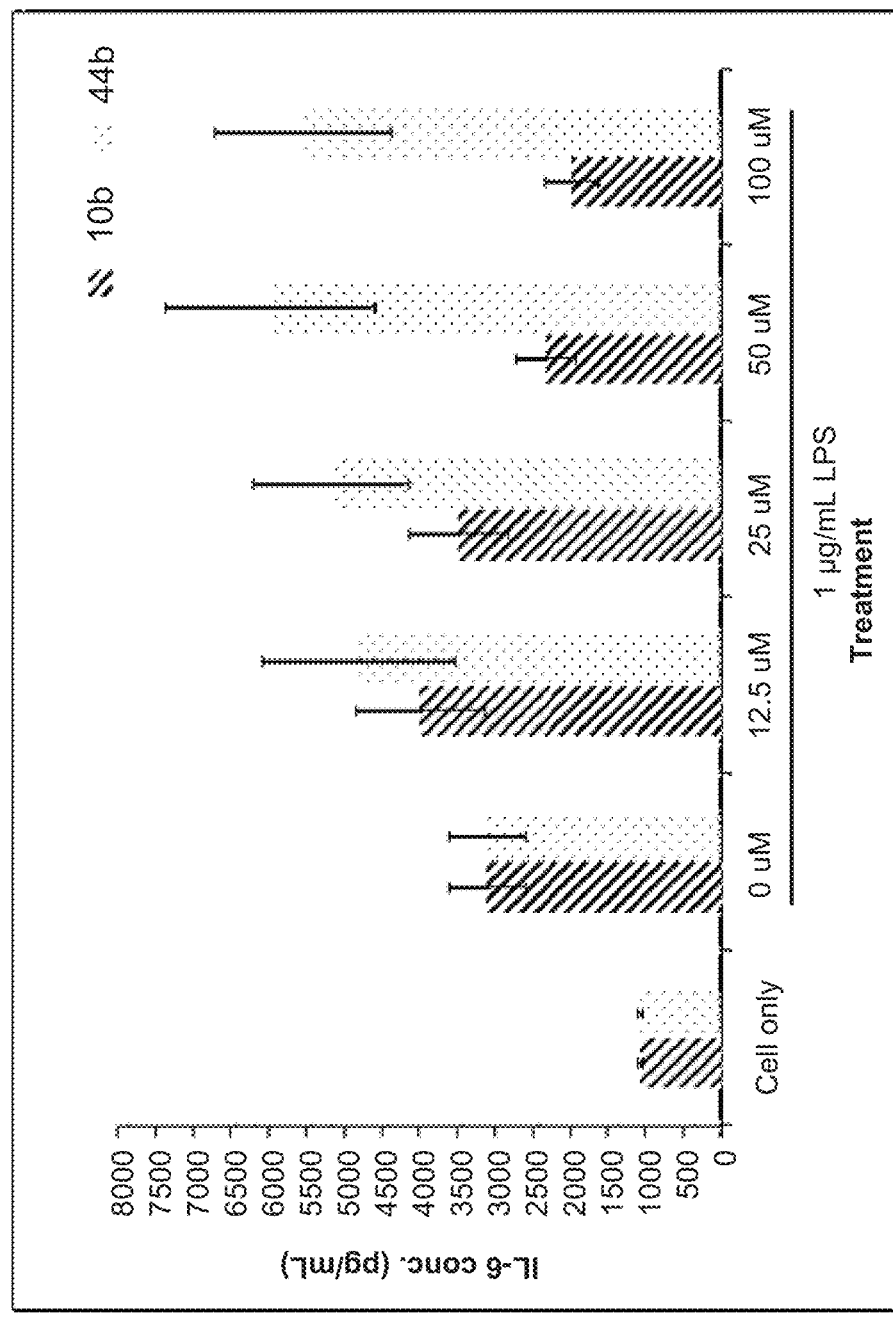
FIG. 14 shows the effect of compound 10b on IL-6 expression in RAW 264.7 cells.

Example 13. Unimolecular CO Prodrug Displays Anti-Inflammatory Effects on Macrophage Cell Line RAW 264.7 cells were seeded in the 48-well plate one day before the experiment. LPS was used to initialize the inflammatory response in RAW 264.7 cells and trigger the expression of cytokines. RAW 264.7 cells were pre-treated with different concentrations of 10b or 44b product for 5 hours. Thereafter, 1 µg/mL LPS was added with into the cell culture media. For TNF-α test, the cell culture supernatant was collected after 1 hour of LPS treatment. For IL-6 test, the cell culture supernatant was collected after 4 hours of LPS treatment. Cell culture without LPS treatment was used as control. The concentrations of cytokines in the cell culture supernatant were measurement by a commercial ELISA kit (ELISA Ready-SET-Go!®-eBioscience), the results obtained are shown in FIGS. 13 and 14. Compound 10b concentration dependently decreases the expression of TNF-α and IL-6 in LPS treated RAW 264.7 cells.

Unless defined otherwise, all technical and scientific terms used herein have the same meanings as commonly understood by one of skill in the art to which the disclosed invention belongs. Publications cited herein and the materials for which they are cited are specifically incorporated by reference. Those skilled in the art will recognize, or be able to ascertain using no more than routine experimentation, many equivalents to the specific embodiments of the invention described herein. Such equivalents are intended to be encompassed by the claims.

What is claimed is:

1. A compound according to Formula IX:

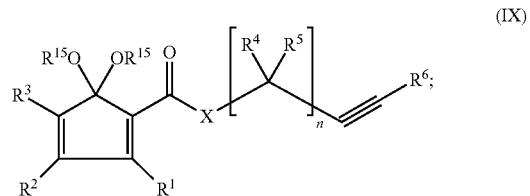

(IX)

or a pharmaceutically acceptable salt thereof, wherein:
$R^1$ and $R^2$ are phenyl, each of which is optionally substituted with one or more $R^{11}$ moieties, or $R^1$ and $R^2$ are phenyl and are taken together to form a fused tricyclic moiety which is optionally substituted with one or more $R^{11}$ moieties, wherein
$R^3$ is selected from the group consisting of cycloalkyl, heterocycloalkyl, aryl, and heteroaryl;
each $R^4$ and $R^5$ is independently selected from the group consisting of hydrogen, substituted or unsubstituted alkyl, cycloalkyl, heterocycloalkyl, alkenyl, alkynyl, aryl, heteroaryl, a protecting moiety $R^P$, a linking moiety $R^L$, a targeting moiety $R^T$, and a solubility-enhancing moiety $R^S$;
$R^6$ is independently selected from the group consisting of substituted or unsubstituted alkyl, cycloalkyl, heterocycloalkyl, alkenyl, alkynyl, aryl, heteroaryl, a protecting moiety $R^P$, a linking moiety $R^L$, a targeting moiety $R^T$, and a solubility-enhancing moiety $R^S$;
each $R^{11}$ is independently selected from the group consisting of halogen, alkyl, cycloalkyl, heterocycloalkyl, alkenyl, alkynyl, aryl, heteroaryl, alkoxy, aryloxy, hydroxyl, —N(R$^a$)$_2$, —SR$^a$, —S(O)R$^a$, —S(O)$_2$R$^a$, —OS(O)OR$^a$, —OS(O)$_2$OR$^a$, —OP(OR$^a$)$_2$, —OP(O)HOR$^a$, —OP(OR$^a$)$_2$, —OP(O)(R$^a$)$_2$, —P(O)(OR$^a$)$_2$, —ONO, —ONO$_2$, —NO$_2$, —(C═O)R$^5$, —(C═O)OR$^6$, —(C═O)NR$^7$R$^8$, a linking moiety R$^L$, a targeting moiety R$^T$, and a solubility-enhancing moiety R$^S$;

R$^a$ is selected from the group consisting of hydrogen, alkyl, cycloalkyl, aryl, and heteroaryl;

each R$^7$, R$^8$, R$^9$, and R$^{10}$ is independently selected from the group consisting of hydrogen, alkyl, heteroalkyl, alkenyl, heteroalkenyl, alkynyl, heteroalkynyl, cycloalkyl, heterocycloalkyl, aryl, and heteroaryl;

X is NR$^{14}$ wherein R$^{14}$ is hydrogen or alkyl, which is optionally substituted with halogen, haloalkyl, haloalkoxy, —OR', or —NR'R", R' and R" are independently selected from the group consisting of hydrogen and unsubstituted alkyl; or R' and R", when attached to the same nitrogen atom, are combined with the nitrogen to which they are attached to form heterocycloalkyl or heteroaryl;

each R$^{15}$ is independently selected from the group consisting of hydrogen, alkyl, cycloalkyl, heterocycloalkyl, alkenyl, alkynyl, aryl, and heteroaryl, or, alternatively two OR' are taken together to form an oxo moiety; and subscript n is 1, 2 or 3.

2. The compound of claim 1, wherein R$^4$ and R$^5$ are hydrogen.

3. The compound of claim 2, wherein subscript n is 1 or 2.

4. The compound of claim 1, wherein X is NR$^{14}$ and R$^{14}$ is selected from the group consisting of hydrogen, alkyl, and heteroalkyl.

5. The compound of claim 4, wherein R$^4$ and R$^5$ are hydrogen.

6. The compound of claim 5, wherein subscript n is 1 or 2.

7. A method for generating carbon monoxide in vivo or ex vivo, the method comprising:
allowing a precursor molecule according to claim 1 to react to form an organic molecule that releases carbon monoxide under physiological conditions.

8. The method of claim 7, wherein the carbon monoxide is released in an amount effective for the treatment of inflammation, cardiovascular disease, cancer, sepsis, or a combination thereof.

9. The method of claim 8, wherein R$^4$ and R$^5$ are hydrogen.

10. The method of claim 9, wherein subscript n is 1 or 2.

11. The method of claim 8, wherein X is NR$^{14}$ and R$^{14}$ is selected from the group consisting of hydrogen, alkyl, and heteroalkyl.

12. The method of claim 11, wherein R$^4$ and R$^5$ are hydrogen.

13. The method of claim 12, wherein subscript n is 1 or 2.

14. A method for treating inflammation, cardiovascular disease, cancer, sepsis, or a combination thereof, the method comprising administering an effective amount of a compound according to claim 1 to a subject in need thereof.

15. The method of claim 14, wherein R$^4$ and R$^5$ are hydrogen.

16. The method of claim 15, wherein subscript n is 1 or 2.

17. The method of claim 14, wherein X is NR$^{14}$ and R$^{14}$ is selected from the group consisting of hydrogen, alkyl, and heteroalkyl.

18. The method of claim 17, wherein R$^4$ and R$^5$ are hydrogen.

19. The method of claim 18, wherein subscript n is 1 or 2.

20. The method of claim 14, wherein the compound is administered parenterally.

* * * * *

UNITED STATES PATENT AND TRADEMARK OFFICE
CERTIFICATE OF CORRECTION

PATENT NO. : 10,751,344 B2
APPLICATION NO. : 16/423094
DATED : August 25, 2020
INVENTOR(S) : Binghe Wang et al.

Page 1 of 1

It is certified that error appears in the above-identified patent and that said Letters Patent is hereby corrected as shown below:

In the Claims

In Column 81, Line 4, Claim 1, delete "-OP(OR$^a$)$_2$," and insert -- -OP(O)(OR$^a$)$_2$, --.

In Column 81, Line 16, Claim 1, delete "-NR'R"," and insert -- -NR'R"; --.

In Column 81, Line 25, Claim 1, delete "OR" and insert -- OR$^{15}$ --.

Signed and Sealed this
Thirteenth Day of February, 2024

Katherine Kelly Vidal
*Director of the United States Patent and Trademark Office*